(12) United States Patent
Altarac et al.

(10) Patent No.: US 10,278,744 B2
(45) Date of Patent: May 7, 2019

(54) SYSTEMS AND METHODS FOR POSTERIOR DYNAMIC STABILIZATION OF THE SPINE

(71) Applicant: The Board of Trustees of the Leland Stanford Junior University, Palo Alto, CA (US)

(72) Inventors: Moti Altarac, Irvine, CA (US); Shawn Tebbe, Oceanside, CA (US); Daniel H. Kim, Houston, TX (US); J. Christopher Flaherty, Topsfield, MA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 164 days.

(21) Appl. No.: 14/693,572

(22) Filed: Apr. 22, 2015

(65) Prior Publication Data

US 2016/0030092 A1     Feb. 4, 2016

Related U.S. Application Data

(63) Continuation of application No. 13/442,751, filed on Apr. 9, 2012, now Pat. No. 9,039,742, which is a
(Continued)

(51) Int. Cl.
*A61B 17/70* (2006.01)
*A61B 17/02* (2006.01)
(Continued)

(52) U.S. Cl.
CPC ........ *A61B 17/7065* (2013.01); *A61B 17/025* (2013.01); *A61B 17/1671* (2013.01);
(Continued)

(58) Field of Classification Search
CPC .............................. A61B 17/7062–2017/7073
See application file for complete search history.

(56) References Cited

U.S. PATENT DOCUMENTS 2,248,054 A    7/1941 Becker
2,677,369 A    5/1954 Knowles
(Continued)

FOREIGN PATENT DOCUMENTS

CA        268461 A      2/1927
CN      2794456 Y      7/2006
(Continued)

OTHER PUBLICATIONS

International Search Report and Written Opinion; Application No. PCT/US2005/038026; dated Apr. 22, 2008, 9 pages.
(Continued)

*Primary Examiner* — Christopher D. Prone
(74) *Attorney, Agent, or Firm* — Perkins Coie LLP

(57) ABSTRACT

Devices, systems and methods for dynamically stabilizing the spine are provided. The devices include an expandable spacer having an undeployed configuration and a deployed configuration, wherein the spacer has axial and radial dimensions for positioning between the spinous processes of adjacent vertebrae. The systems include one or more spacers and a mechanical actuation means for delivering and deploying the spacer. The methods involve the implantation of one or more spacers within the interspinous space.

17 Claims, 48 Drawing Sheets

Related U.S. Application Data continuation of application No. 11/314,712, filed on Dec. 20, 2005, now Pat. No. 8,152,837, which is a continuation-in-part of application No. 11/190,496, filed on Jul. 26, 2005, now Pat. No. 8,409,282, which is a continuation-in-part of application No. 11/079,006, filed on Mar. 10, 2005, now Pat. No. 8,012,207, which is a continuation-in-part of application No. 11/052,002, filed on Feb. 4, 2005, now Pat. No. 8,317,864, which is a continuation-in-part of application No. 11/006,502, filed on Dec. 6, 2004, now Pat. No. 8,123,807, which is a continuation-in-part of application No. 10/970,843, filed on Oct. 20, 2004, now Pat. No. 8,167,944.

(51) Int. Cl.
  *A61B 17/16* (2006.01)
  *A61B 17/17* (2006.01)
  *A61B 17/34* (2006.01)
  *A61B 17/88* (2006.01)
  A61B 17/84 (2006.01)
  A61B 17/00 (2006.01)
  A61F 2/00 (2006.01)
  A61B 17/68 (2006.01)
  A61B 90/00 (2016.01)

(52) U.S. Cl.
  CPC ...... *A61B 17/1697* (2013.01); *A61B 17/1757* (2013.01); *A61B 17/3421* (2013.01); *A61B 17/8866* (2013.01); A61B 17/0206 (2013.01); A61B 17/7062 (2013.01); A61B 17/848 (2013.01); A61B 17/8897 (2013.01); A61B 90/39 (2016.02); A61B 2017/00004 (2013.01); A61B 2017/0023 (2013.01); A61B 2017/00261 (2013.01); A61B 2017/00557 (2013.01); A61B 2017/0256 (2013.01); A61B 2017/681 (2013.01); A61B 2090/033 (2016.02); A61B 2090/034 (2016.02); A61B 2090/062 (2016.02); A61F 2/0077 (2013.01)

(56) References Cited

U.S. PATENT DOCUMENTS

| | | | |
|---|---|---|---|
| 2,933,114 A | 4/1960 | Bystrom | |
| 3,242,120 A | 3/1966 | Steuber | |
| 3,486,505 A | 12/1969 | Morrison | |
| 3,648,691 A | 3/1972 | Lumb et al. | |
| 3,780,733 A | 12/1973 | Martinez | |
| 3,986,383 A | 10/1976 | Petteys | |
| 4,545,374 A | 10/1985 | Jacobson | |
| 4,632,101 A | 12/1986 | Freedland | |
| 4,685,447 A | 8/1987 | Iversen et al. | |
| 4,799,484 A | 1/1989 | Smith et al. | |
| 4,863,476 A | 9/1989 | Shepperd | |
| 4,895,564 A | 1/1990 | Farrell | |
| 4,986,831 A | 1/1991 | King et al. | |
| 5,011,484 A | 4/1991 | Breard et al. | |
| 5,019,081 A | 5/1991 | Watanabe | |
| 5,040,542 A | 8/1991 | Gray | |
| 5,059,193 A | 10/1991 | Kuslich | |
| 5,092,866 A | 3/1992 | Breard et al. | |
| 5,180,393 A | 1/1993 | Commarmond et al. | |
| 5,188,281 A | 2/1993 | Fujiwara et al. | |
| 5,192,281 A | 3/1993 | de la Caffiniere | |
| 5,195,526 A | 3/1993 | Michelson | |
| 5,298,253 A | 3/1994 | LeFiles et al. | |
| 5,368,594 A | 11/1994 | Martin et al. | |
| 5,390,683 A | 2/1995 | Pisharodi | |
| 5,415,661 A | 5/1995 | Holmes | |
| 5,456,722 A | 10/1995 | McLeod et al. | |
| 5,462,738 A | 10/1995 | LeFiles et al. | |
| 5,472,452 A | 12/1995 | Trott | |
| 5,484,437 A | 1/1996 | Michelson | |
| 5,487,739 A | 1/1996 | Aebischer et al. | |
| 5,489,308 A | 2/1996 | Kuslich et al. | |
| 5,496,318 A | 3/1996 | Howland et al. | |
| 5,531,748 A | 7/1996 | de la Caffiniere et al. | |
| 5,549,679 A | 8/1996 | Kuslich | |
| 5,571,189 A | 11/1996 | Kuslich | |
| 5,591,165 A | 1/1997 | Jackson | |
| 5,609,634 A | 3/1997 | Voydeville et al. | |
| 5,609,636 A | 3/1997 | Kohrs et al. | |
| 5,645,599 A * | 7/1997 | Samani | 606/248 |
| 5,654,599 A | 8/1997 | Casper | |
| 5,658,335 A | 8/1997 | Allen | |
| 5,658,337 A | 8/1997 | Kohrs et al. | |
| 5,674,295 A | 10/1997 | Ray et al. | |
| 5,700,264 A | 12/1997 | Zucherman et al. | |
| 5,725,582 A | 3/1998 | Bevan et al. | |
| 5,741,253 A | 4/1998 | Michelson | |
| 5,746,720 A | 5/1998 | Stouder, Jr. | |
| 5,762,629 A | 6/1998 | Kambin | |
| 5,836,948 A | 11/1998 | Zucherman et al. | |
| 5,860,977 A | 1/1999 | Zucherman et al. | |
| 5,863,948 A | 1/1999 | Epstein et al. | |
| 5,876,404 A | 3/1999 | Zucherman et al. | |
| RE36,211 E | 5/1999 | Nonomura et al. | |
| 5,904,636 A | 5/1999 | Chen et al. | |
| 5,904,686 A | 5/1999 | Zucherman et al. | |
| 5,928,207 A | 7/1999 | Pisano et al. | |
| 5,948,017 A | 9/1999 | Taheri | |
| 5,972,015 A | 10/1999 | Scribner et al. | |
| 6,039,761 A | 3/2000 | Li et al. | |
| 6,045,552 A | 4/2000 | Zucherman et al. | |
| 6,048,342 A | 4/2000 | Zucherman et al. | |
| 6,048,345 A | 4/2000 | Berke et al. | |
| 6,066,154 A | 5/2000 | Reiley et al. | |
| 6,068,630 A | 5/2000 | Zucherman et al. | |
| 6,074,390 A | 6/2000 | Zucherman et al. | |
| 6,080,155 A | 6/2000 | Michelson | |
| 6,080,157 A | 6/2000 | Cathro et al. | |
| 6,090,112 A | 7/2000 | Zucherman et al. | |
| 6,096,038 A | 8/2000 | Michelson | |
| 6,102,928 A | 8/2000 | Bonutti | |
| D433,193 S | 10/2000 | Gaw et al. | |
| 6,132,464 A | 10/2000 | Martin et al. | |
| 6,149,642 A | 11/2000 | Gerhart et al. | |
| 6,149,652 A | 11/2000 | Zucherman et al. | |
| 6,152,926 A | 11/2000 | Zucherman et al. | |
| 6,156,038 A | 12/2000 | Zucherman et al. | |
| 6,159,215 A | 12/2000 | Urbahns et al. | |
| 6,179,873 B1 | 1/2001 | Zientek | |
| 6,183,471 B1 | 2/2001 | Zucherman et al. | |
| 6,190,387 B1 | 2/2001 | Zucherman et al. | |
| 6,225,048 B1 | 5/2001 | Soderberg-Naucler et al. | |
| 6,235,030 B1 | 5/2001 | Zucherman et al. | |
| 6,238,397 B1 | 5/2001 | Zucherman et al. | |
| 6,264,651 B1 | 7/2001 | Underwood et al. | |
| 6,264,656 B1 | 7/2001 | Michelson | |
| 6,267,763 B1 | 7/2001 | Castro | |
| 6,267,765 B1 | 7/2001 | Taylor et al. | |
| 6,270,498 B1 | 8/2001 | Michelson | |
| 6,280,444 B1 | 8/2001 | Zucherman et al. | |
| 6,312,431 B1 | 11/2001 | Asfora | |
| 6,328,730 B1 | 12/2001 | Harkrider, Jr. | |
| 6,332,882 B1 | 12/2001 | Zucherman et al. | |
| 6,332,883 B1 | 12/2001 | Zucherman et al. | |
| 6,336,930 B1 | 1/2002 | Stalcup et al. | |
| 6,348,053 B1 | 2/2002 | Cachia | |
| 6,364,883 B1 | 4/2002 | Santilli | |
| 6,371,989 B1 | 4/2002 | Chauvin et al. | |
| 6,375,682 B1 | 4/2002 | Fleischmann et al. | |
| 6,379,355 B1 | 4/2002 | Zucherman et al. | |
| 6,387,130 B1 | 5/2002 | Stone et al. | |
| 6,395,032 B1 | 5/2002 | Gauchet et al. | |
| 6,402,740 B1 | 6/2002 | Ellis et al. | |
| 6,402,750 B1 | 6/2002 | Atkinson et al. | |
| 6,402,784 B1 | 6/2002 | Wardlaw et al. | |
| 6,413,228 B1 | 7/2002 | Hung et al. | |

(56) References Cited

U.S. PATENT DOCUMENTS

| | | |
|---|---|---|
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |
| 6,464,682 B1 | 10/2002 | Snoke |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas et al. |
| 6,575,981 B1 | 6/2003 | Boyd et al. |
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps |
| 6,610,065 B1 | 8/2003 | Branch et al. |
| 6,610,091 B1 | 8/2003 | Reiley |
| 6,616,673 B1 | 9/2003 | Stone et al. |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | DiCarlo |
| 6,712,819 B2 | 3/2004 | Zucherman et al. |
| 6,716,215 B1 | 4/2004 | David et al. |
| 6,716,245 B2 | 4/2004 | Pasquet et al. |
| 6,726,690 B2 | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 6,976,988 B2 | 12/2005 | Ralph et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |

(56) References Cited

U.S. PATENT DOCUMENTS

| | | |
|---|---|---|
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |
| 7,811,324 B2 | 10/2010 | Arnin et al. |
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,687 B2 | 11/2010 | Harp |
| 7,837,688 B2 | 11/2010 | Boyer, II et al. |
| 7,837,700 B2 | 11/2010 | Harp |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 7,985,246 B2 | 7/2011 | Trieu et al. |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Solsberg et al. |
| 8,613,747 B2 | 12/2013 | Altarac et al. |
| 8,628,574 B2 | 1/2014 | Altarac et al. |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 2001/0031965 A1 | 10/2001 | Zucherman et al. |
| 2002/0022856 A1 | 2/2002 | Johnson |
| 2002/0029039 A1* | 3/2002 | Zucherman ........ A61B 17/7065 606/249 |
| 2002/0042607 A1 | 4/2002 | Palmer et al. |
| 2002/0116009 A1 | 8/2002 | Fraser |
| 2002/0143331 A1 | 10/2002 | Zucherman et al. |
| 2002/0151977 A1 | 10/2002 | Paes et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0105466 A1 | 6/2003 | Ralph et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markworth |
| 2004/0087947 A1 | 5/2004 | Lim et al. |
| 2004/0106997 A1 | 6/2004 | Lieberson |
| 2004/0106999 A1 | 6/2004 | Mathews |
| 2004/0148028 A1 | 7/2004 | Ferree |
| 2004/0167625 A1 | 8/2004 | Beyar et al. |
| 2004/0220568 A1 | 11/2004 | Zucherman et al. |
| 2004/0225295 A1 | 11/2004 | Zubok et al. |
| 2005/0021042 A1 | 1/2005 | Marnay |
| 2005/0049708 A1 | 3/2005 | Atkinson et al. |
| 2005/0075634 A1 | 4/2005 | Zucherman et al. |
| 2005/0090822 A1 | 4/2005 | DiPoto |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0209698 A1 | 9/2005 | Gordon |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0261768 A1 | 11/2005 | Trieu |
| 2005/0278036 A1 | 12/2005 | Leonard et al. |
| 2006/0030860 A1 | 2/2006 | Peterman |
| 2006/0036258 A1 | 2/2006 | Zucherman et al. |
| 2006/0064107 A1 | 3/2006 | Bertagnoli et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122458 A1 | 6/2006 | Bleich |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |

(56) References Cited

U.S. PATENT DOCUMENTS

| | | |
|---|---|---|
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191857 A1 | 8/2007 | Allard et al. |
| 2007/0191948 A1 | 8/2007 | Arnin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276390 A1 | 11/2007 | Solsberg |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0071380 A1 | 3/2008 | Sweeney |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1 | 5/2010 | Roebling et al. |

(56) References Cited

U.S. PATENT DOCUMENTS

| | | |
|---|---|---|
| 2010/0228092 A1 | 9/2010 | Ortiz et al. |
| 2010/0234889 A1 | 9/2010 | Hess |
| 2010/0262243 A1 | 10/2010 | Zucherman et al. |
| 2010/0280551 A1 | 11/2010 | Pool et al. |
| 2010/0305611 A1 | 12/2010 | Zucherman et al. |
| 2011/0245833 A1 | 10/2011 | Anderson |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0232552 A1 | 9/2012 | Morgenstern Lopez et al. |
| 2012/0303039 A1 | 11/2012 | Chin et al. |
| 2012/0330359 A1 | 12/2012 | Kim |
| 2013/0012998 A1 | 1/2013 | Altarac et al. |
| 2013/0072985 A1 | 3/2013 | Kim |
| 2013/0150886 A1 | 6/2013 | Altarac et al. |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi et al. |
| 2013/0289622 A1 | 10/2013 | Kim |
| 2014/0081332 A1 | 3/2014 | Altarac et al. |
| 2014/0214082 A1 | 7/2014 | Reglos et al. |
| 2014/0228884 A1 | 8/2014 | Altarac et al. |
| 2014/0275992 A1 | 9/2014 | Choi et al. |
| 2015/0150598 A1 | 6/2015 | Tebbe et al. |
| 2015/0150604 A1 | 6/2015 | Kim |
| 2015/0164560 A1 | 6/2015 | Altarac et al. |
| 2015/0374415 A1 | 12/2015 | Kim |
| 2016/0045232 A1 | 2/2016 | Altarac et al. |
| 2016/0066963 A1 | 3/2016 | Kim |
| 2016/0135853 A1 | 5/2016 | Altarac et al. |
| 2016/0248222 A1 | 8/2016 | Miyata |
| 2016/0317193 A1 | 11/2016 | Kim et al. |
| 2017/0071588 A1 | 3/2017 | Choi |
| 2017/0128110 A1 | 5/2017 | Altarac et al. |
| 2017/0156763 A1 | 6/2017 | Altarac et al. |
| 2017/0245883 A1 | 8/2017 | Tebbe et al. |
| 2017/0258501 A1 | 9/2017 | Altarac et al. |
| 2017/0273722 A1 | 9/2017 | Altarac et al. |
| 2018/0028130 A1 | 2/2018 | Choi |

FOREIGN PATENT DOCUMENTS

| | | |
|---|---|---|
| CN | 101897603 | 12/2010 |
| DE | 69507480 | 9/1999 |
| EP | 322334 | 6/1989 |
| EP | 0767636 | 4/1997 |
| EP | 0768843 B1 | 4/1997 |
| EP | 0959792 B1 | 12/1999 |
| EP | 1027004 A1 | 8/2000 |
| EP | 1030615 A1 | 8/2000 |
| EP | 1138268 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 1861046 A2 | 12/2007 |
| FR | 2681525 | 3/1993 |
| FR | 2722980 A1 | 2/1996 |
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO-9404088 A1 | 3/1994 |
| WO | WO-9426192 A1 | 11/1994 |
| WO | WO-9525485 A1 | 9/1995 |
| WO | WO-9531158 A1 | 11/1995 |
| WO | WO-9600049 A1 | 1/1996 |
| WO | WO-9829047 A1 | 7/1998 |
| WO | WO-9921500 A1 | 5/1999 |
| WO | WO-9921501 A1 | 5/1999 |
| WO | WO-9942051 A1 | 8/1999 |
| WO | WO-0013619 A1 | 3/2000 |
| WO | WO-0044319 A1 | 8/2000 |
| WO | WO-0044321 A2 | 8/2000 |
| WO | WO-0128442 A1 | 4/2001 |
| WO | WO-0191657 A1 | 12/2001 |
| WO | WO-0191658 A1 | 12/2001 |
| WO | WO-0203882 A2 | 1/2002 |
| WO | WO-0207623 A1 | 1/2002 |
| WO | WO-0207624 A1 | 1/2002 |
| WO | WO-02051326 A1 | 7/2002 |
| WO | WO-02067793 A2 | 9/2002 |
| WO | WO-02071960 A1 | 9/2002 |
| WO | WO-02076336 A2 | 10/2002 |
| WO | WO-03007791 A2 | 1/2003 |
| WO | WO-03007829 A1 | 1/2003 |
| WO | WO-03008016 A2 | 1/2003 |
| WO | WO-03015646 A2 | 2/2003 |
| WO | WO-03024298 A2 | 3/2003 |
| WO | WO-03045262 A2 | 6/2003 |
| WO | WO-03099147 A1 | 12/2003 |
| WO | WO-03101350 A1 | 12/2003 |
| WO | WO-04073533 A1 | 9/2004 |
| WO | WO-04110300 A2 | 12/2004 |
| WO | WO-05009300 A1 | 2/2005 |
| WO | WO-05013839 A2 | 2/2005 |
| WO | WO-05025461 A2 | 3/2005 |
| WO | WO-05041799 A1 | 5/2005 |
| WO | WO-05044152 A1 | 5/2005 |
| WO | WO-05055868 A2 | 6/2005 |
| WO | WO-05079672 A2 | 9/2005 |
| WO | WO-2005086776 A2 | 9/2005 |
| WO | WO-05115261 A1 | 12/2005 |
| WO | WO-06033659 A2 | 3/2006 |
| WO | WO-06034423 A2 | 3/2006 |
| WO | WO-06039243 | 4/2006 |
| WO | WO-06039260 A2 | 4/2006 |
| WO | WO-06045094 A2 | 4/2006 |
| WO | WO-2006045094 A2 | 4/2006 |
| WO | WO-06063047 A2 | 6/2006 |
| WO | WO-06065774 A1 | 6/2006 |
| WO | WO-2006063047 A2 | 6/2006 |
| WO | WO-2006064356 A1 | 6/2006 |
| WO | WO-2006089085 A2 | 8/2006 |
| WO | WO-06102269 A2 | 9/2006 |
| WO | WO-06102428 A1 | 9/2006 |
| WO | WO-06102485 A2 | 9/2006 |
| WO | WO-06107539 A1 | 10/2006 |
| WO | WO-06110462 A2 | 10/2006 |
| WO | WO-06110464 A2 | 10/2006 |
| WO | WO-06110767 A1 | 10/2006 |
| WO | WO-06113080 A2 | 10/2006 |
| WO | WO-06113406 A2 | 10/2006 |
| WO | WO-06113814 A2 | 10/2006 |
| WO | WO-06118945 A1 | 11/2006 |
| WO | WO-06119235 A1 | 11/2006 |
| WO | WO-06119236 A2 | 11/2006 |
| WO | WO-06135511 A1 | 12/2006 |
| WO | WO-07015028 A1 | 2/2007 |
| WO | WO-07035120 A1 | 3/2007 |
| WO | WO-07075375 A2 | 7/2007 |
| WO | WO-07075788 A2 | 7/2007 |
| WO | WO-07075791 A2 | 7/2007 |
| WO | WO-07089605 A2 | 8/2007 |
| WO | WO-07089905 A2 | 8/2007 |
| WO | WO-07089975 A1 | 8/2007 |
| WO | WO-07097735 A2 | 8/2007 |
| WO | WO-07109402 A2 | 9/2007 |
| WO | WO-07110604 A1 | 10/2007 |
| WO | WO-07111795 A1 | 10/2007 |
| WO | WO-07111979 A2 | 10/2007 |
| WO | WO-07111999 A2 | 10/2007 |
| WO | WO-07117882 A1 | 10/2007 |
| WO | WO-07121070 A2 | 10/2007 |
| WO | WO-07127550 A2 | 11/2007 |
| WO | WO-07127588 A1 | 11/2007 |

(56) References Cited

FOREIGN PATENT DOCUMENTS

| WO | WO-07127677 A1 | 11/2007 |
|---|---|---|
| WO | WO-07127689 A2 | 11/2007 |
| WO | WO-07127694 A2 | 11/2007 |
| WO | WO-07127734 A2 | 11/2007 |
| WO | WO-07127736 A2 | 11/2007 |
| WO | WO-07131165 A2 | 11/2007 |
| WO | WO-07134113 A2 | 11/2007 |
| WO | WO-2008009049 A1 | 1/2008 |
| WO | WO-08048645 A2 | 4/2008 |
| WO | WO-2008057506 A2 | 5/2008 |
| WO | WO-2008130564 A1 | 10/2008 |
| WO | WO-2009014728 A2 | 1/2009 |
| WO | WO-2009033093 A1 | 3/2009 |
| WO | WO-2009086010 A2 | 7/2009 |
| WO | WO-2009091922 A2 | 7/2009 |
| WO | WO-2009094463 A2 | 7/2009 |
| WO | WO-2009114479 A2 | 9/2009 |
| WO | WO-2011084477 A2 | 7/2011 |
| WO | WO-2015171814 A1 | 11/2015 |

OTHER PUBLICATIONS

International Search Report and Written Opinion; Application No. PCT/US2005/044256; dated Jul. 28, 2006, 7 pages.
International Search Report and Written Opinion; Application No. PCT/US2006/047824; dated Oct. 16, 2008, 17 pages.
International Search Report and Written Opinion; Application No. PCT/US2006/048611; dated Oct. 14, 2008; 10 pages.
International Search Report and Written Opinion; Application No. PCT/US2006/048614; dated Feb. 3, 2006; 23 pages.
International Search Report and Written Opinion; Application No. PCT/US2007/022171; dated Apr. 15, 2008, 9 pages.
International Search Report and Written Opinion; Application No. PCT/US2007/023312; dated May 22, 2008, 14 pages.
International Search Report and Written Opinion; Application No. PCT/US2008/004901; dated Aug. 19, 2008, 7 pages.
International Search Report and Written Opinion; Application No. PCT/US2008/008382; dated Mar. 2, 2009, 13 pages.
International Search Report and Written Opinion; Application No. PCT/US2008/008983; dated Feb. 23, 2009, 7 pages.
International Search Report and Written Opinion; Application No. PCT/US2008/075487; dated Dec. 31, 2008, 7 pages.
International Search Report and Written Opinion; Application No. PCT/US2008/087527; dated Jul. 30, 2009, 10 pages.
International Search Report and Written Opinion; Application No. PCT/US2009/031150; dated Aug. 28, 2009, 6 pages.
International Search Report and Written Opinion; Application No. PCT/US2009/036561; dated Sep. 17, 2009, 12 pages.
Minns, R.J., et al., "Preliminary Design and Experimental Studies of a Noval Soft Implant for Correcting Sagittal Plane Instability in the Lumbar Spine," (1997) Spine, 22(16): 1819-1827.
Swan, Colby, "Preliminary Design and Experimental Studies of a Novel Soft Implant for Correcting Sogittal Plane Instability in the Lumbar Spine," Spine, 1997, 22(16), 1826-1827.
Australia Exam Report for Application No. AU2006329867, Applicant: The Board of Trustees of Leland Stanford Junior University; dated Jan. 27, 2012, 2 pages.
Canada Exam Report for Application No. CA2634251, Applicant: The Board of Trustees of Leland Stanford Junior University; dated Dec. 3, 2013, 2 pages.

Supplementary European Search Report for Application No. EP06845480; Applicant: VertiFlex, Inc.; Date of Completion: Aug. 14, 2012, 9 pages.
Supplementary European Search Report for Application No. EP13184922.6; Applicant: VertiFlex, Inc.; dated Oct. 30, 2013, 8 pages.
International Search Report and Written Opinion; Application No. PCT/US2010/060498; dated Aug. 25, 2011, 17 pages.
International Search Report and Written Opinion; Application No. PCT/US2009/031710; dated Sep. 1, 2009, 10 pages.
Australia Exam Report for Application No. AU2013273815, Applicant: The Board of Trustees of Leland Stanford Junior University; dated Apr. 17, 2015, 3 pages.
International Search Report, counterpart PCT Application PCT/US2013/038534, Applicant: Vertiflex, Inc., dated Aug. 7, 2013, 16 pages.
McCulloch, John A., Young, Paul H., "Essentials of Spinal Microsurgery," 1998, pp. 453-485. Lippincott-Raven Publishers, Philadelphia, PA (37 pages total).
Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).
Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).
Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).
Decision on Petition in U.S. Appl. No. 60/592,099, dated May 4, 2005.
Vaccaro, Alexander J. et al., MasterCases Spine Surgery, 2001, pp. 100-107. Thieme Medical Publishers, Inc., NY. (10 pages total).
Fast, Avital et al., "Surgical Treatment of Lumbar Spinal Stenosis in the Elderly," Arch Phys. Med Rehabil., Mar. 1985, pp. 149-151, vol. 66.
Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.
International Search Report and Written Opinion; Application No. PCT/US2009/029537; Applicant: Vertiflex, Inc. dated Aug. 3, 2015, 14 pages.
ASNR Neuroradiology Patient Information website, Brain and Spine Imaging: A Patient's Guide to Neuroradiology; Myelography; http://www.asnr.org/patientinfo/procedures/myelography.shtml#sthash.sX1DOxWq.dpbs, Copyright 2012-2013.
Australia Exam Report for Application No. AU2014203394, Applicant: VertiFlex, Inc., dated Mar. 15, 2016, 2 pages.
European Further Exam Report for Application No. EP09702116.6; Applicant: VertiFlex, Inc.; dated Jul. 4, 2016, 4 pages.
European Examination Report for Application No. 08794704.0; Applicant: Vertiflex, Inc.; dated Apr. 5, 2017, 6 pages.
European Examination Report for Application No. 08799267.3; Applicant: Vertiflex, Inc.; dated Sep. 5, 2017, 4 pages.
First Examination Report in European Patent Application No. 08780034.8, dated Jan. 16, 2017, 5 pages.
Further Examination Report in European Patent Application No. 07861426.0, dated Oct. 4, 2017, 4 pages.
U.S. Appl. No. 15/831,201 by Kim, filed Dec. 4, 2017.
U.S. Appl. No. 15/864,235 by Altarac et al., filed Jan. 8, 2018.
U.S. Appl. No. 15/966,287 by Altarac et al., filed Apr. 30, 2018.

* cited by examiner

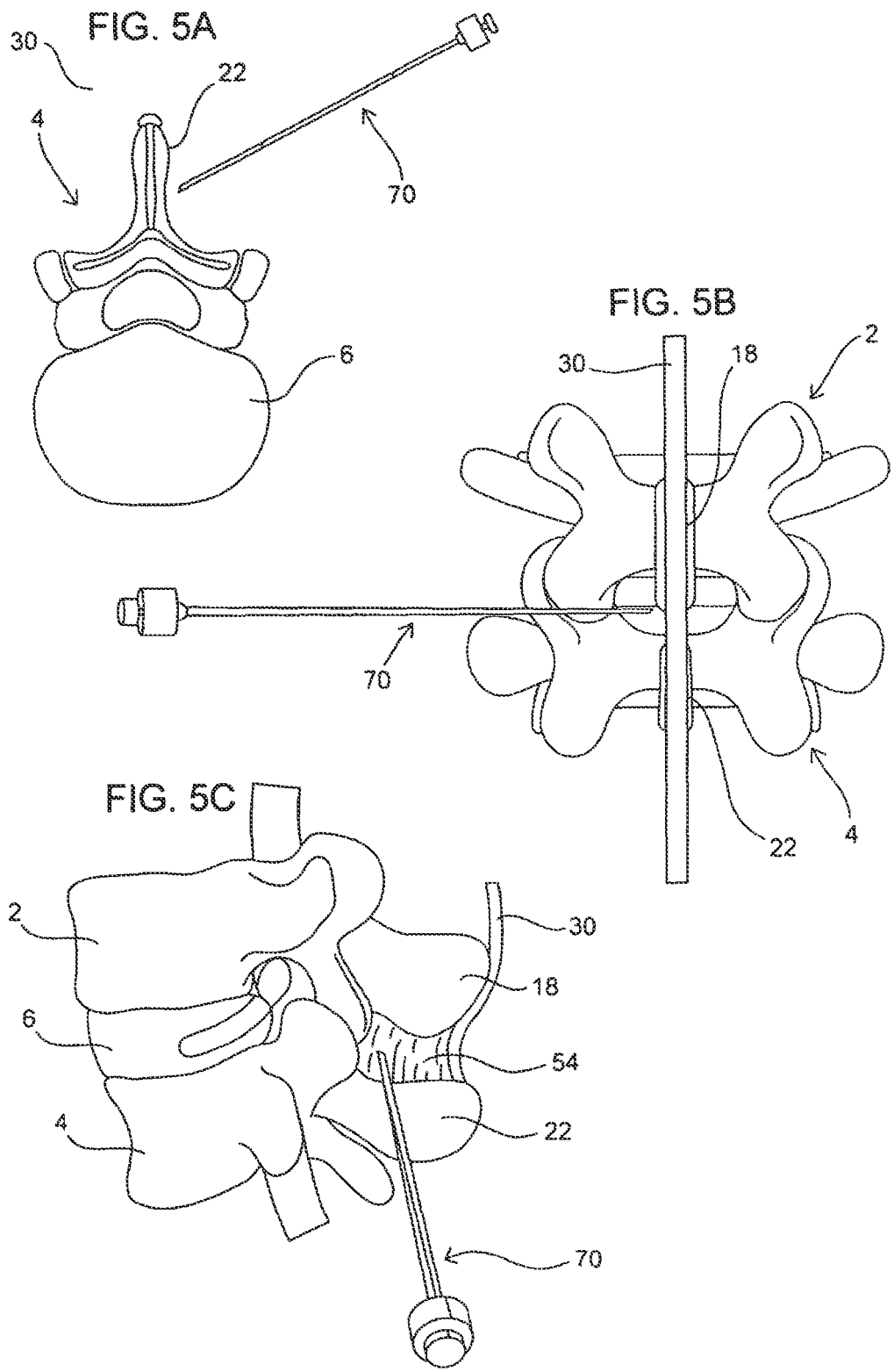

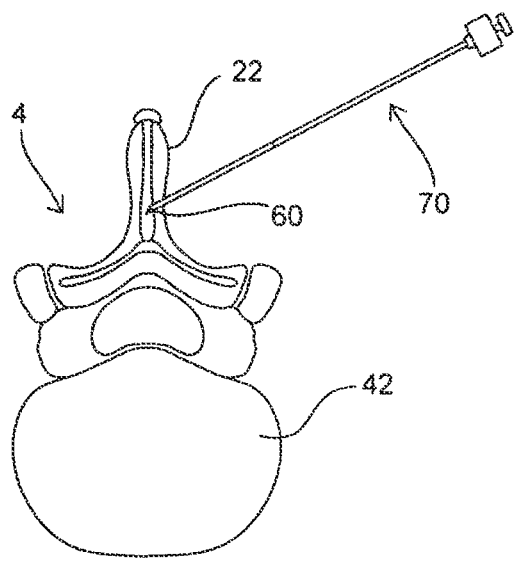
FIG. 6A
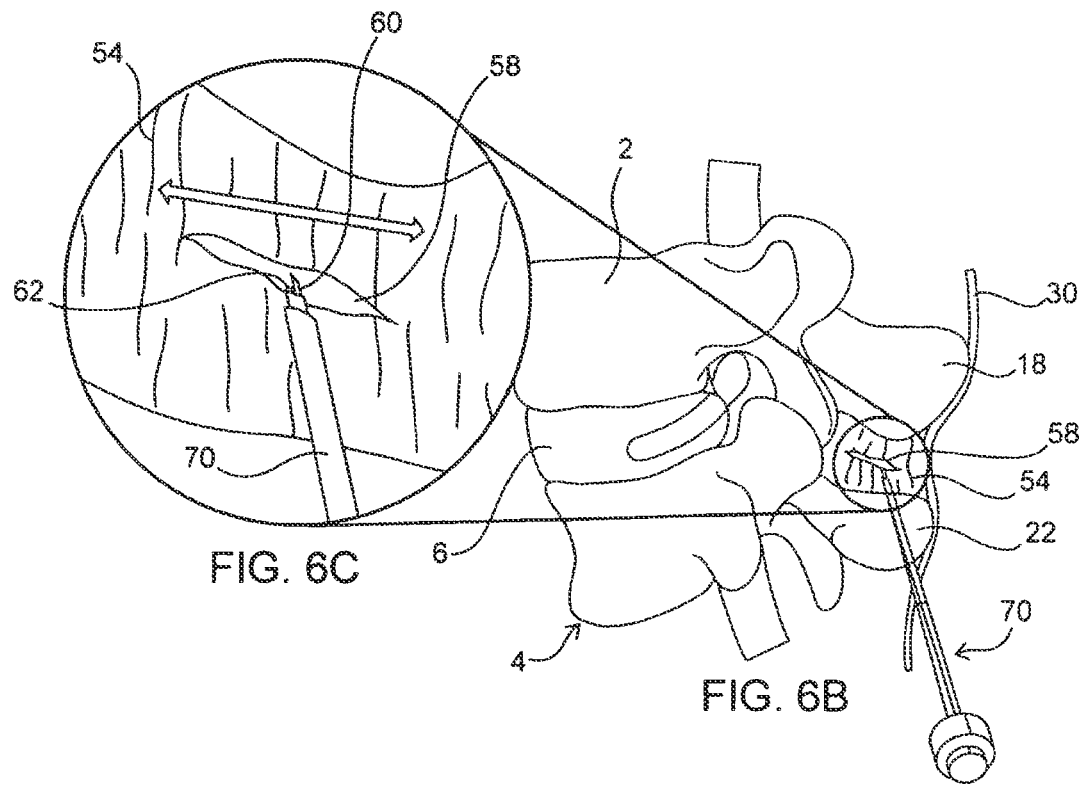
FIG. 6C
FIG. 6B

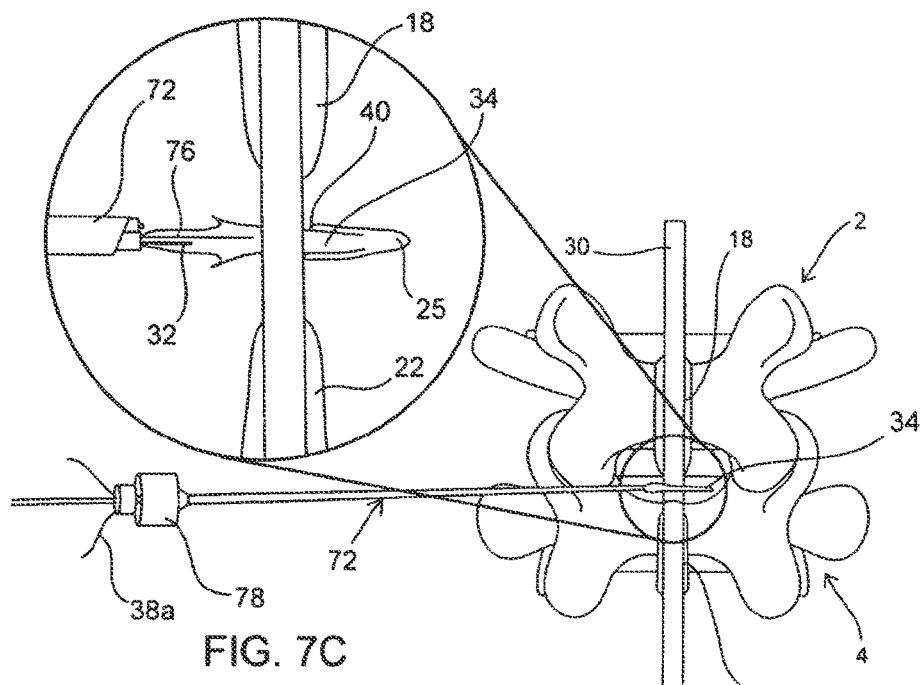
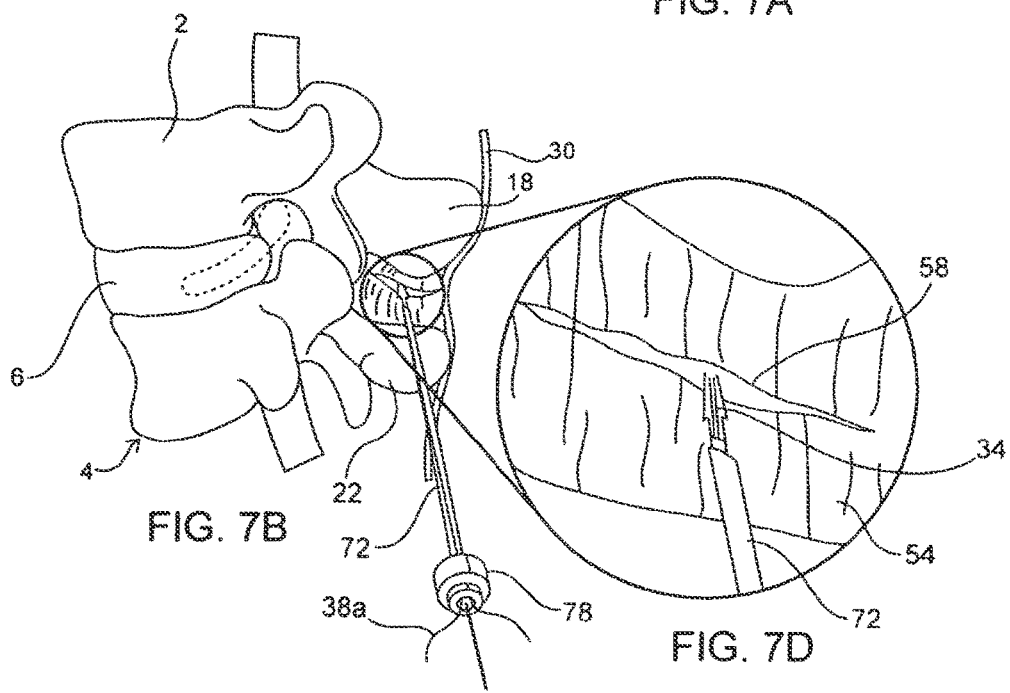

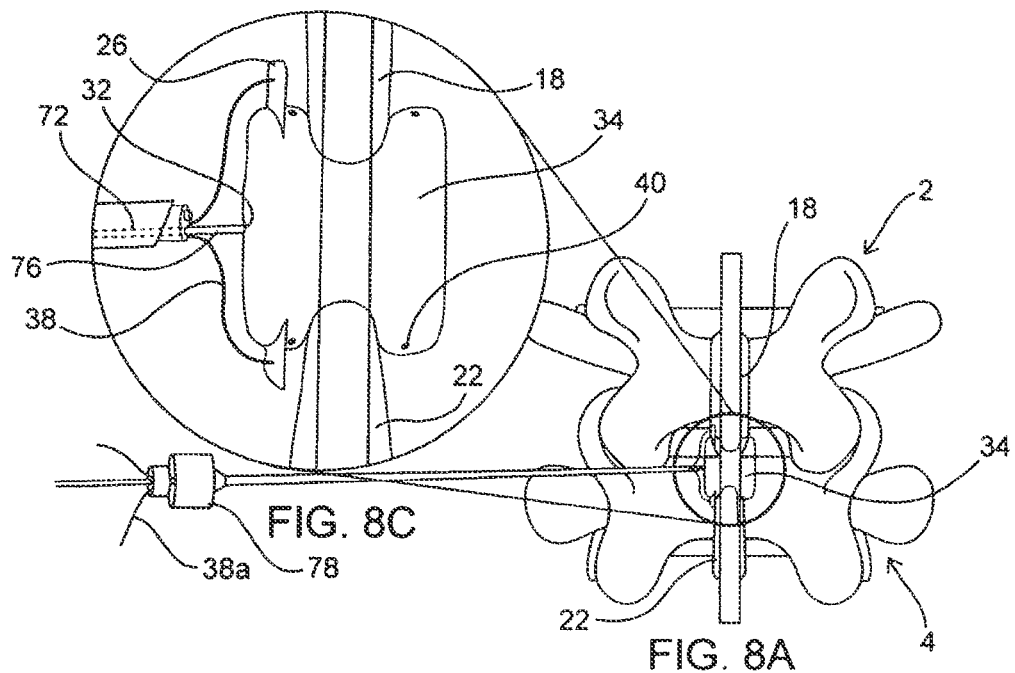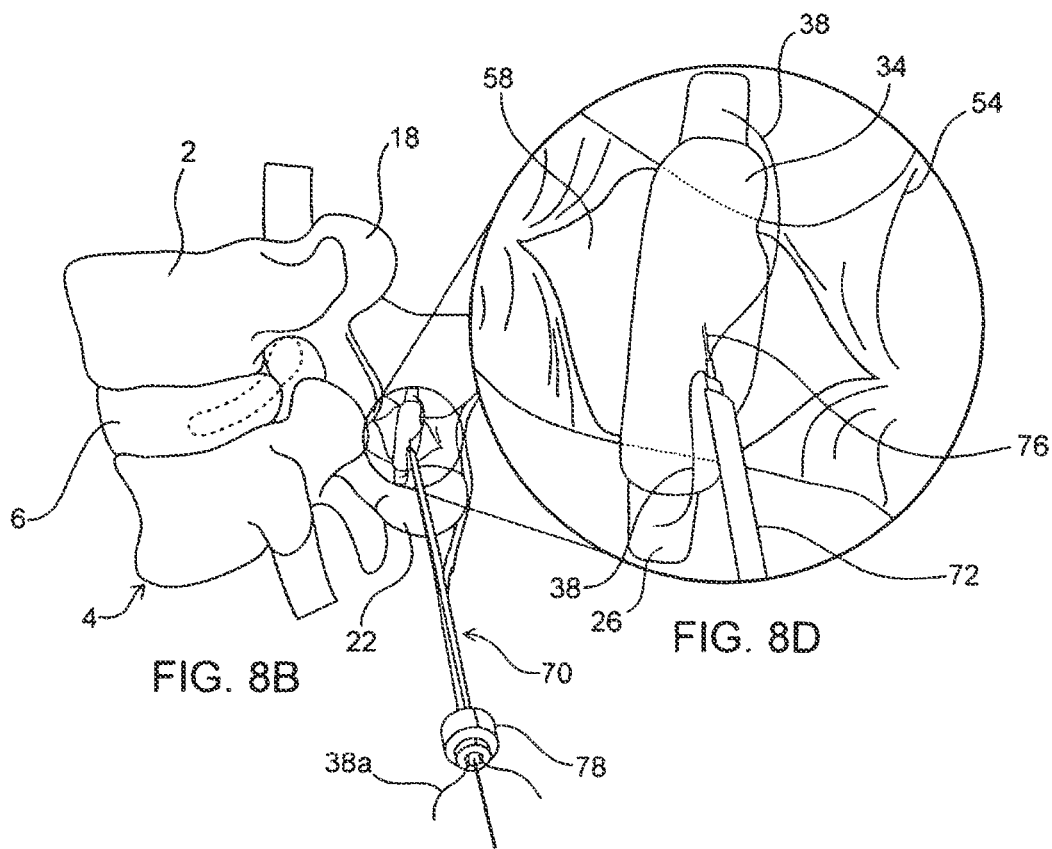

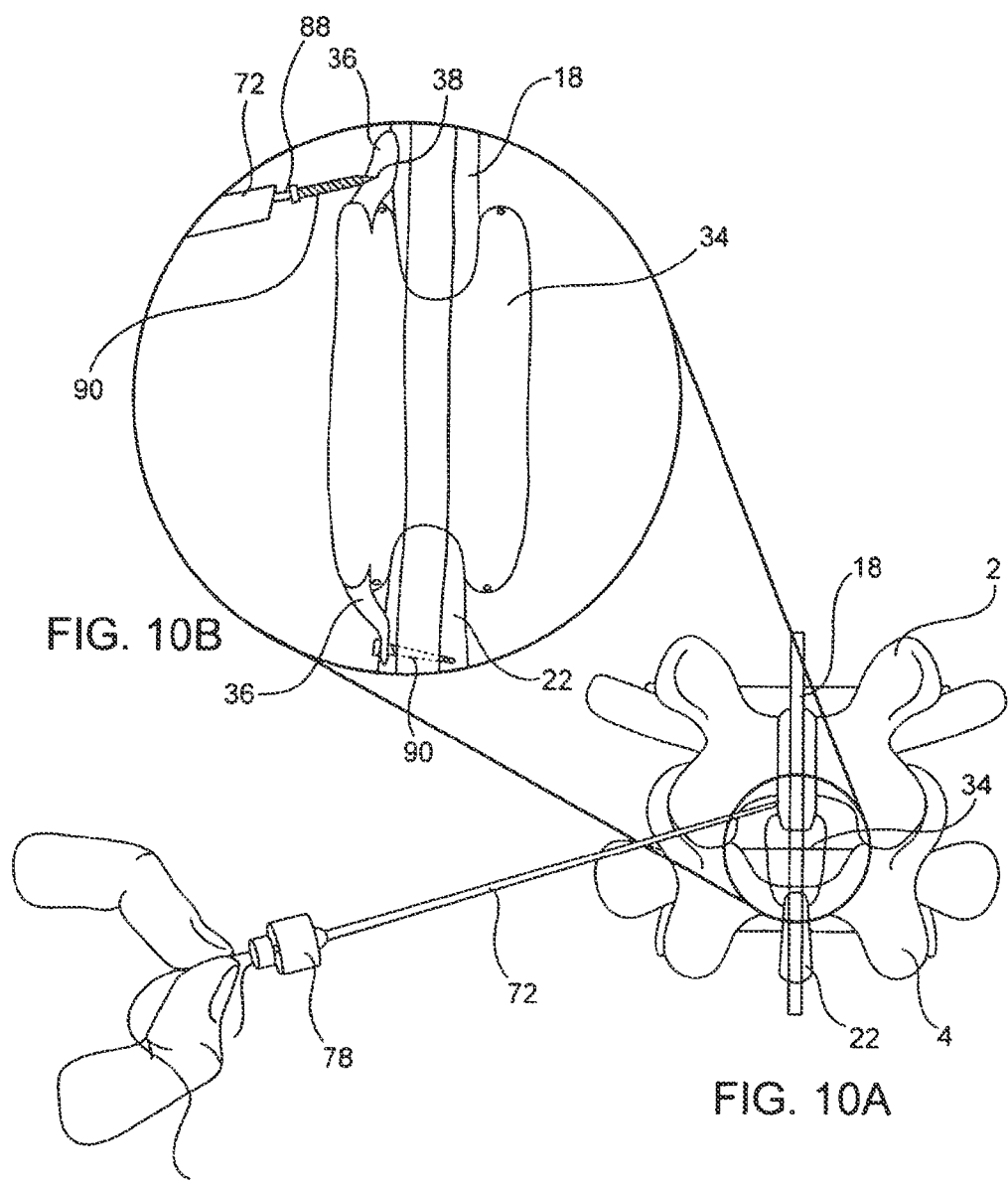

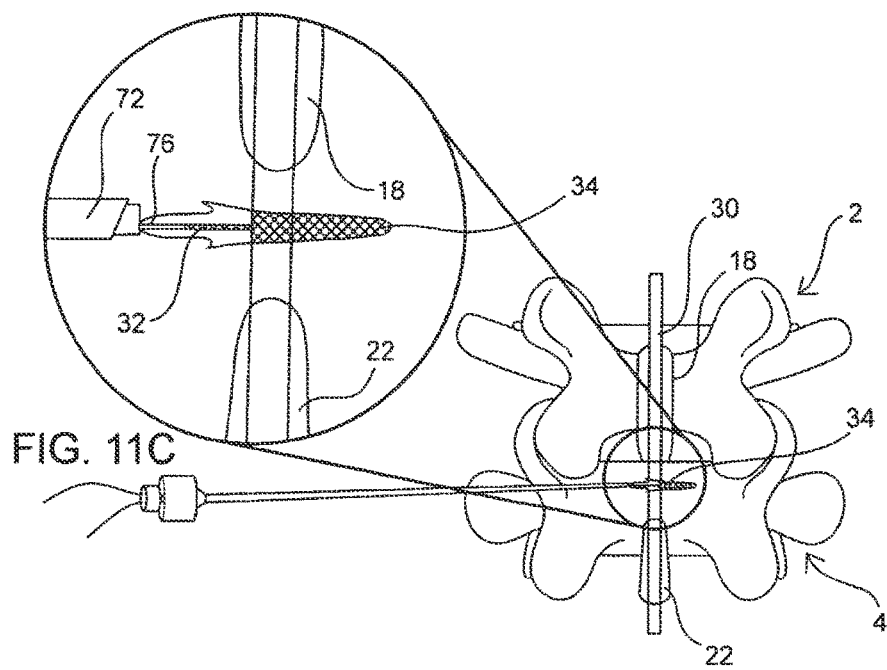
FIG. 11C
FIG. 11A
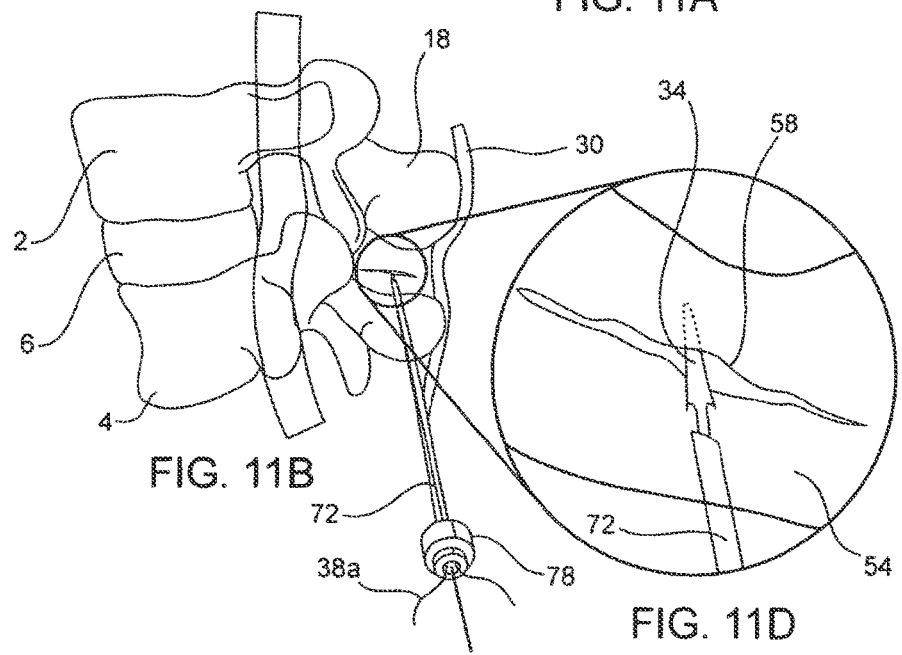
FIG. 11B
FIG. 11D

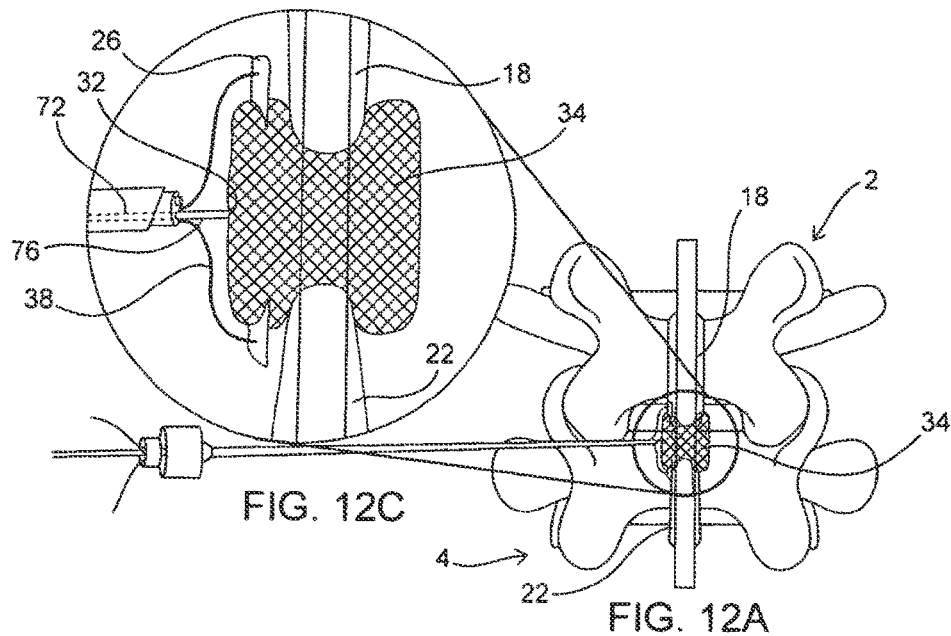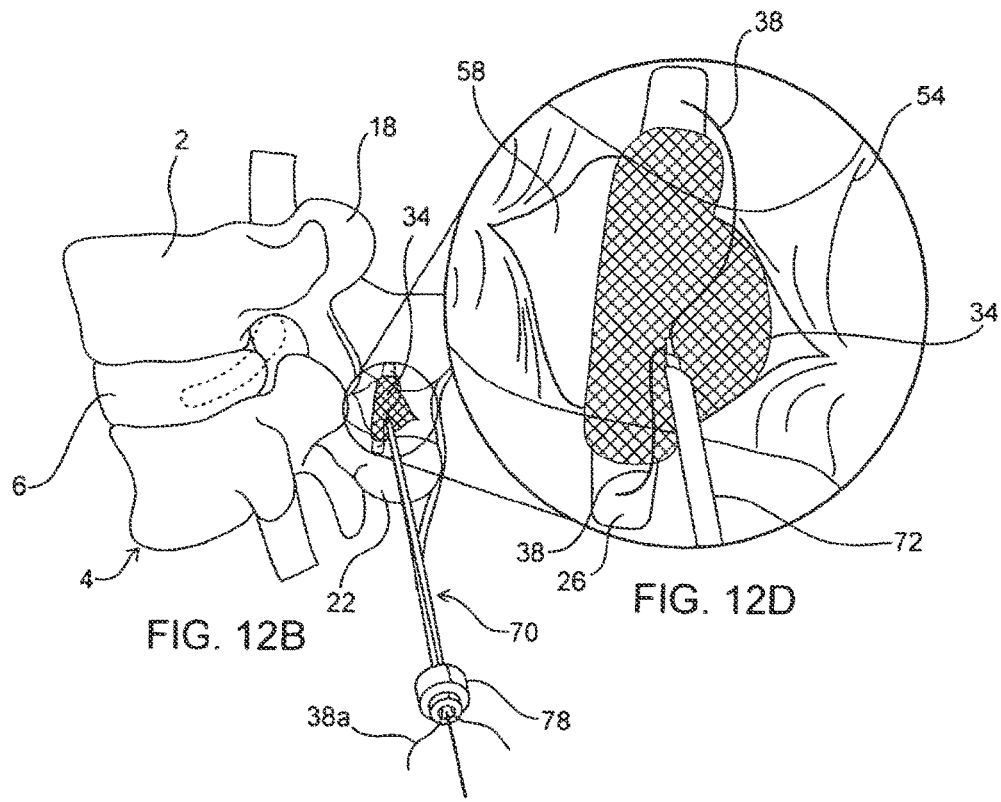

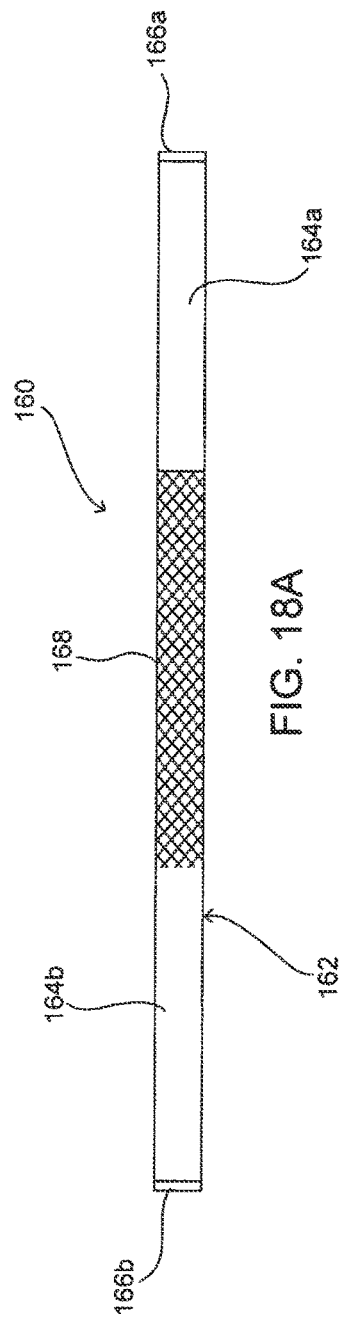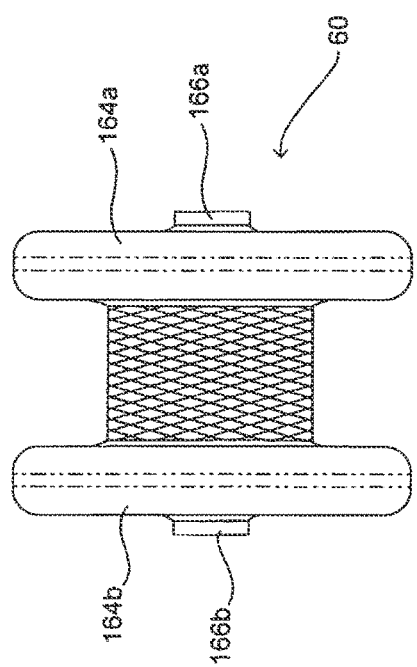

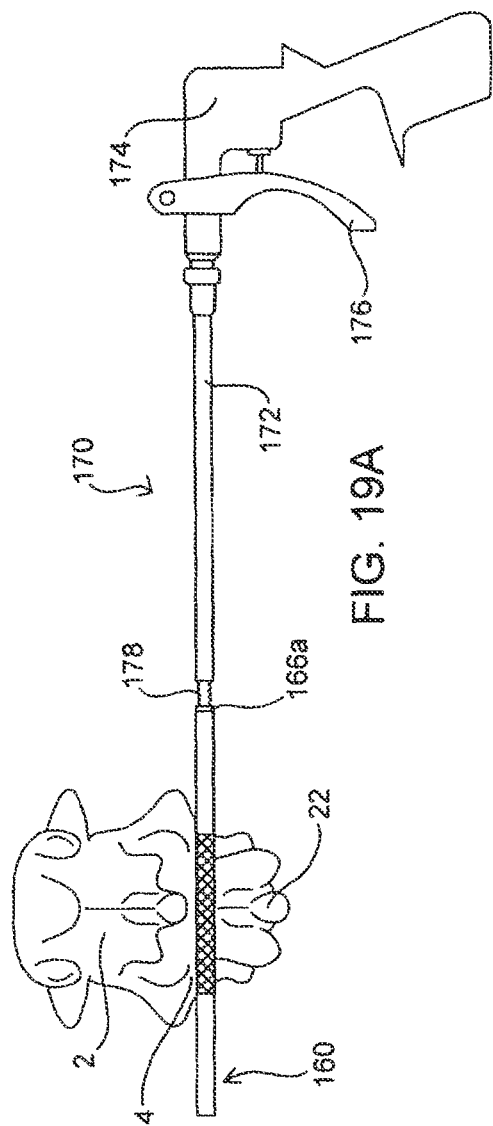
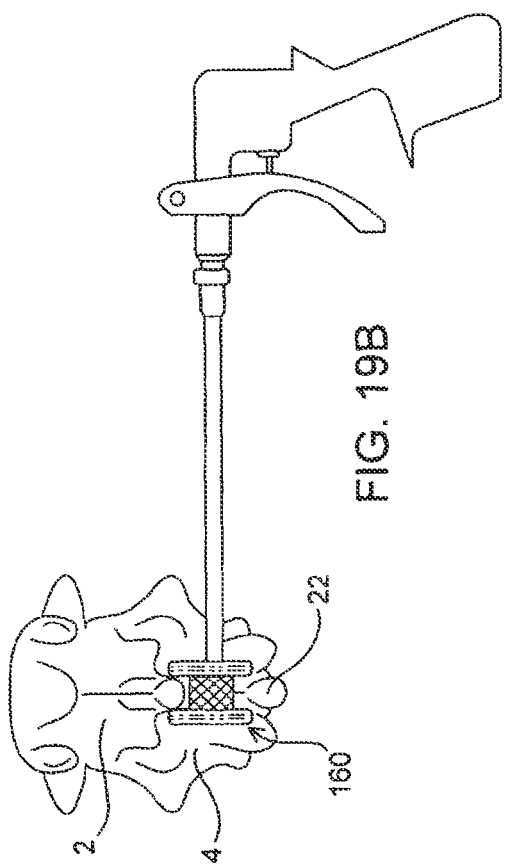
FIG. 19A
FIG. 19B

FIG. 28A"

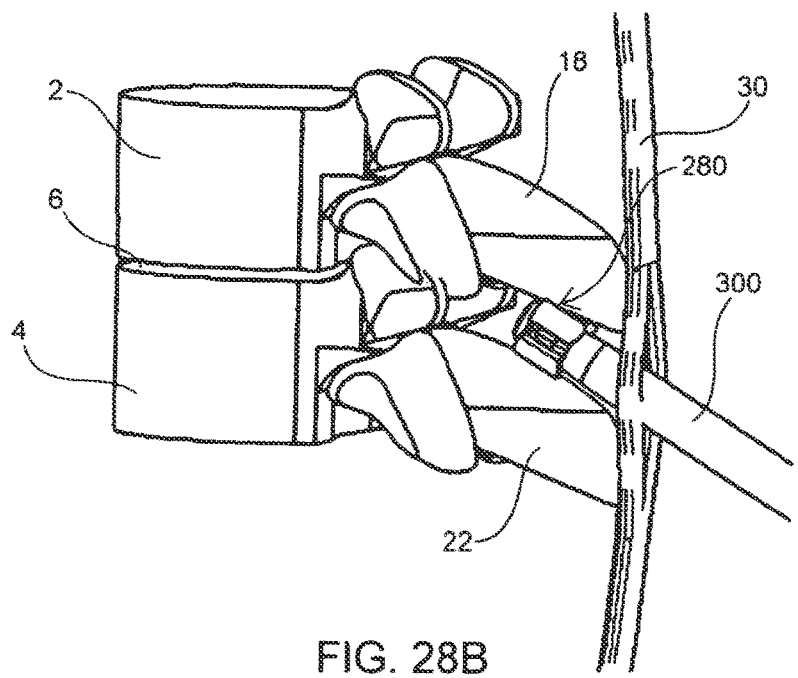
FIG. 28B
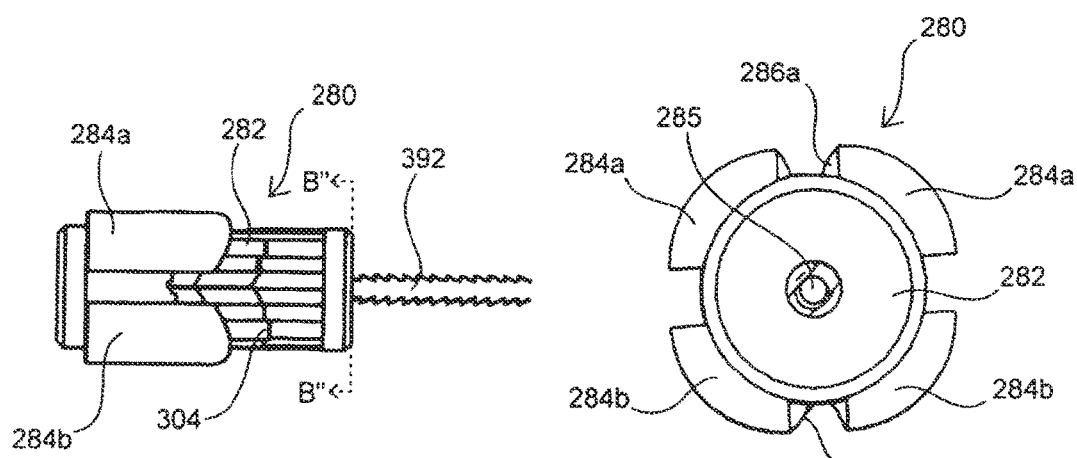
FIG. 28B'  FIG. 28B"

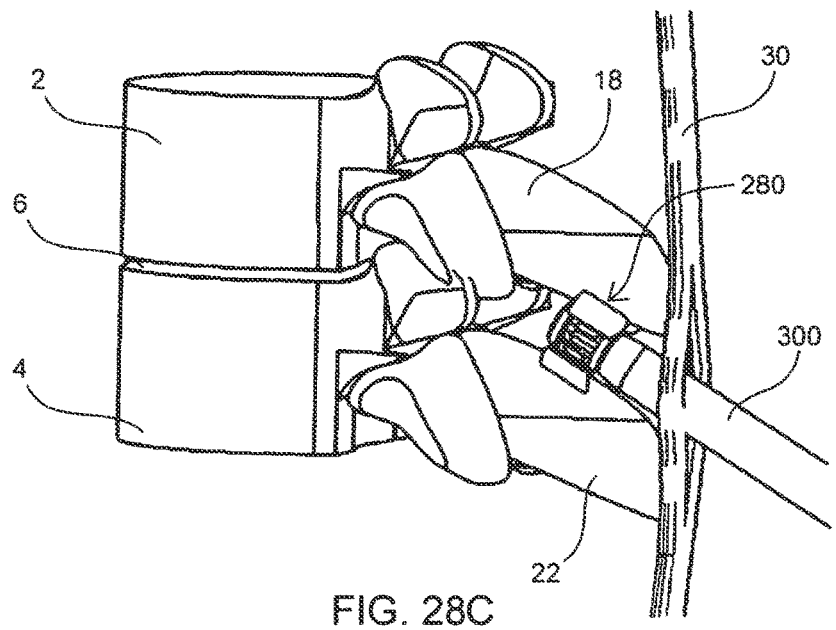
FIG. 28C
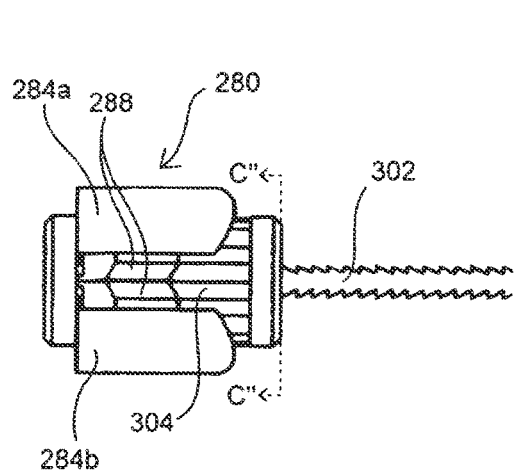
FIG. 28C'
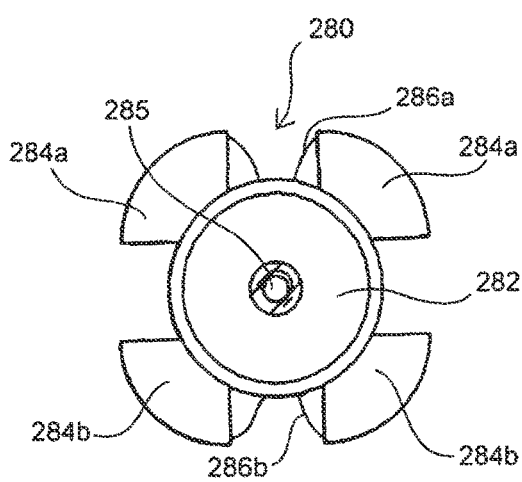
FIG. 28C"

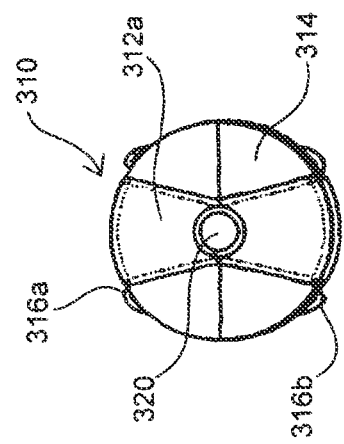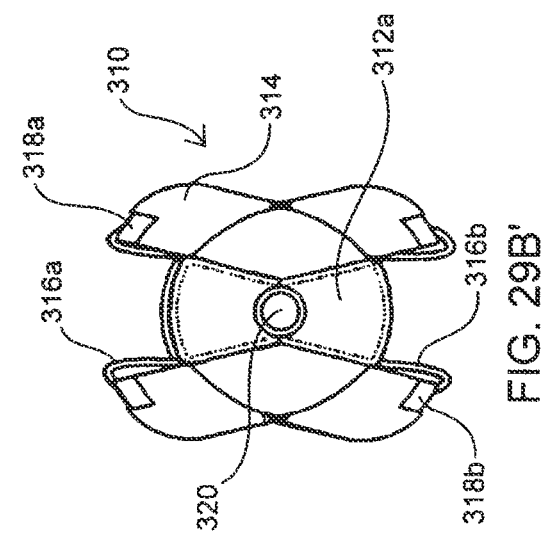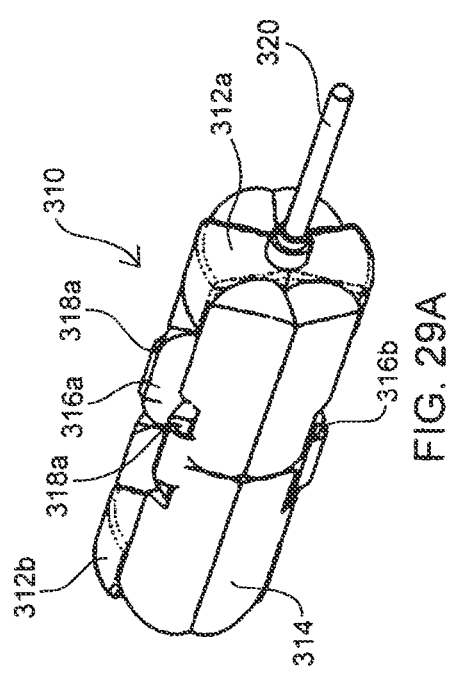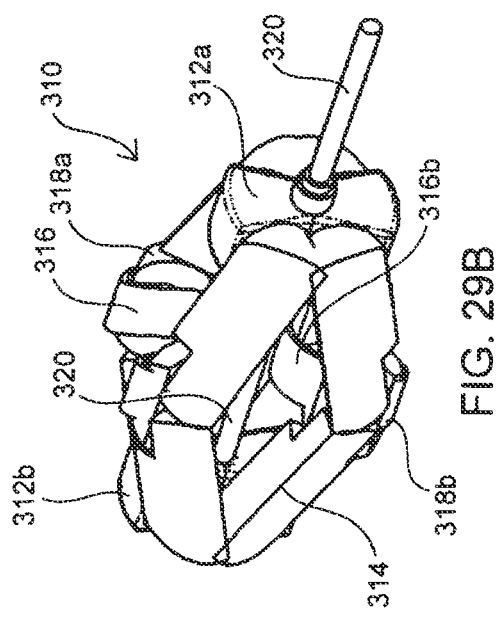
FIG. 29A'  FIG. 29B'
FIG. 29A  FIG. 29B

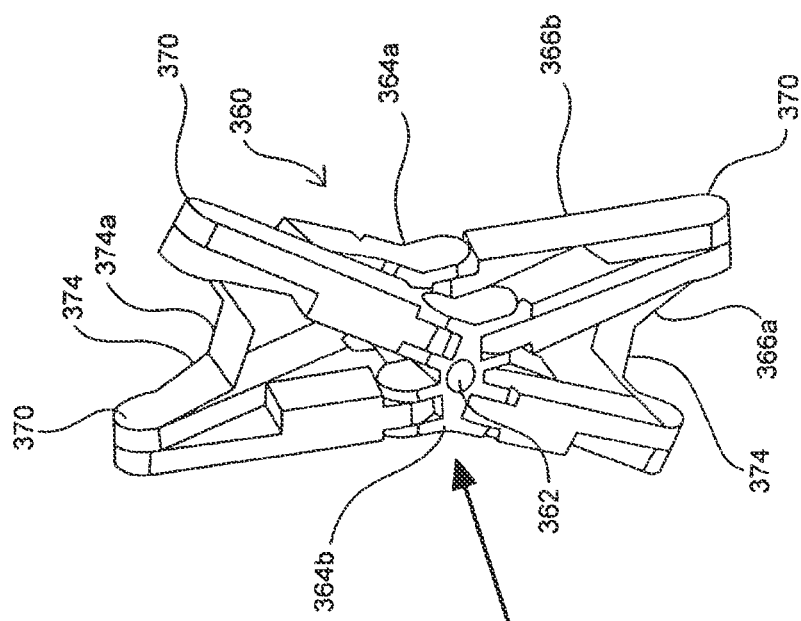
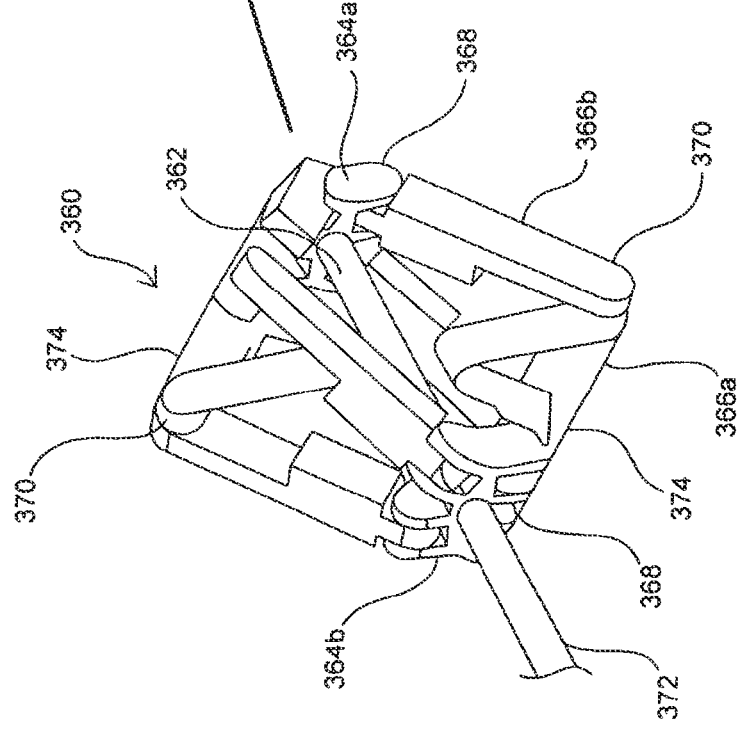
FIG. 31A
FIG. 31B

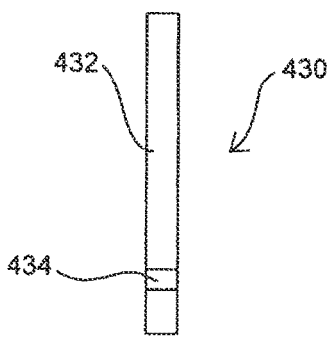
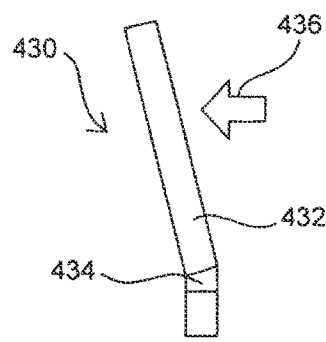
FIG. 34A
FIG. 34B
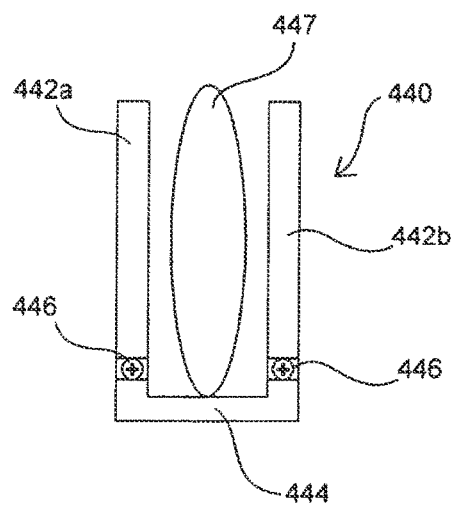
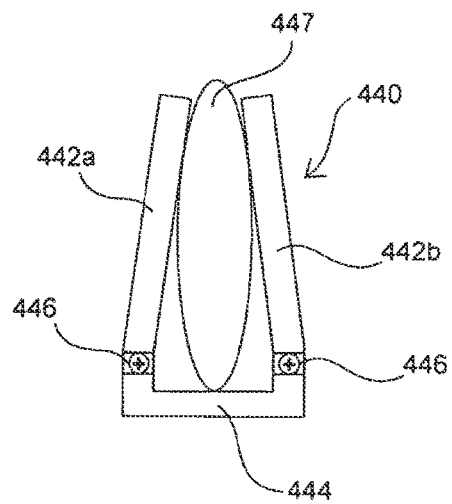
FIG. 35A
FIG. 35B

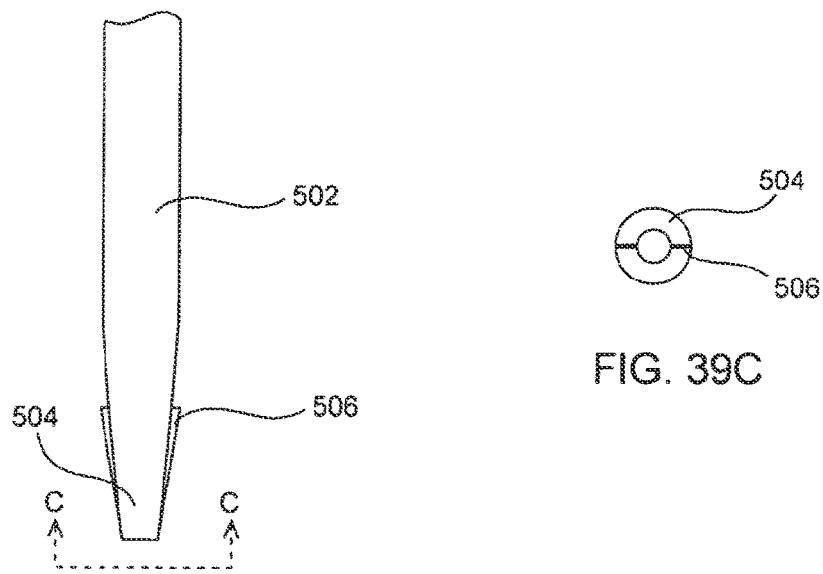
FIG. 39B
FIG. 39C
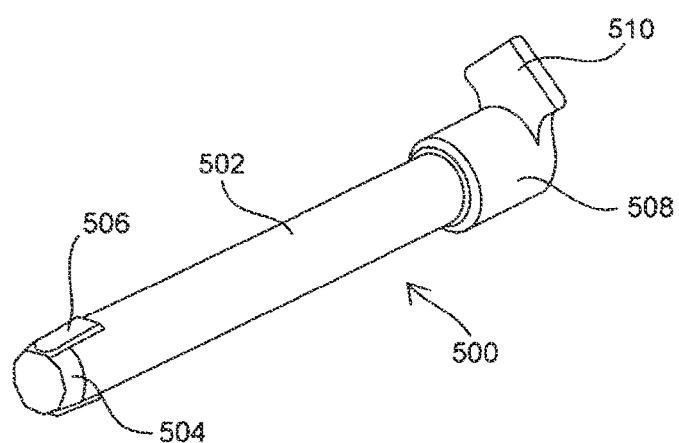
FIG. 39A

SYSTEMS AND METHODS FOR POSTERIOR DYNAMIC STABILIZATION OF THE SPINE

CROSS-REFERENCE TO RELATED APPLICATIONS

This application is a continuation of U.S. patent application Ser. No. 13/442,751, filed on Apr. 9, 2012 and entitled "SYSTEMS AND METHODS FOR POSTERIOR DYNAMIC STABILIZATION OF THE SPINE," now granted U.S. Pat. No. 9,039,742, which is a continuation of U.S. patent application Ser. No. 11/314,712, filed on Dec. 20, 2005 and entitled "SYSTEMS AND METHODS FOR POSTERIOR DYNAMIC STABILIZATION OF THE SPINE," now granted U.S. Pat. No. 8,152,837, which is a continuation-in-part of U.S. patent application Ser. No. 11/190,496, filed on Jul. 26, 2005 and entitled "SYSTEMS AND METHODS FOR POSTERIOR DYNAMIC STABILIZATION OF THE SPINE," now granted U.S. Pat. No. 8,409,282, which is a continuation-in-part of U.S. patent application Ser. No. 11/079,006, filed on Mar. 10, 2005 and entitled "SYSTEMS AND METHODS FOR POSTERIOR DYNAMIC STABILIZATION OF THE SPINE" now U.S. Pat. No. 8,012,207, which is a continuation-in-part of U.S. patent application Ser. No. 11/052,002, filed on Feb. 4, 2005 and entitled "SYSTEMS AND METHODS FOR POSTERIOR DYNAMIC STABILIZATION OF THE SPINE," now U.S. Pat. No. 8,317,864, which is a continuation-in-part of U.S. patent application Ser. No. 11/006,502, filed on Dec. 6, 2004 and entitled "SYSTEMS AND METHODS FOR POSTERIOR DYNAMIC STABILIZATION OF THE SPINE," now granted U.S. Pat. No. 8,123,807, which is a continuation-in-part of U.S. patent application Ser. No. 10/970,843, filed on Oct. 20, 2004 and entitled "SYSTEMS AND METHODS FOR POSTERIOR DYNAMIC STABILIZATION OF THE SPINE," now granted U.S. Pat. No. 8,167,944, all of which are hereby incorporated by reference in their entireties.

FIELD OF THE INVENTION

The present invention is directed towards the treatment of spinal disorders and pain. More particularly, the present invention is directed to systems and methods of treating the spine, which eliminate pain and enable spinal motion, which effectively mimics that of a normally functioning spine.

BACKGROUND OF THE INVENTION

FIG. 1 illustrates a portion of the human spine having a superior vertebra 2 and an inferior vertebra 4, with an intervertebral disc 6 located in between the two vertebral bodies. The superior vertebra 2 has superior facet joints 8a and 8b, inferior facet joints 10a and 10b, and spinous process 18. Pedicles 3a and 3b interconnect the respective superior facet joints 8a, 8b to the vertebral body 2. Extending laterally from superior facet joints 8a, 8b are transverse processes 7a and 7b, respectively. Extending between each inferior facet joints 10a and 10b and the spinous process 18 are laminal zones 5a and 5b, respectively. Similarly, inferior vertebra 4 has superior facet joints 12a and 12b, superior pedicles 9a and 9b, transverse processes 11a and 11b, inferior facet joints 14a and 14b, laminal zones 15a and 15b, and spinous process 22.

The superior vertebra with its inferior facets, the inferior vertebra with its superior facet joints, the intervertebral disc, and seven spinal ligaments (not shown) extending between the superior and inferior vertebrae together comprise a spinal motion segment or functional spine. unit. Each spinal motion segment enables motion along three orthogonal axes, both in rotation and in translation. The various spinal motions are illustrated in FIGS. 2A-2C. In particular, FIG. 2A illustrates flexion and extension motions and axial loading, FIG. 2B illustrates lateral bending motion and FIG. 2C illustrated axial rotational motion. A normally functioning spinal motion segment provides physiological limits and stiffness in each rotational and translational direction to create a stable and strong column structure to support physiological loads.

Traumatic, inflammatory, metabolic, synovial, neoplastic and degenerative disorders of the spine can produce debilitating pain that can affect a spinal motion segment's ability to properly function. The specific location or source of spinal pain is most often an affected intervertebral disc or facet joint. Often, a disorder in one location or spinal component can lead to eventual deterioration or disorder, and ultimately, pain in the other.

Spine fusion (arthrodesis) is a procedure in which two or more adjacent vertebral bodies are fused together. It is one of the most common approaches to alleviating various types of spinal pain, particularly pain associated with one or more affected intervertebral discs. While spine fusion generally helps to eliminate certain types of pain, it has been shown to decrease function by limiting the range of motion for patients in flexion, extension, rotation and lateral bending. Furthermore, the fusion creates increased stresses on adjacent non-fused motion segments and accelerated degeneration of the motion segments. Additionally, pseudarthrosis (resulting from an incomplete or ineffective fusion) may not provide the expected pain-relief for the patient. Also, the device(s) used for fusion, whether artificial or biological, may migrate out of the fusion site creating significant new problems for the patient.

Various technologies and approaches have been developed to treat spinal pain without fusion in order to maintain or recreate the natural biomechanics of the spine. To this end, significant efforts are being made in the use of implantable artificial intervertebral discs. Artificial discs are intended to restore articulation between vertebral bodies so as to recreate the full range of motion normally allowed by the elastic properties of the natural disc. Unfortunately, the currently available artificial discs do not adequately address all of the mechanics of motion for the spinal column.

It has been found that the facet joints can also be a significant source of spinal disorders and debilitating pain. For example, a patient may suffer from arthritic facet joints, severe facet joint tropism, otherwise deformed facet joints, facet joint injuries, etc. These disorders lead to spinal stenosis, degenerative spondylolithesis, and/or isthmic spondylotlisthesis, pinching the nerves that extend between the affected vertebrae.

Current interventions for the treatment of facet joint disorders have not been found to provide completely successful results. Facetectomy (removal of the facet joints) may provide some pain relief; but as the facet joints help to support axial, torsional, and shear loads that act on the spinal column in addition to providing a sliding articulation and mechanism for load transmission, their removal inhibits natural spinal function. Laminectomy (removal of the lamina, including the spinal arch and the spinous process) may also provide pain relief associated with facet joint disorders; however, the spine is made less stable and subject to hypermobility. Problems with the facet joints can also complicate treatments associated with other portions of the spine. In fact, contraindications for disc replacement include arthritic facet joints, absent facet joints, severe facet joint tropism, or otherwise deformed facet joints due to the inability of the artificial disc (when used with compromised or missing facet joints) to properly restore the natural biomechanics of the spinal motion segment.

While various attempts have been made at facet joint replacement, they have been inadequate. This is due to the fact that prosthetic facet joints preserve existing bony structures and therefore do not address pathologies that affect facet joints themselves. Certain facet joint prostheses, such as those disclosed in U.S. Pat. No. 6,132,464, are intended to be supported on the lamina or the posterior arch. As the lamina is a very complex and highly variable anatomical structure, it is very difficult to design a prosthesis that provides reproducible positioning against the lamina to correctly locate the prosthetic facet joints. In addition, when facet joint replacement involves complete removal and replacement of the natural facet joint, as disclosed in U.S. Pat. No. 6,579,319, the prosthesis is unlikely to endure the loads and cycling experienced by the vertebra. Thus, the facet joint replacement may be subject to long-term displacement. Furthermore, when facet joint disorders are accompanied by disease or trauma to other structures of a vertebra (such as the lamina, spinous process, and/or transverse processes) facet joint replacement is insufficient to treat the problem(s).

Most recently, surgical-based technologies, referred to as "dynamic posterior stabilization," have been developed to address spinal pain resulting from more than one disorder, when more than one structure of the spine have been compromised. An objective of such technologies is to provide the support of fusion-based implants while maximizing the natural biomechanics of the spine. Dynamic posterior stabilization systems typically fall into one of two general categories: posterior pedicle screw-based systems and interspinous spacers.

Examples of pedicle screw-based systems are disclosed in U.S. Pat. Nos. 5,015,247, 5,484,437, 5,489,308, 5,609,636 and 5,658,337, 5,741,253, 6,080,155, 6,096,038, 6,264,656 and 6,270,498. These types of systems involve the use of screws that are positioned in the vertebral body through the pedicle. Certain types of these pedicle screw-based systems may be used to augment compromised facet joints, while others require removal of the spinous process and/or the facet joints for implantation. One such system, the Zimmer Spine Dynesys® employs a cord which is extended between the pedicle screws and a fairly rigid spacer which is passed over the cord and positioned between the screws. While this system is able to provide load sharing and restoration of disc height, because it is so rigid, it does not effective in preserving the natural motion of the spinal segment into which it is implanted. Other pedicle screw-based systems employ articulating joints between the pedicle screws. Because these types of systems require the use of pedicle screws, implantation of the systems are often more invasive to implant than interspinous spacers.

Where the level of disability or pain to the affected spinal motion segments is not that severe or where the condition, such as an injury, is not chronic, the use of interspinous spacers are preferred over pedicle based systems as they require a less invasive implantation approach and less dissection of the surrounding tissue and ligaments. Examples of interspinous spacers are disclosed in U.S. Pat. Nos. Re. 36,211, 5,645,599, 6,149,642, 6,500,178, 6,695,842, 6,716,245 and 6,761,720. The spacers, which are made of either a hard or compliant material, are placed in between adjacent spinous processes. The harder material spacers are fixed in place by means of the opposing force caused by distracting the affected spinal segment and/or by use of keels or screws that anchor into the spinous process. While slightly less invasive than the procedures required for implanting a pedicle screw-based dynamic stabilization system, implantation of hard or solid interspinous spacers still requires dissection of muscle tissue and of the supraspinous and interspinous ligaments. Additionally, these tend to facilitate spinal motion that is less analogous to the natural spinal motion than do the more compliant and flexible interspinous spacers. Another advantage of the compliant/flexible interspinous spacers is the ability to deliver them somewhat less invasively than those that are not compliant or flexible; however, their compliancy makes them more susceptible to displacement or migration over time. To obviate this risk, many of these spacers employ straps or the like that are wrapped around the spinous processes of the vertebrae above and below the level where the spacer is implanted. Of course, this requires some additional tissue and ligament dissection superior and inferior to the implant site, i.e., at least within the adjacent interspinous spaces.

With the limitations of current spine stabilization technologies, there is clearly a need for an improved means and method for dynamic posterior stabilization of the spine that address the drawbacks of prior devices. In particular, it would be highly beneficial to have a dynamic stabilization system that involves a minimally invasive implantation procedure, where the extent of distraction between the affected vertebrae is adjustable upon implantation and at a later time if necessary. It would be additionally advantageous if the system or device was also removable in a minimally invasive manner.

SUMMARY OF THE INVENTION

The present invention provides devices, systems and methods for stabilizing at least one spinal motion segment. The stabilizing devices include an expandable spacer or member having an unexpanded or lower profile configuration and an expanded or higher profile configuration. The unexpanded or lower profile, in certain embodiments, facilitates delivery of the device to an implant site by reducing the space requirements for such delivery. In an expanded or higher profile configuration, the spacer device has a size, volume, diameter, length, cross-section and/or shape configured for positioning between the spinous processes of adjacent vertebrae in order to engage the vertebrae and/or distract the vertebrae relative to each other. Still yet, the expanded profile of the device may be further extended if necessary as elaborated on below.

In certain embodiments, the spacer or expandable member is a balloon made of either non-compliant or compliant material which may be porous or non-porous, or may include a mesh material which may be coated or lined with a porous or non-porous material. The material may define a cavity which is fillable with an inflation and/or expansion medium for inflating and/or expanding the expandable member. The device may further include a port for coupling to a source of inflation/expansion medium. In certain embodiments, the port may be used to deflate or evacuate the expandable member.

In other embodiments, the spacer or expandable members are cages, struts, wires or solid objects having a first or unexpanded shape (having a lower profile) which facilitates delivery to the implant site and a second or expanded shape (having a larger profile) which facilitates distraction between vertebrae. The devices may have annular, spherical, cylindrical, cross, "X", star or elliptical shapes when in an expanded condition and/or unexpanded condition. The expandable members may be self-expanding or adjustably expandable depending on the extent of distraction required. Certain of the devices may be further extended once in an expanded state. For example, the height dimension of the device, or that dimension which affects distraction between adjacent vertebrae and/or spinous processes, may be further increased upon expansion in order to achieve the amount of distraction desired.

The stabilizing devices may be configured such that the transformation from the low-profile state to the high-profile state is immediate or gradual, where the extent of expansion is controllable. The transformation may occur in multiple discrete steps (i.e., extension of a dimension after the device is in an expanded state), in one-step, or evolve in a continuous fashion where at least one of volume, shape, size, diameter, length, etc. until the desired expansion end point is achieved in order to accommodate the size of the interspinous implant space and/or the amount of distraction desired between adjacent vertebrae. In certain embodiments, a minimum expanded or high-profile state is initially achieved with the option to further expand or extend the high-profile state to accommodate the particular space requirements or distraction objectives of the implant site, This transformation may be reversible such that after implantation, the stabilizing device may be partially or completely unexpanded, collapsed, compressed, retracted, deflated or at least reduced in size, volume, etc. in order to facilitate removal of the member from the implant site or to facilitate adjustment or repositioning of the member in vivo.

The stabilizing devices may be configured to stay stationary in the implant site on their own (or "float") or maybe further fixed or anchored to surrounding tissue, e.g., bone (e.g., spinous processes, vertebrae), muscle, ligaments or other soft tissue, to ensure against migration of the implant. In their final deployed state, the stabilizing devices may be flexible to allow some degree of extension of the spine or may otherwise be rigid so as prevent extension altogether. Optionally, the devices may include one or more Markers on a surface of the expandable member to facilitate fluoroscopic imaging.

The invention further includes systems for stabilizing at least one spinal motion segment which include one or more of the expandable members as described above. For spacers having a balloon configuration, the systems may further include an expansion medium for injection within or for filling the interior of the expandable member via the port. For expandable members which are expandable by mechanical means or actuation, the systems may further include delivery mechanisms to which the stabilizing spacers are attached which, when actuated or released from the stabilizing device, cause the device to expand or deploy.

The subject systems may further include at least one means for anchoring or securing the expandable member to the spinal motion segment to prevent migration of the device from the implant site. In certain embodiments, the securing means is a screw or the like for penetrating bone, where the spacer is configured to receive or partially constrain the screw. The device may then be anchored or secured to a bony structure of the vertebrae, such as one of the spinous processes between which it is implanted. The device may be further configured to be anchored to a bony structure of both vertebrae between which it is implanted and, as such, function to "fuse" the vertebrae together. Such capability would allow a physician to convert a spinal stabilization procedure to a fusion procedure if upon commencing the implant procedure, the spinal motion segment being treated is observed to require such. Alternatively, such a device would allow a fusion procedure to be performed subsequently (e.g., months or years later) to the dynamic stabilization procedure should the affected spinal motion segment degenerate further. Without having to remove the device and/or implant additional components (other than bone screws or the like), trauma to the patient and the cost of the procedure is greatly minimized.

The invention further includes methods for stabilizing at least one spinal motion segment which involve the implantation of one or more devices or expandable spacers of the present invention, in which the expandable member is positioned between the spinous processes of adjacent vertebrae in an unexpanded or undeployed condition and then subsequently expanded or deployed to a size and/or shape for selectively distracting the adjacent vertebrae. The invention also contemplates the temporary implantation of the subject devices which may be subsequently removed from the patient once the intended treatment is complete. The methods may also include adjustment of the implants in vivo.

Many of the methods involve the percutaneous implantation of the subject devices from either an ipsolateral approach or a mid-line approach into the interspinous space. Certain methods involve the delivery of certain components by a lateral approach and other components by a mid-line approach. The implantation methods may involve the use of cannulas through which the stabilizing devices are delivered into an implant site, however, such may not be required, with the stabilizing devices be configured to pass directly through an incision.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 5A-5C illustrates top, dorsal and side views of an initial step of the method of the present invention in which a cannula is delivered to the target implant site, FIGS. 6A and 6B illustrate dorsal and side views of the step of dissecting an opening within the spinous ligament utilizing a cutting instrument of the system of FIGS. 3 and 4. FIG. 6C is an enlarged view of the target area within the spinous ligament.

FIGS. 7A and 7B illustrate dorsal aid side views of the step of inserting the interspinous device of FIG. 4A into the dissected opening of the spinous ligament. FIGS. 7C and 7D are enlarged views of the target area in FIGS. 7A and 7B, respectively.

FIGS. 8A and 8B illustrate dorsal aid side views of the step of inflating or expanding the interspinous device of FIG. 4A within the implant site. FIGS. 8C and 8D are enlarged views of the target area in FIGS. 8C and 8D, respectively.

FIG. 10A illustrates a dorsal view of the step of further securing the interspinous device of FIG. 4A within the implant site. FIG. 10B is an enlarged view of the target area in FIG. 10A.

FIGS. 11A and 11B illustrate dorsal aid side views of the step of inserting another embodiment of an interspinous device into the dissected opening of the spinous ligament. FIGS. 11C and 11D are enlarged views of the target area in FIGS. 11A and 11B, respectively.

FIGS. 12A and 12B illustrate dorsal aid side views of the step of expanding the interspinous device of FIGS. 11A-11D within the implant site. FIGS. 12C and 12D are enlarged views of the target area in FIGS. 12A and 12B, respectively.

FIGS. 18A and 18B illustrate another interspinous device of the present invention in undeployed and deployed states, respectively.

FIGS. 19A and 19B illustrate the device of FIG. 18 implanted within an interspinous space and operably coupled to a delivery device of the present invention.

FIGS. 28A' and 28A'' illustrate side and front views of the interspinous spacer device in an undeployed state in the context of the step illustrated in FIG. 28A.

FIG. 28B illustrates a step in a method of implanting the interspinous spacer device of FIGS. 26A and 26B. FIGS. 28B' and 28B'' illustrate side and front views of the interspinous spacer device in a partially deployed state in the context of the step illustrated in FIG. 28B.

FIG. 28C illustrates a step in a method of implanting the interspinous spacer device of FIGS. 26A and 26B. FIGS. 28C' and 28C'' illustrate side and front views of the interspinous spacer device in a partially deployed state in the context of the step illustrated in FIG. 28C.

FIGS. 31A and 31B illustrate perspective views of another stabilizing device of the present invention in partial and fully deployed states, respectively.

FIGS. 34A and 34B illustrate a passively bendable or pivotable extension aim usable with the extension members of the present invention.

FIGS. 35A and 35B illustrate an extension member of the present invention having pivotable extension arms.

FIGS. 39A-39C illustrate perspective, side and end view respectively of a tool of the present invention suitable for facilitating posterior implantation of many of the spacers of the present invention through the supraspinous ligament.

DETAILED DESCRIPTION OF THE INVENTION

Figure 1:
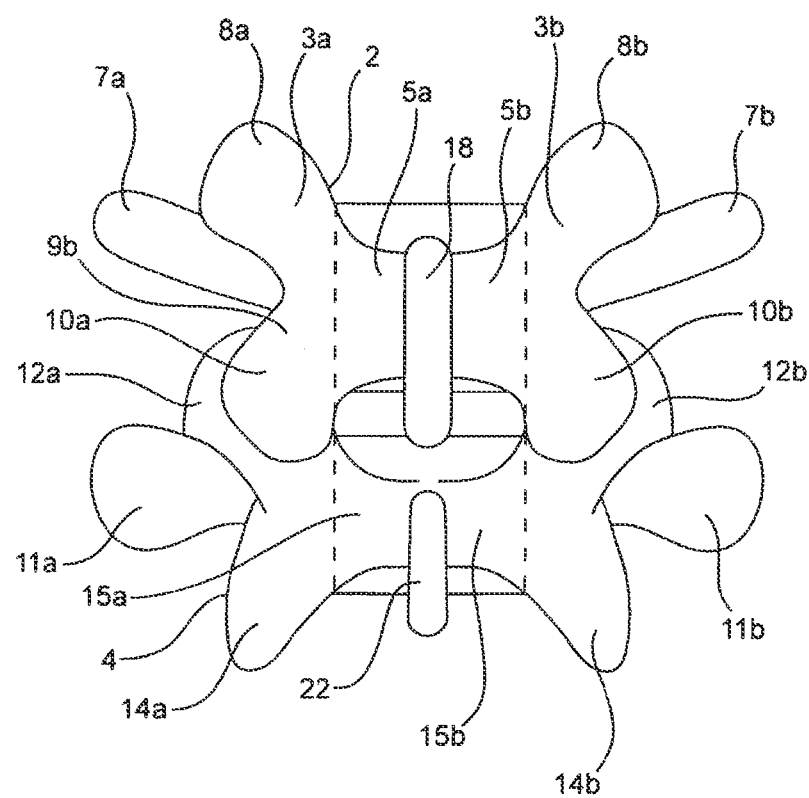
FIG. 1 illustrated a perspective view of a portion of the human spine having two vertebral segments.

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screw and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention will now be described in greater detail by way of the following description of exemplary embodiments and variations of the devices and methods of the present invention. The invention generally includes an interspinous spacer device as well as instruments for the percutaneous implantation of the interspinous spacer. A key feature of the interspinous spacer device is that it is expandable from a low profile configuration to a higher profile or operative configuration. This design allows the device, when in the low profile condition, to be delivered by percutaneous means without requiring the removal of any portion of the spinal motion segment into which the device is implanted.

As mentioned above, certain of the devices include balloon embodiments or those having expandable cavities which are expandable by the introduction of an inflation or expansion medium therein. Many of these are illustrated in FIGS. 3-14. Certain other devices include those which have a more mechanical structure which is self-expandable upon release from a confined condition or which is actively expandable by actuation of another instrument. These are illustrated in FIGS. 15-31.

Figure 3A:
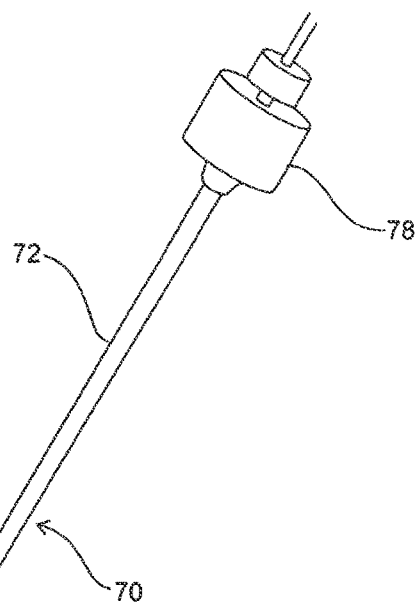
FIG. 3A illustrates an interspinous device of the present invention in an unexpanded or collapsed state coupled to a cannula of the delivery system of the present invention.
Figure 3B:
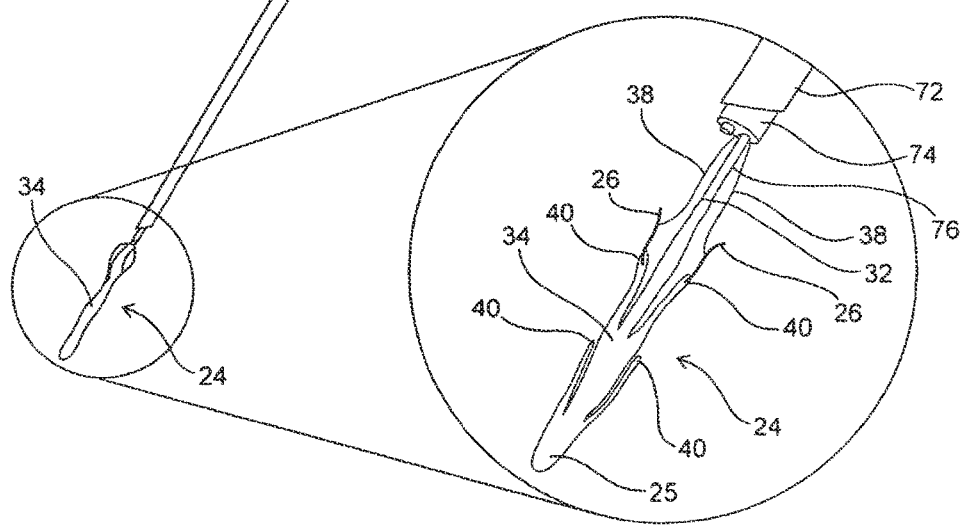
FIG. 3B is an enlarged view of the interspinous device of FIG. 3A.
Figures 4A, 4B:
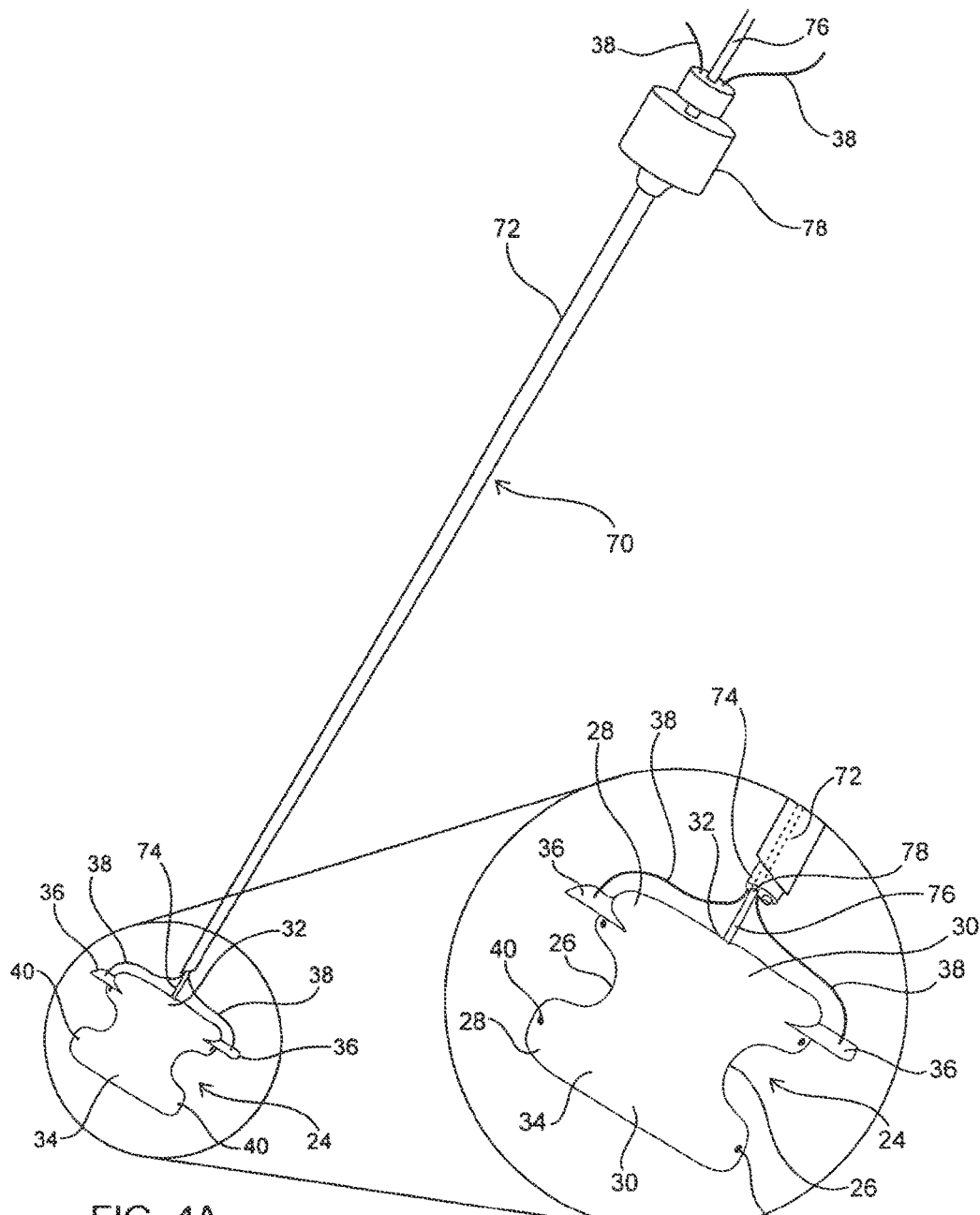
FIG. 4A illustrates an interspinous device of the present invention in an expanded state coupled to a cannula of the delivery system of the present invention.
FIG. 4B is an enlarged view of the interspinous device of FIG. 4A.

Referring now to the drawings and to FIGS. 3 and 4 in particular, an exemplary interspinous spacer device 24 of the present invention is illustrated in collapsed and expanded configurations, respectively. Interspinous device 24 includes an expandable spacer body 4 that has a size and shape when in the expanded condition for operative positioning between the spinous processes of adjacent superior and inferior vertebrae of the spinal motion segment being treated. Expandable body 34 is made of an expandable or inflatable biocompatible material such as non-porous material, e.g., latex, acrylate or a metal mesh, e.g., a nitinol or titanium cage.

Those spacers made of an inflatable non-porous material, i.e., balloon type spacers (see FIGS. 3-10), are inflated with an inflation or expansion medium, such as air, saline, another biologically compatible fluid, or a flowable solid material, such as polyurethane, or a gel, which thickens or hardens substantially upon injection into balloon 34. In one embodiment, balloon 34 is initially inflated with air to provide some structure or rigidity to it to facilitate its optimum positioning and alignment between the spinous processes. Once positioned as desired, balloon 34 is injected with a flowable solid material (the air therein being displaced possibly via a vent hole within port 32). In certain embodiments, the expandable body is made of a non-compliant or semi-compliant material so as to maintain a substantially fixed shape or configuration and ensure proper, long-term retention within the implant site. In other embodiments, the expandable member may be made of a compliant material. In any embodiment, the compressibility and flexibility of balloon 34 can be selected to address the indications being treated.

Other embodiments of the subject spacers are made of an expandable mesh or cage (see FIGS. 11-12). The mesh or cage maybe made of a super-elastic memory material which is compressible for delivery through a cannula and which is self-expanding upon implantation. Upon expansion, the mesh or cage may be self-retaining whereby its struts, links or wires are sufficiently rigid by themselves to maintain the expanded condition and withstand the natural forces exerted on it by spine. The mesh or cage may have an exterior coating or an interior lining made of materials similar to or the same as that used for the balloon spacers, or may otherwise be embedded in such material, In certain embodiments, an expansion medium may be used to fill the interior of the cage or mesh structure, such as with a biologically compatible fluid or flowable solid material used with the balloon-type embodiments.

In certain embodiments of present invention, either during the implant procedure or in a subsequent procedure, the size or volume of the implanted expandable spacer may be selectively adjusted or varied. For example, after an initial assessment upon implant, it may be necessary to adjust, either reduce or increase, the size or volume of the spacer to optimize the intended treatment. Further, it may be intended to only temporarily implant the spacer for the purpose of treating a temporary condition, e.g., an injured or bulging or herniated disk. Once the repair is achieved or the treatment completed, the spacer may be removed, either with or without substantially reducing the size or volume of the spacer, In other embodiments, the spacer as well as the inflation/expansion material may be made of biodegradable materials wherein the spacer degrades after a time in which the injury is healed or the treatment completed.

When unexpanded or deflated, as shown in FIGS. 3A and 3B (balloon type) and in FIGS. 11C and 11D (mesh type) expandable body 34 has a low profile, such as a narrow, elongated shape, to be easily translated through a delivery cannula 70. The shape of expandable body 34, when in an expanded or inflated state, has larger profile which is generally H-shaped. Expandable body 34 has lateral or side portions 30, end portions 26 and apexes 28 defined between the side portions 30 and the end portions 26. End portions 26 are preferably recessed or contoured to provide a narrowed central portion along the height dimension or major axis of expandable body 34 to readily fit between and to conform to the spinous processes. Accordingly, expandable body 34 has an apex-to-apex dimension (i.e., height or major axis dimension) from about 1 cm to about 5 cm, and typically from about cm to about 2 cm, and a width dimension (minor axis dimension) from about 1 cm to about 4 cm and typically about 1 cm.

For those embodiments of expandable bodies which comprise a balloon configuration, balloon 34 has an inflation or injection port 32 at a sidewall 30 for coupling to a source of inflation or expansion material or medium. Port 32 may consist of a one-way valve which is self-sealing upon release from an inflation mechanism or tube 76. Port 32 is further configured to releasably engage from tube 76, where such engagement may be threaded or involve a releasable locking mechanism. Where the expandable body comprises a mesh or cage, port 32 simply acts as an exit port, however, where an expansion material is used, it also functions as an injection port for the expansion material.

Optionally, device 24 may include a pair of tabs 36 which may be positioned on one side of the device where the tabs 36 are preferably situated at the apexes 28 of expandable body 34. Pins or screws (not yet shown) may be used to secure the tabs against the spinous process to further ensure long-term retention of device 24 within the implant site. Tabs 36 are made of a biocompatible material, such as latex, acrylate, rubber, or a metal, and may be made of the same material used for the expandable member 34. Shown here attached to tabs 36 are tethers 38 which are used in part to manipulate the positioning of expandable body 34 upon implantation into the targeted spinal motion segment. The tethers may be made of any suitable material including but not limited to materials used to make conventional sutures. They may also be made of a biodegradable material. While two tabs and associated tethers are provided in the illustrated embodiment, one, three or more may be employed, where the respective tabs are located on the expandable body so as to be adjacent a bony structure of the vertebra suitable for anchoring thereto. In embodiments which do not employ securing tabs 36, tethers 38 may be attached directly to the expandable body itself.

Optionally still, device 24 may further include radiopaque markers 40 on the surface of expandable body 34 visible under fluoroscopic imaging to facilitate positioning of the expandable body. Any number of markers 40 may be employed anywhere on expandable body 34, however, as few as four markers, one at each apex, may be sufficient With embodiments employing cage or mesh expandable bodies, the cage or mesh material itself may be radiopaque.

A system of the present invention includes a cannula device 70 having an outer sheath 72, a proximal hub 78 and preferably at least two interior lumens 74, 76 for the percutaneous delivery the device and other tools for implanting the device, which tools may include a cutting instrument 62 (see FIG. 6C), a device delivery instrument 76, an endoscope, etc., which tools will be further discussed in the context of the description of the subject methods with reference to FIGS. 5-10.

In FIGS. 5A-5C, the spinal motion segment of FIG. 1 is illustrated having spinal ligament 54 extending between the superior spinous process 18 and the inferior spinous process 22. A percutaenous puncture is made into the skin 30 adjacent the target spinal motion segment of a patient undergoing the implantation of the interspinous device of the present invention, and a cannula 70 is penetrated to the spinous ligament 54. The puncture and subsequent penetration may be made by way of a sharp distal tip of cannula 70 or by a trocar (not shown) delivered through a lumen of cannula 70.

As illustrated in FIGS. 6A-6C, the spinous ligament 54 is then dissected and an opening 58 created therein by way of a cutting instrument 60, such as a simple scalpel, an electrosurgical device or the like, delivered through a lumen of cannula 70. Cutting instrument 60 may then be removed from cannula 70 and, as illustrated in FIGS. 7A-7D (balloon type) and in FIGS. 11A-11D (cage type), a delivery instrument 16 having interspinous device 24 operatively preloaded is delivered through cannula 70.

The preloading of device 24 to delivery instrument 76 involves providing expandable body 34 in an unexpanded or deflated state and releasably coupled, as described above, by way of inflation or injection port 32 of expandable body 34 to the distal end of delivery instrument 76. In addition to functioning as a pusher, instrument 76 may act as an inflation lumen for balloon type embodiments through which an inflation medium is transported to within expandable body 34.

Depending upon the material used to fabricate expandable body 34, the expandable body may have a degree of stiffness in an unexpanded or deflated state such that it may maintain an elongated configuration so as to be directly insertable and pushable through cannula 70. This may the case where the expandable member 34 is made of a cage or mesh material. Alternatively, a pusher or small diameter rod (not shown) may be inserted through inflation port 32 to within expandable body 34 to keep it in an elongated state so as to prevent expandable body 4 from bunching within cannula 70 and to provide some rigidity to more effectively position the expandable body in the target implant site. The rod is then removed from expandable body 34 and from delivery device 76 upon positioning the expandable body at the target implant site, in either case, expandable body 34 is folded or compressed about its minor axis with the side wall opposite the inflation port 32 defining a distal end 25 (see FIG. 3B) and the apexes 28 of the expandable body folded proximally of distal end 25 to provide a streamline, low profile configuration for delivery through cannula 70.

Once interspinous device 24 is preloaded to delivery device 76 as just described, device 24 is then inserted into a lumen of cannula 70 with tethers 38 pulled back and trail proximally so that the tether ends 38a extend from hub 78 of cannula 70. Expandable body member 34 is translated through cannula 70 to within opening 58 within spinous ligament 54 as best illustrated in FIGS. 7C and 11C. For best results, expandable body 34 is centrally positioned within opening 58 so that the countered ends 26 of expandable body 34 readily engage with the opposed spinous processes 18, 22. Fluoroscopy may be employed to visualize markers 40 on as to ensure that expandable body 34 centrally straddles the spinous ligament opening 58, i.e., the markers on the distal side 25 of the expandable body are positioned on one side of the spine and the markers on the proximal side of the expandable body (the side on which port 32 is located) are positioned on the other side of the spine.

Once centrally positioned, expandable body 34 is inflated or expanded, as illustrated in FIGS. 8A-8D and 12A-12D. For balloon spacers, inflation occurs by allowing an inflation or expansion medium, as discussed above, to enter into the interior of the expandable body via port 32. For expandable mesh spacers, the expandable body may be configured to expand automatically upon exiting cannula 70. The inflation or expansion of expandable body 34 may also be visualized under fluoroscopy whereby markers 40, as best shown in FIG. 8C, are observed and the position of expandable body 34 may be adjusted to ensure optimum positioning upon complete inflation. Adjustments of the expandable body's position may be accomplished by manually pulling on one or both tether ends 38a which in turn pulls on tabs 26 to which the tethers 38 are attached at their proximal ends. The tethers 38 are selectively pulled as necessary to center or optimally position interspinous expandable body 34 to achieve the desired treatment of the targeted spinal motion segment.

With embodiments in which the expandable body is initially inflated with air and then filled with a solid or fluid medium, the latter is preferably not delivered or injected into the interior of the expandable body until the position of the expandable body within the interspinous space has been verified and optimized. This is beneficial in situations where, upon inflation, it is found that the expandable body is misaligned within the interspinous space and requires repositioning. The expandable body may simply be deflated of air to the extent necessary and repositioned in a less inflated or deflated state. If necessary, for example where it is found that the maximum spacer or expandable body size is insufficient for the particular application at hand, expandable body 34 may be completely deflated and removed and replaced with a more suitably sized unit.

Figure 9A:
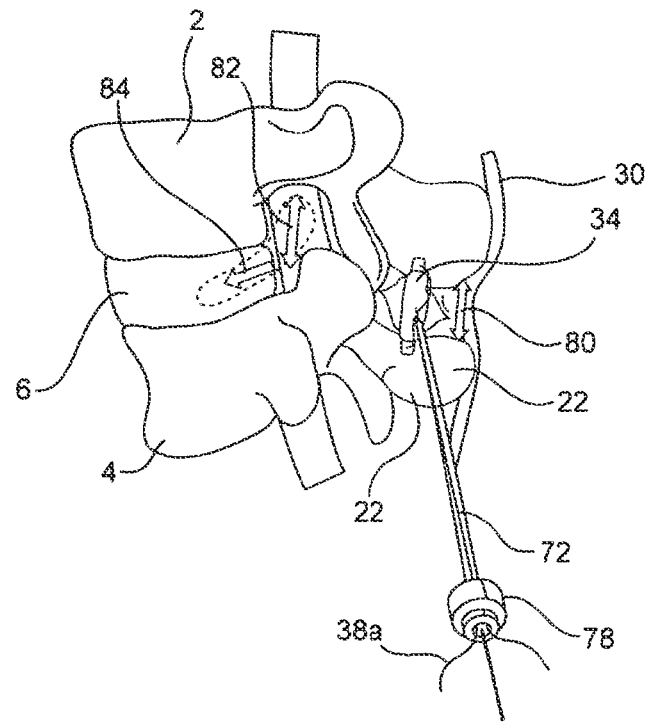
FIG. 9A illustrates a side view of the step of filling the interspinous device of FIG. 4A with an expansion medium.
Figure 9B:
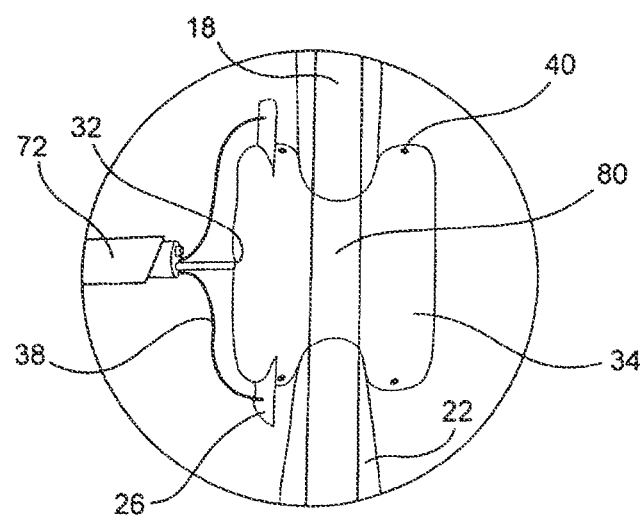
FIG. 9B is an enlarged view of the target area in FIG. 9A.
Figure 13A:
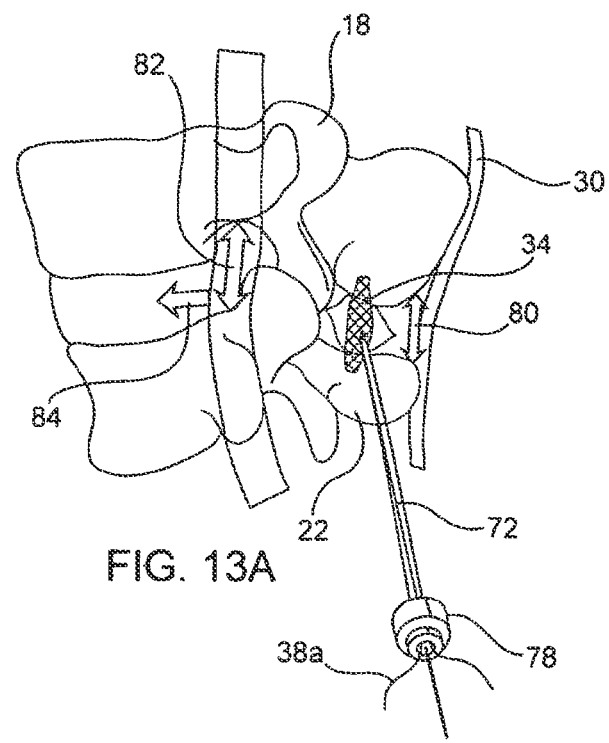
FIG. 13A illustrates a side view of the step of filling the interspinous device of FIGS. 11A-11D with an expansion medium.
Figure 13B:
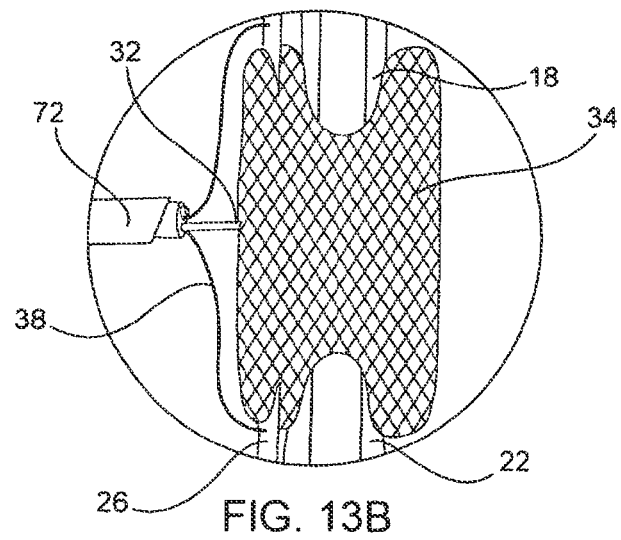
FIG. 13B is an enlarged view of the target area in FIG. 13A.

For balloon spacers and those mesh spacers which are not by themselves sufficiently self-retaining, once the position and extent of inflation or expansion of expandable body 34 are optimized, the expansion medium, e.g., polyurethane, is allowed to flow or injected into the interior of the expandable body via port 32. As illustrated in FIGS. 9A and 9B, expandable body 34 is caused to expand to a selected volume and in so doing forces apart (see arrow 80) the spinous processes 18, 22 in between which it is situated. This selective distraction of the spinous processes also results in distraction of the vertebral bodies 2, 4 (see arrow 82) which in turn allows the disk, if bulging or distended, to retract to a more natural position (see arrow 84). Again, the extent of distraction or lordosis undergone by the subject vertebrae can be monitored by observing expandable body markers 40 under fluoroscopy.

The extent of possible distraction maybe limited by the capacity of expandable body 34 and the type of expandable body material employed. In certain embodiments, such as expandable bodies made of non-compliant or semi-compliant balloons, the requisite volume of the inflation medium may be substantially fixed whereby the balloon achieves its fully expanded configuration upon filling it with the fixed volume of medium. In other embodiments, such as with balloons made of a compliant material, the extent of expansion may be variable and selectable intraoperatively depending on the extent of lordosis or distraction to be achieved between the spinous processes in which balloon 34 is now interposed.

Upon achieving the desired distraction between the vertebrae, inflation/expansion lumen 76 is disengaged from expandable body port 32 which then becomes sealed by means of a one-way valve that is closed upon disengagement of lumen 76. Inflation/expansion lumen is then removed from cannula 70. While the opposing compressive force exerted on expandable body 34 by the distracted spinous processes 18, 22 may be sufficient to permanently retain expandable body 34 therebetween, the interspinous device may be further secured to the spinous processes 18, 22 to ensure that the expandable body does not slip or migrate from its implanted position. To this end, tabs 36 are anchored to the spinous processes as illustrated in FIGS. 10A and 10B and in FIGS. 13A and 13B. Any type of anchoring means, such as screws, tacks, staples, adhesive, etc. may be employed to anchor tabs 36. Here, cannulated screws 90 are used as anchors and are delivered to the target site releasably coupled to screw driving instrument 88. While various screw attachment and release mechanisms may be employed, a simple configuration involves providing the screws 90 with a threaded inner lumen which is threadably engagable with the threaded distal end of instrument 88.

To ensure accurate placement of screws 90, along with instrument 88, can be tracked and translated over respective tethers 38, which function as guide wires. By manipulating instrument 88, the screws are driven or screwed into the respective spinous process. Screwdriver 88 is then disengaged or unscrewed from screw 90. After both tabs 36 are securely anchored to the spinous processes, the screwdriver and the cannula may be removed from the patient's back.

FIGS. 14A-14F illustrate an alternative method for implanting the expandable member. In particular, the method contemplates pre-inflating or pre-expanding the expandable member prior to positioning the expandable member within the interspinous space. To accomplish this, the vertebrae 2 and 4 may be distracted prior to insertion of the pre-expandable balloon implant. A temporary distraction mechanism, such as another balloon or a mechanically actuated device, is inserted into the interspinous space. When the desired amount of distraction is achieved, the permanent or implantable expandable member can then be placed within the interspinous space, and the temporary distraction member may then be removed from the space.

While certain of the expandable spacers are intended to be permanently implanted within a spine, certain others may be implanted only temporarily to facilitate the healing of an injury or the treatment of a reversible or non-chronic condition, such as a herniated disk. For such temporary treatments, the expansion material most likely is a fluid, such as saline, which may be easily aspirated through port 32 or may be allowed to drain out via a penetration or cut made in the expandable member. In those embodiments in which the expansion material is a flowable solid, which may or may not subsequently harden within the expandable member, the material may be one that is reconstitutable into a liquid form which may then be subsequently aspirated or evacuated from the expandable member. For percutaneous removal of the expandable member, a cannula such as cannula 70 may be used and an aspiration instrument delivered therethrough and coupled to port 32. After deflation and/or evacuation of the expandable member, and removal of the tacks, sutures, staples, etc. if such are used to secure tabs 36, the expandable member may be easily removed through cannula 70. With biodegradable spacers, removal of the spacer is obviated.

It should be noted that any of the above-described steps or procedures, including but not limited to cannulation of the target area, dissection of the spinous ligament, insertion of the expandable body within the dissected opening of the spinous ligament, inflation and/or expansion of the expandable body, adjustment or readjustment of the expandable body, and anchoring of the tabs, etc., may be facilitated by way of a scope 62 delivered through a lumen of cannula 70 to the open distal tip of cannula 70. Alternatively, a second cannula delivered through another percutaneous penetration may be employed for use of an endoscope and any other instruments needed to facilitate the procedure.

Figure 14A:
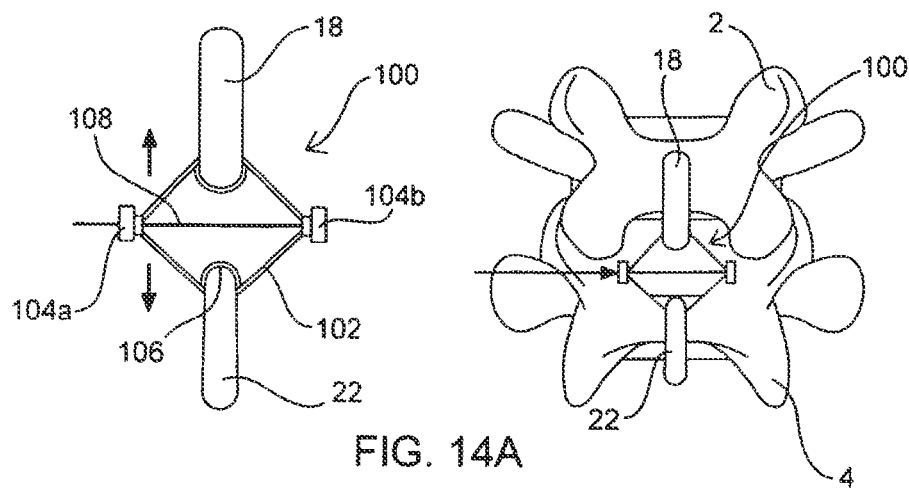
FIGS. 14A-14F illustrate dorsal views of another interspinous device of the present invention and a device for implanting the interspinous device where the implantation device is used to initially distract the interspinous space prior to implanting the interspinous device.
Figure 14B:
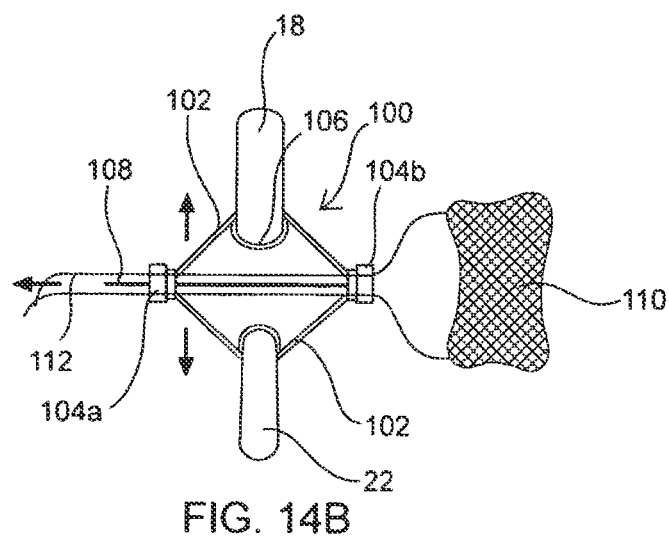

FIG. 14A illustrates an exemplary embodiment of a temporary distraction mechanism 100 having an expandable strut configuration. Mechanism 100 includes bilateral struts 102 which are hinged and foldable at hubs 104, respectively. Bridging the struts 102 at superior and inferior ends are spinous process engagement portions 106 which are preferably configured to conformingly engage with the spinous processes 18, 22. Extending centrally between hubs 104 is a distal portion of guide wire 108, which also extends proximally through proximal huh 104a. Guide wire 108 is in threaded engagement with hub 104a whereby hub 104a can be translated both proximally and distally along guide wire 108. As such, expandable member 100 can be provided in a low profile, compressed state upon proximally translating hub 104a in a proximal direction. In such a low-profile state, distraction mechanism 100 is easily deliverable through cannula 70, as described above, to with the interspinous space. Upon proper positioning, distraction mechanism 100 is expandable to a higher profile or expanded state by translating hub 104a toward hub 104b in a distal direction along guide wire 108, as illustrated in FIG. 14A.

After the desired amount of distraction is achieved between vertebrae 2 and 4, an implantable expandable member 110 of the present invention is delivered adjacent the distracted spinal motion segment. Expandable member 110 may be delivered from the same incision and side as distraction mechanism 100 (ipsolateral approach) and as well as through the same working channel, or may be delivered through a different incision on the same or opposing side of the spinal motion segment being treated (bilateral approach) using two different working channels. In the illustrated embodiment, expandable member 110 is delivered from the same side of the spinous process as distraction mechanism 100. Expandable member 110 may delivered through a separate designated lumen in cannula 70 and translated distally of hub 104b of distraction mechanism 100.

Figure 14C:
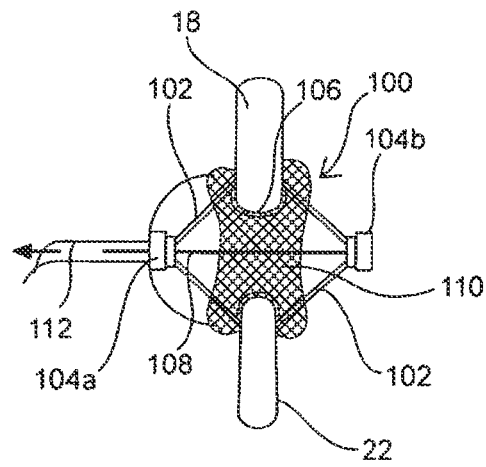
Figure 14D:
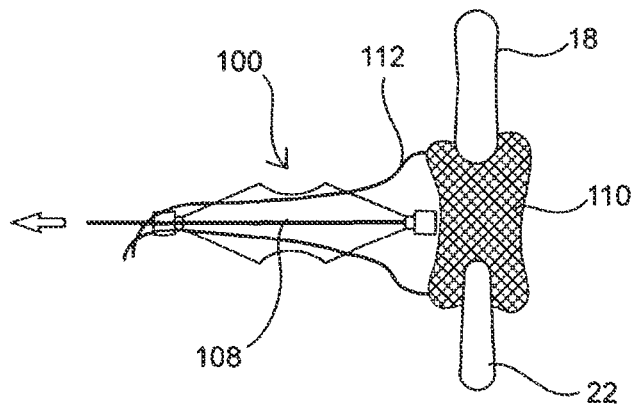
Figure 14E:
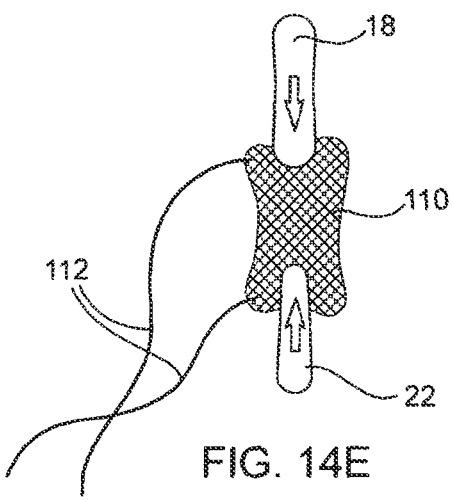
Figure 14F:
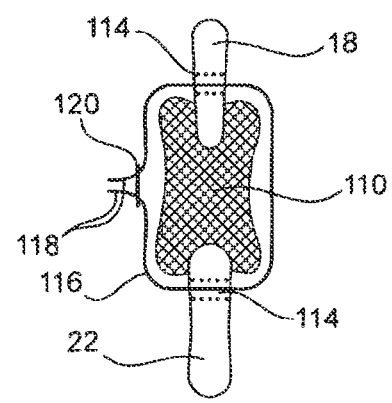

As shown in FIG. 148, after deployment, expandable member 110 is inflated or expanded as described above with respect to expandable member 34, for example, by way of an inflation lumen extending through guide wire 108. Tethers 112 may be provided on expandable member 110 to retract and manipulate it to within the interspinous space, as illustrated in FIG. 14C. Once expandable member 110 is properly positioned within the interspinous space, distraction mechanism 100 may be removed from the interspinous space immediately or, if the expandable member has been filled with a curable expansion medium or one that involves setting or hardening, the distraction mechanism may be kept in the interspinous space until the desired consistency, curing or hardening has been achieved by the expansion medium. To remove distraction mechanism 100 from the interspinous space, its profile is reduced to a low profile state, as illustrated in FIG. 14D. As mentioned earlier, this is accomplished by translating proximal hub 104a proximally along guide wire 108. Distraction member 100 may be retracted out through a cannula or removed directly in this low profile state, leaving expandable member 100 alone within the implant site as illustrated in FIG. 14E. Tethers 112 may then be cut or secured in place. Optionally, a strap 116 or the like may be implanted to further secure expandable member 110 within the implant site and reduce the risk of migration. Here, bores or holes 114 have been formed through the thickness of the spinous processes 18, 22 and strap 116 threaded there through with its ends secured together by a securing means 120, such as a suture, staple or clip, as illustrated in FIG. 14F. Alternatively, strap 116 could be wrapped around the spinous processes 18, 22.

Figure 15A:
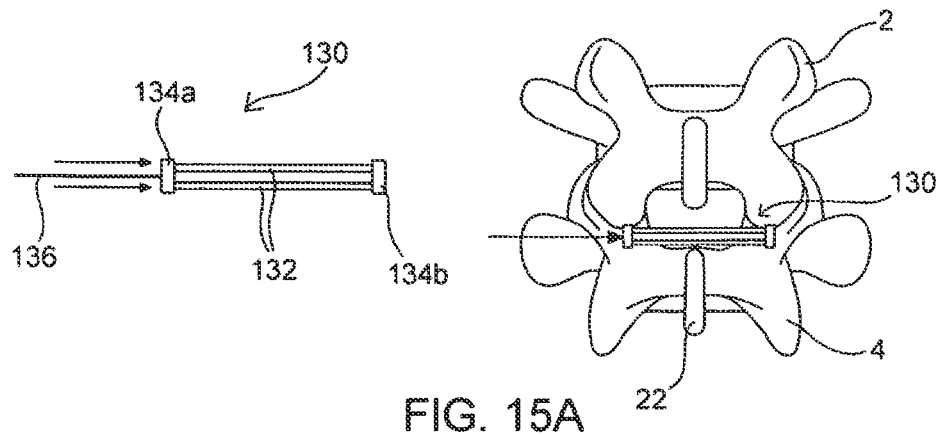
FIGS. 15A and 15B illustrate dorsal views of another interspinous device of the present invention implanted within an interspinous space.
Figure 15B:
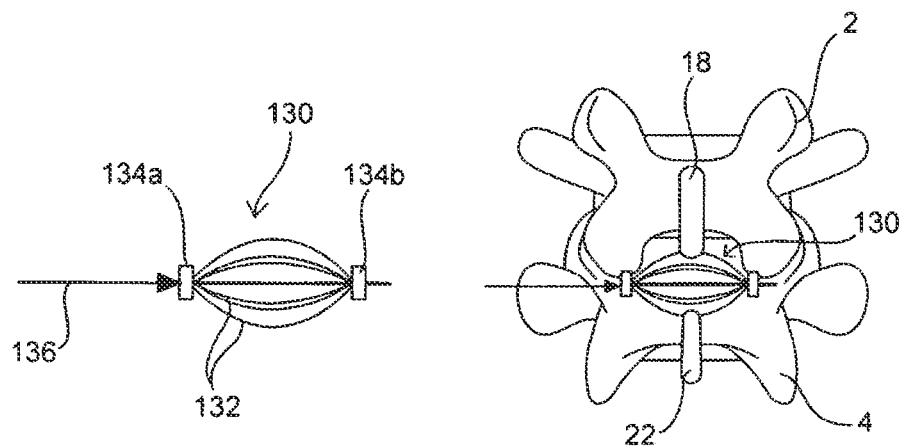
Figure 16A:
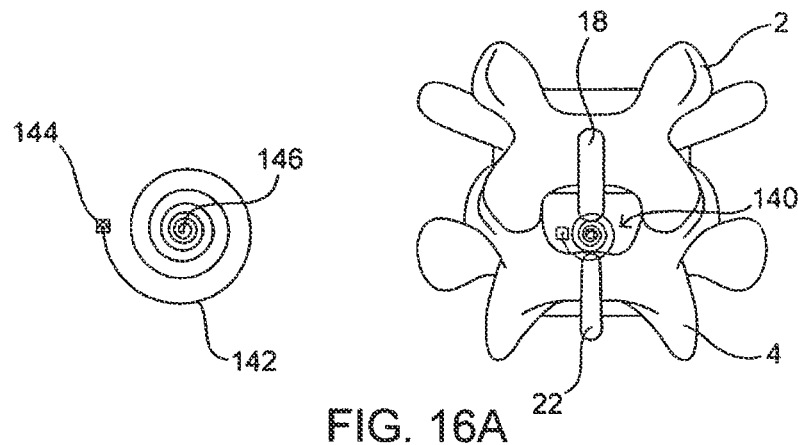
FIGS. 16A and 16B illustrate dorsal views of another interspinous device of the present invention implanted within an interspinous space.
Figure 16B:
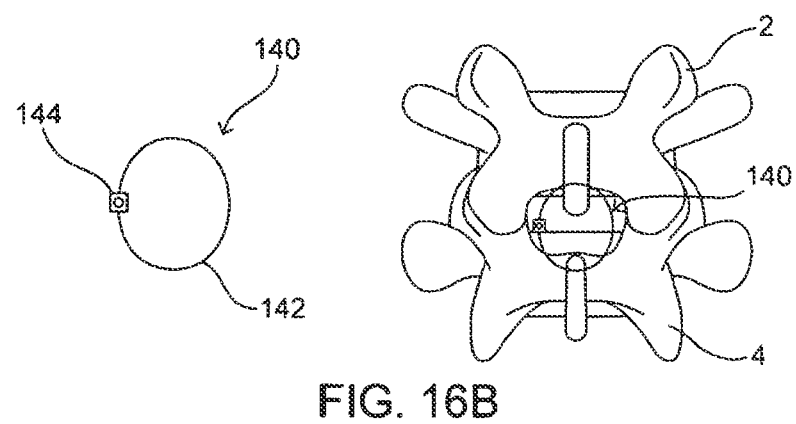
Figure 16C:
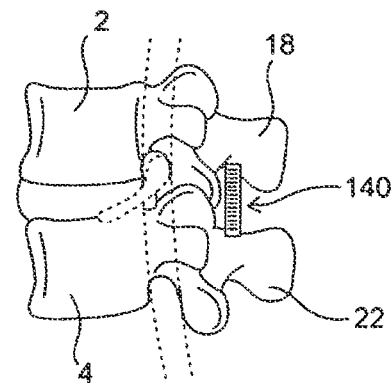
FIG. 16C is a side view of FIG. 16B.

In addition to the expandable balloon spacers, the present invention further provides for mechanically expandable spacers such as those illustrated in FIGS. 15-17. For example, expandable spacer 130 of FIG. 15A is a cage-like structure having spaced-apart, parallel strut members 132 extending between and fixed to hubs 134. Like the distraction mechanism of FIGS. 14A-14F, spacer 130 may be provided on and deliverable by way of a guide wire 136 which is threadably engaged to and disengagable from proximal hub 134a. After placement of spacer 130 within the interspinous space, as illustrated in FIG. 15A, spacer 130 is expanded by advancing proximal hub 134a distally along guide wire 136 thereby forcing struts 132 radially outward and away from each other whereby the expanded configuration of spacer 130 is elliptical or, in a more advanced state of expansion, substantially spherical. Once the desired degree of distraction is achieved between vertebrae 2 and 4, guide wire 136 unthreaded from hub 134a and removed from the implant region.

FIGS. 16A and 16B illustrate another embodiment of an expandable spacer 140 which is in the form of a coiled band 142 terminating at an outer end 144 having a configuration for receiving and locking onto inner end 146 upon full expansion or unwinding of the coil. The diameter of coil 142 in an unexpanded or fully wound state is small enough to allow easy insertion between spinous processes 18, 22. Upon proper positioning within the interspinous space, coil 142 is allowed to expand and unwind thereby distracting vertebrae 2 and 4 apart from each other. Once the desire level of distraction is achieved, inner end 146 is coupled to outer end 144. While the figures show band 142 inserted transversely to spinous processes 18, 22, it may alternatively be inserted in line or in the same plan defined by the spinous processes.

Figure 17A:
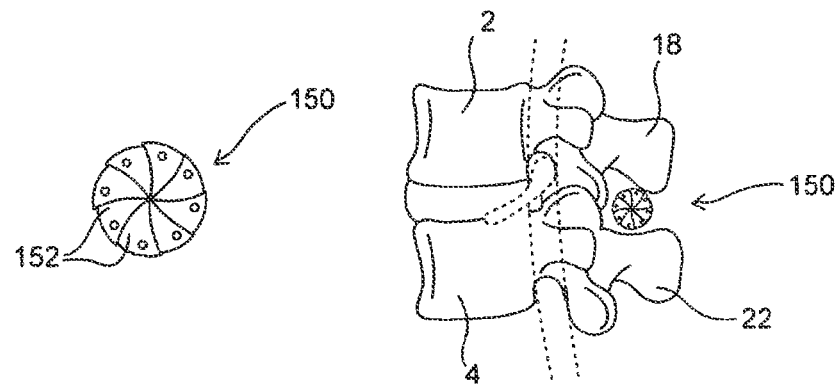
FIGS. 17A and 17B illustrate, side views of another interspinous device of the present invention implanted within an interspinous space.
Figure 17B:
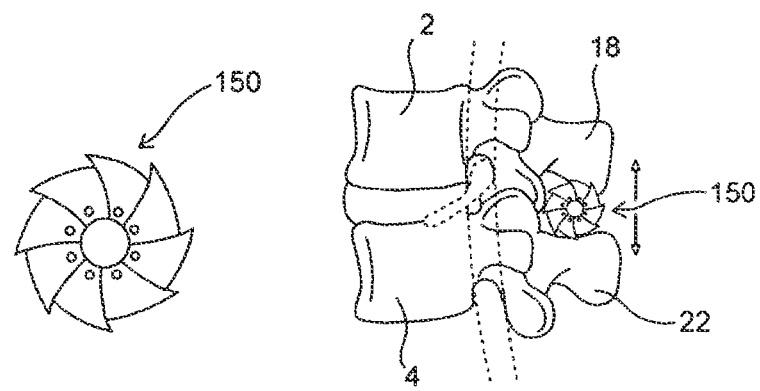
Figure 17C:
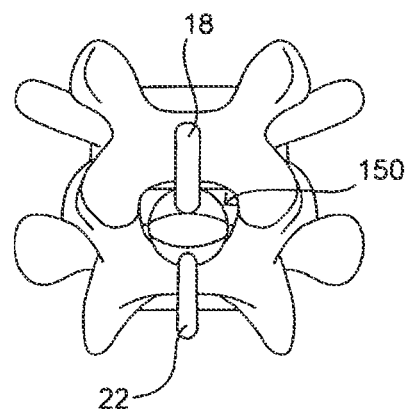
FIG. 17C is a dorsal view of FIG. 17B.

FIGS. 17A-17C illustrate another interspinous spacer 150 having interlocked nested portions 152. Nested portions 152 are each shaped and configured to be received within one of its adjacent portions and to receive the other of the adjacent portions when in a low profile state, as illustrated in FIG. 17A. Upon expansion of spacer 150, which may be spring loaded or be expandable by way of an instrument (not shown) which may be inserted into the spacer's center and rotated to flare portions 152, vertebrae 2 and 4 are caused to distract from each other. Portions 152 may have a configuration or shape which allows them to bite or dig into the spinous process 18, 22 and become securely retained therein.

FIGS. 18A and 18B illustrate another interspinous spacer 160 of the present invention in an undeployed or unexpanded state and a deployed or expanded state, respectively. Spacer 160 includes an expandable tubular member 162 having end portions 164a, 164b which are capped by hubs 166a, 166b, respectively. As is explained in greater detail below, one or both hubs may be provided fixed to tubular member 162 or may be releasably coupled thereto. A sleeve or retaining member 168 is circumferentially positioned about tubular between end portions 164a, 165a. Most typically, retaining member 168 is positioned substantially centrally (as shown) on tubular member 162, but may be positioned laterally towards one or the other end. Retaining member 168 has a length that covers about one third of the length of tubular member 162, but may be longer or shorter depending on the application. As is explained in greater detail below, interspinous spacer 160 may further include a core member (shown in FIG. 21) within the lumen of the tubular member and which may be provided integrated with spacer 160. Alternatively, the core member may be provided as a detachable component of the device used to deliver and implant the spacer (see FIGS. 19A and 19B).

In the undeployed state, as illustrated in FIG. 18A, spacer 160 has an elongated tubular or cylindrical shape, and may have any suitable cross-sectional shape, e.g., circular, oval, starred, etc., where the more angular cross-sections may allow the device to bite or dig into the spinous processes and for better retention. In this undeployed or lengthened state, tubular member 162 has a length in the range from about 20 mm to about 80 min, and more typically from about 30 mm to about 50 mm, and a diameter or average thickness in the range from about 4 mm to about 12 mm, and more typically from about 6 mm to about 9 mm. As such, spacer 160 is deliverable to an implant site between adjacent spinous processes in a minimally invasive manner.

In the deployed state, as illustrated in FIG. 18B, spacer 160 has a dumbbell or H-shaped configuration, where the length of spacer 160 is less than and the diameter or height of spacer 160 is greater than the corresponding dimensions of the spacer when in an undeployed state. In particular, the length dimension of the end portions 164a, 164b of tubular member 162 has been reduced by about 25% to about 70% while the diameter of the end portions 164a, 164b has been increased by about 50% to about 600%, and the diameter of the central or sleeve-covered portion has been increased by about 200% to about 400%, where the diameter of the portions of the tubular member 164a, 16411 not covered by retaining member 168 have a greater diameter than the portion of tubular member 162 which is covered by retaining member 168. The increased diameter of covered or central portion 168 distracts the adjacent vertebrae so as to provide pain relief. The diameter of hubs 166a, 166b may remain constant upon deployment of device 160. In this deployed state, tubular member 162 has a length in the range from about 15 mm to about 50 mm, and more typically from about 20 mm to about 40 mm, and an end portion diameter in the range from about 10 mm to about 60 mm, and more typically from about 15 mm to about 30 mm, and a central portion diameter in the range from about 5 mm to about 30 mm, and more typically from about 8 mm to about 15 mm. As such, when operatively placed and deployed within an interspinous space, the deployed spacer 160 fits snugly within the interspinous space and is held in place by the surrounding muscle, ligaments and tissue.

Any suitable materials may be used to provide a spacer 160 which is provided in a first state or configuration, e.g., the undeployed state illustrated in FIG. 18A, and which can be manipulated to achieve a second state or configuration, and back again if so desired. A polymer based material or any other material which allows for simultaneous axial shortening and radial expansion is suitable for use to form tubular member 162. The end portions 164a, 164b may be made of the same or a different material as that of the central or covered portion. A flexible or shaped memory material or any other material which also allows for simultaneous axial shortening and radial expansion, but which is less expandable, i.e., maintains a compressive force about tubular member 162, than the material employed for tubular member 162 may be used to form retaining member 168. As such, retaining member 168 limits the extent of radial expansion as well as axial shortening that the covered portion of tubular member 162 can undergo. Examples of suitable materials for the retaining member include but are not limited to Nitinol or polyethelene in a braided or mesh form. Further, the construct of retaining member 168 may be such that the radial force applied to the portion of tubular member 162 that it covers is constant or consistent along its length so as to maintain a constant diameter along its length or, alternatively, may have a varying radial force so as to allow for selective shaping of the covered portion of tubular member when in a deployed state. Retaining member 168 may be constructed so as to resist bending or flexing upon forcible contact with the spinous processes and, as such, does not conform to the spinous processes. Conversely, the retaining member 168 may be constructed from a more flexible material that allows for some compression and, as such, may conform or be conformable to the spinous processes. Further, the physical properties and dimensions of the materials used for both the tubular member and the retaining may be selected to provide the desired amount of distraction between target vertebrae.

Figure 20A:
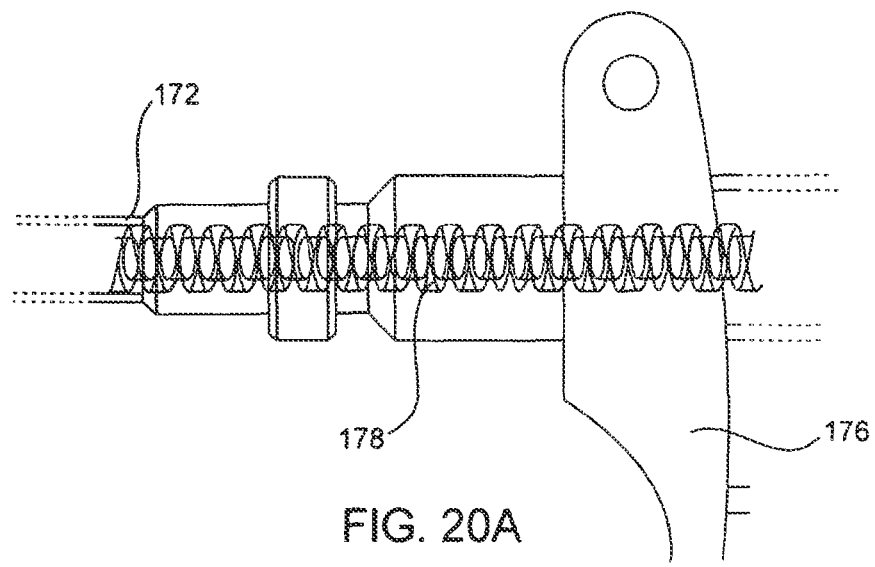
FIGS. 20A and 20B illustrate cut-away views of two embodiments of the handle portion of the delivery device of FIGS. 19A and 19B.
Figure 20B:
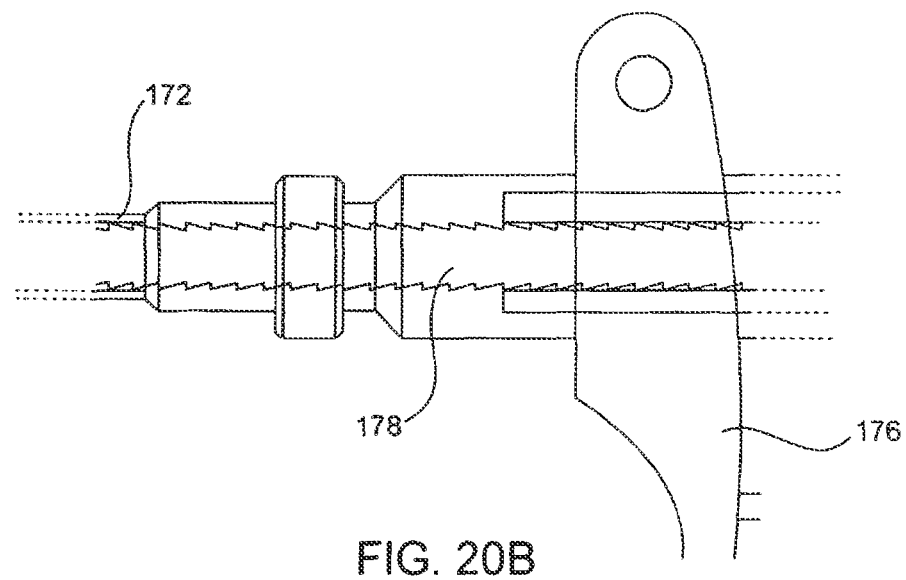

Referring now to FIGS. 19A and 19B, spacer 160 is shown operatively employed within an interspinous space and coupled to delivery device 170. Delivery device 170 includes an outer shaft 172 and an inner shaft 178, movable relative (axially, rotationally or both) to outer shaft 172, both extending from a handle mechanism 174. For example, inner shaft 178 may be configured to be retracted proximally within outer shaft 172, or outer shaft 172 may be configured to be advanced distally over inner shaft 178, or both configurations may be employed together, i.e., while outer shaft 178 is advanced, inner shaft 178 is retracted. The relative movement may be accomplished in any suitable manner, for example by way of a screw configuration, i.e., where the shaft members engage by way of corresponding threads, as illustrated in FIG. 20A, or by way of a ratchet configuration, as illustrated in FIG. 20B. The relative movement is accomplished by manual actuation of actuator 176 coupled to handle 174. While only mechanical embodiments of the movement actuation are illustrated, the same can be achieved by electrically or pneumatically-driven devices or mechanisms.

Figure 21:
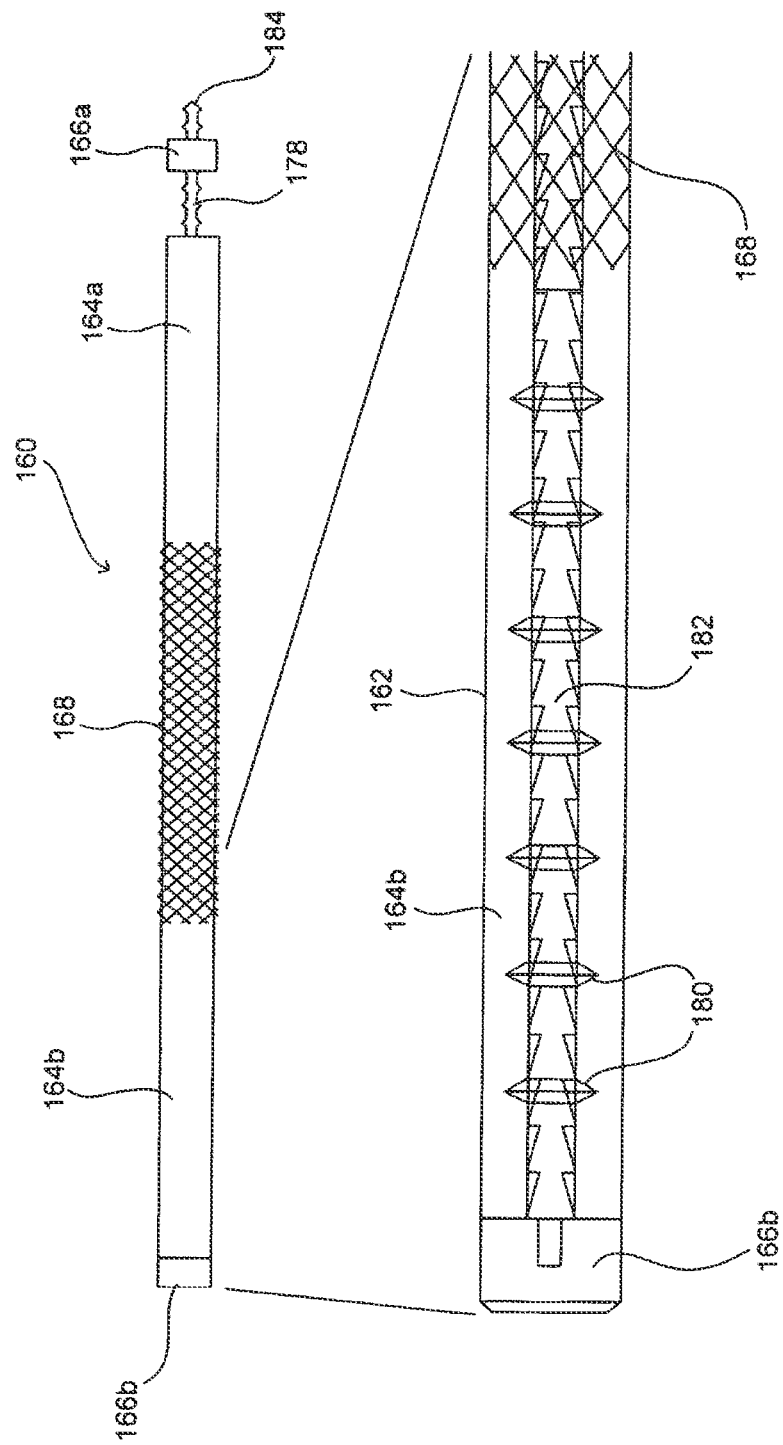
FIG. 21 illustrates a cut-away view of a distal portion of the device of FIG. 18 operably positioned over the delivery device of FIG. 20B.

As mentioned above, spacer 160 may be provided with an integrated core member or the core member may be detachably provided on the distal end 182 of inner shaft 178. In the first embodiment, distal end 182 of inner shaft 178 is configured to temporarily couple with a proximal end (i.e., the end closest to handle 174) of the core member. In the latter embodiment, the distal end 182 of inner shaft 178 is configured to be inserted into the lumen of tubular member 162, as illustrated in FIG. 21, connect to or engaged with distal hub 166b (i.e., the hub positioned furthest from handle 174) and be detachable at a proximal end 184 from inner shaft 178 to function as a core member. An advantage of the latter embodiment is that the end portion 182 of the inner shaft 178 functioning as the core member may have a length that is as short as the length of tubular member 172 when in a deployed state, with no extra length or remaining portion extending laterally of the implanted device. In the integrated embodiment, the core length may need to be as long as tubular member 172 when in the undeployed state. However, the core member may be segmented to allow for selective removal of one or more lengths or portions from the proximal side of the core member subsequent to implantation of the spacer so as not to have any excess length extending from the spacer.

With either embodiment, retraction of inner shaft 178, as described above, retracts distal hub 166b towards proximal hub 166a and/or advancement of outer shaft 172 advances proximal hub 166a towards distal hub 166b, thereby causing tubular member 162 to be compressed axially, and thus expanded radially, as shown in FIG. 198. While distal hub 166b may be fixed to tubular member 162, proximal hub 166a may be provided as a separate component having a central bore which allows it to receive and axially translate over inner shaft 178. Proximal hub 166a may be configured to readily slide over inner shaft 178 in a distal direction (but possibly not in a proximal direction) or may be threaded in order to advance over inner shaft 178. The advancement of proximal hub 166a axially compresses tubular member 172 and causes it to radially expand. The axial compression or radial expansion may be continued until the desired extent of distraction occurs between vertebrae 2 and 4. When the desired level of distraction is achieved, proximal hub 166a is secured to either the proximal end of tubular member 162 and/or the proximal end of the core member 182, such as by a threaded or snap-fit engagement or by activating a lock mechanism (not shown). Inner shaft 178 may then be released from the core member (or distal end 182 of inner shaft 178 may be released from inner shaft 178 and left within tubular member 172 to function as the core member) which, along with the end hubs 166a and 166b, maintain the implanted spacer 160 in a deployed state so as to maintain distraction between the vertebrae.

The reconfiguration of spacer 160 may be further facilitated by selectively configuring the wall of tubular member 162. For example, the interior or luminal surface of tubular member 162 may be contoured or incorporated with divets or spaces 180 where, upon compression of tubular member 162, the walls of the uncovered portions 164a, 164b of tubular member 162 will more readily fold inward to provide the resulting configuration shown in FIG. 18B.

Figure 22A:
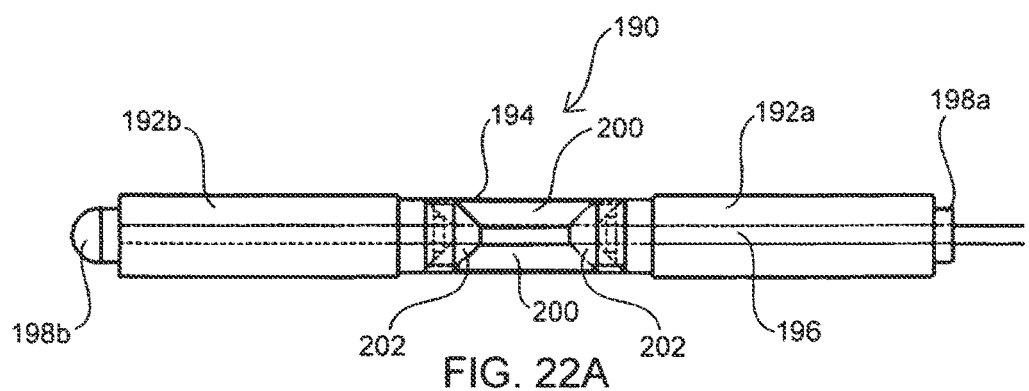
FIGS. 22A-22C illustrate another interspinous spacer device of the present invention in undeployed, partially deployed and fully deployed states, respectively.
Figure 22B:
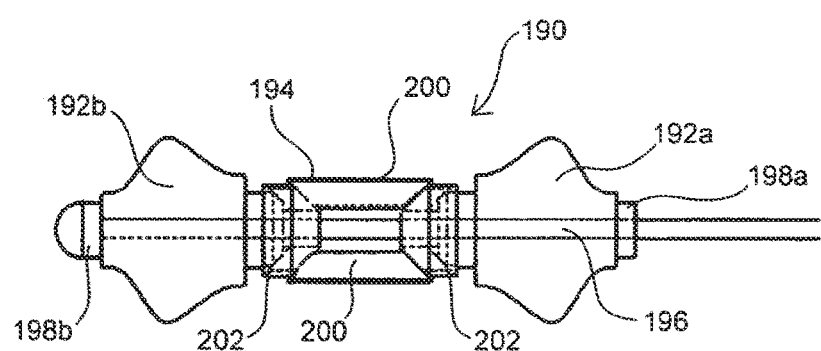
Figure 22C:
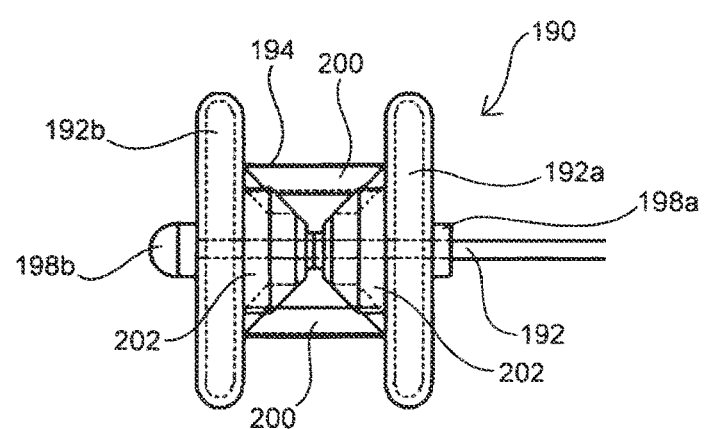

FIGS. 22A-22C illustrate another interspinous spacer 190 of the present invention in undeployed/unexpanded state, in an intermediate state during deployment and in a deployed/expanded state, respectively. Spacer 190 includes expandable end portions 192a, 192b which are capped by hubs 198a, 198b, respectively. As mentioned previously, one or both hubs may be provided fixed to the end members or may be releasably coupled thereto. Extending between end portions 192a, 192b is a central portion 194 including a plurality of blocks or wedges, such as side blocks 200 and end blocks 202, surrounded by a cover, sleeve or retaining member (not shown) which functions to hold the blocks in frictional engagement with each other. A core member or rod 196 extends centrally through end portions 192a, 192b and central portion 194 where end blocks 202 are coaxially positioned on core 196 and are slidably translatable thereon. Core member 196 or a portion thereof may be provided integrated with spacer 190 or may be provided as a detachable component of the device used to deliver and implant the spacer.

As with the previously described spacer, end portions 192a, 192b may be made of a polymer based material or any other material which allows for simultaneous axial shortening and radial expansion when compressed. Blocks 200, 202 have a more rigid configuration in order to distract the adjacent spinous processes which define the interspinous space into which spacer 190 is positioned without substantial compression of central portion 194. As such, the blocks may be made of a rigid polymer material, a metal, ceramics, plastics, or the like. In order to effect radial expansion and axial shortening of central portion 194, the blocks are selectively sized, shaped and arranged such that an inwardly compressive force on end blocks 202 along the longitudinal axis of the spacer forces end blocks 202 together which in turn forces side or lateral blocks 200 outward and away from each other, as illustrated in FIG. 22B. The inwardly tapered sides of the blocks enable slidable engagement between adjacent blocks. The covering (not shown) around the blocks is made of a stretchable material so as to accommodate the radial expansion of central portion 194. As such, the cover may be made of a polymer based material.

When in an undeployed state, as shown in FIG. 22A, the central and end portions of spacer 190 have tubular or cylindrical configurations, and may have any cross-sectional shape, length and or diameter as provided above with respect to spacer 160 of FIGS. 18A and 18B. Deployment of spacer 190 within an interspinous space may be accomplished in the manner described above. In a fully deployed state, as illustrated in FIG. 22C, spacer 190 has a dumbbell or H-shaped configuration with a change in length and height dimensions as provided above. The increased diameter of central portion 194 when spacer 190 is the deployed configuration distracts the adjacent vertebrae so as to provide pain relief. While the respective dimensions of the spacers change from an undeployed to a deployed state, the spacers may be configured such that the overall size of volume occupied by the spacer does not change.

Figure 23A:
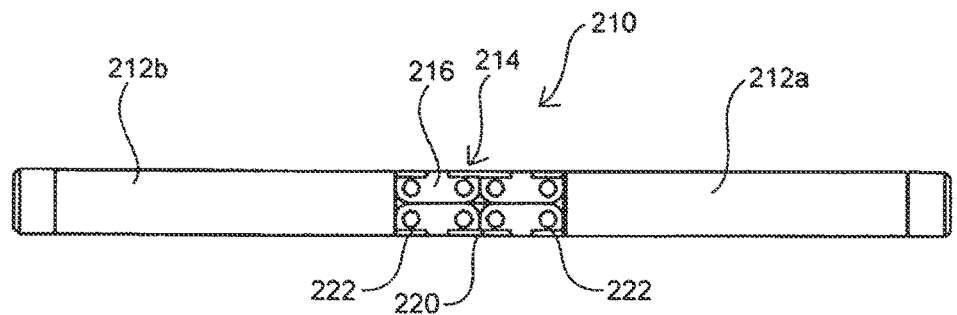
FIGS. 23A-23C illustrate another interspinous spacer device of the present invention in undeployed, partially deployed and fully deployed states, respectively.
Figure 23B:
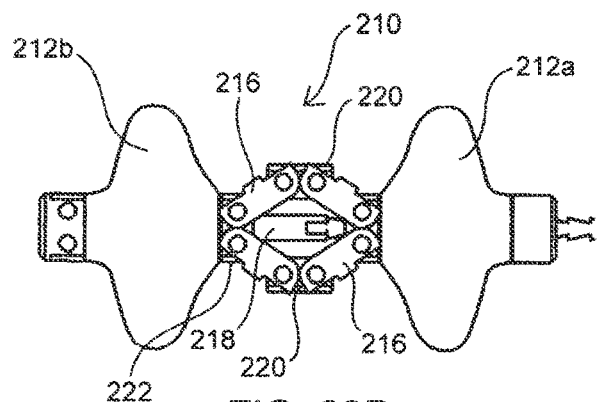
Figure 23C:
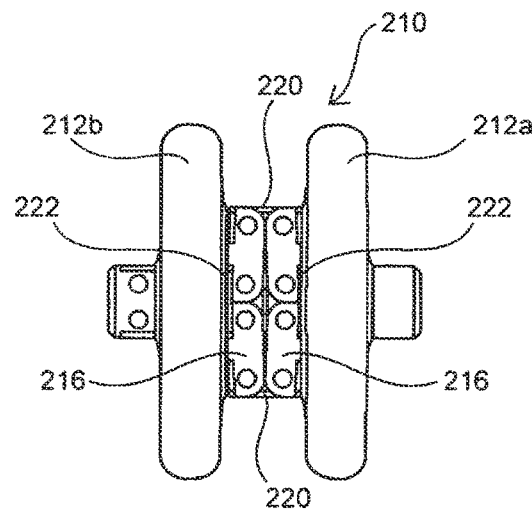

Another interspinous spacer 210 of the present invention is illustrated in an undeployed/unexpanded state, in an intermediate state during deployment and in a deployed/expanded state in FIGS. 23A-23C, respectively. Spacer 210 includes expandable end portions 212a, 212b capped by hubs 224a, 224b, respectively: As mentioned previously, one or both hubs may be provided fixed to the end members or may be releasably coupled thereto. Extending between end portions 212a, 212b is a central portion 214 including a plurality of linkages 216 and blocks 220, 222, which collectively provide opposing struts. Each linkage 216 has a length and is pivotally coupled to a side block 220 and an end block 222, where end blocks 222 are coaxially positioned on core 218 and are slidably translatable thereon. While the materials and configuration of end portions 212a, 212b may be as described above, linkages 216 are preferably made of a metal material. A core member or rod 218 extends centrally through end portions 212a, 212b and central portion 214. Core member 218 or a portion thereof may be provided integrated with spacer 210 or may be provided as a detachable component of the device used to deliver and implant the spacer.

In an undeployed state, as shown in FIG. 23A, the central and end portions of spacer 190 have tubular or cylindrical configurations, and may have any cross-sectional shape, length and or diameter as provided above. As such, side blocks 220 are close together and end blocks 222 are spaced apart with the lengths of linkages 216 aligned with the longitudinal axis of core member 218. When opposing, inwardly compressive forces are exerted on spacer 210 along its longitudinal axis, end portions 212a, 212b axially compress and radially expand as described above thereby forcing end blocks 222 together which in turn force side or lateral blocks 220 outward and away from each other, as illustrated in FIG. 23B. This action causes linkages 216 to spread apart, as shown in FIG. 23B, and move to positions where their lengths are transverse to the longitudinal axis of core 218, as illustrated in FIG. 23C.

Figure 24A:
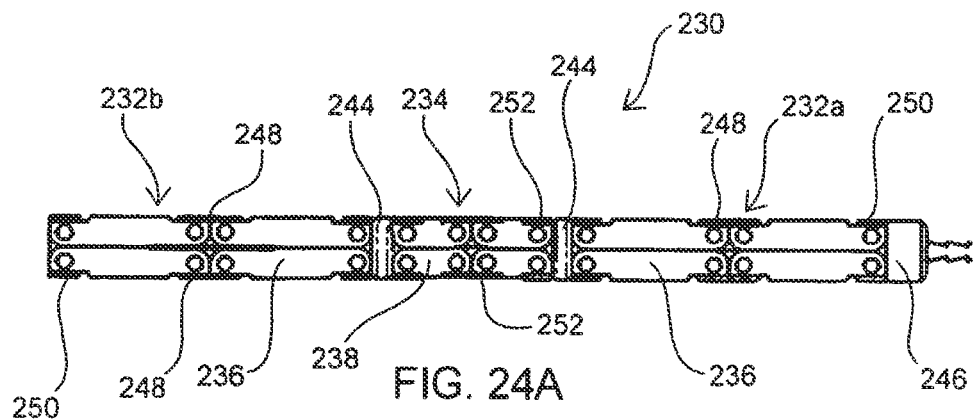
FIGS. 24A-24C illustrate yet another interspinous spacer device of the present invention in undeployed, partially deployed and fully deployed states, respectively.
Figure 24B:
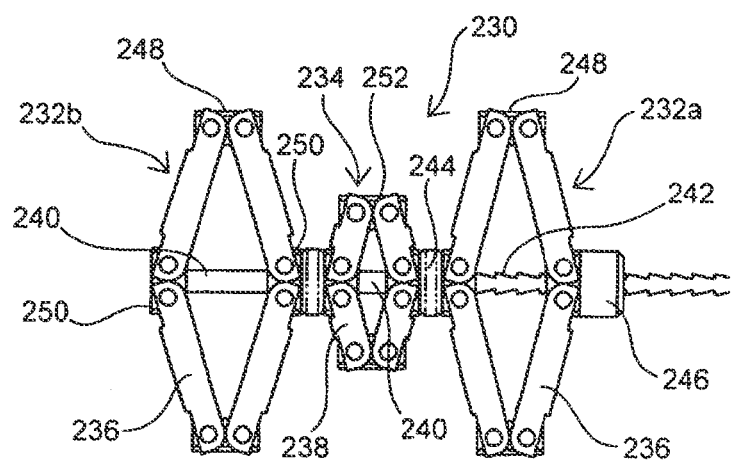
Figure 24C:
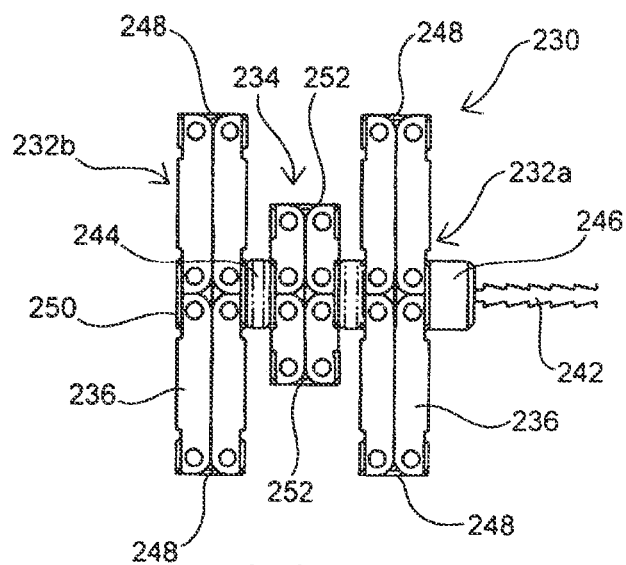

Interspinous spacer 230 of FIGS. 24A-24C employs the linkage arrangement of the central portion of spacer 190 of FIGS. 23A-23C in both of its end portions 232a, 232b as well as its central portion 234. Specifically, end portions 232a, 232b employ linkages 236, which are longer than linkages 238 used for central portion 234, but which are arranged in similar engagement with side blocks 248 and end blocks 250. On each side of central portion 234 and in between the central portion and the end portions 232a, 232b, respectively, are dampening washers 244. A core member 240 extends between and through the end blocks 250 of distal end member 232a and the end blocks 252 of central portion 234 as well as the dampening washers 244 positioned therebetween, all of which, except the most distal end block, may slidably translatable along core member 240. Core member 240 is releasably attached at a proximal end to ratcheted drive rod 242 of a delivery device as discussed above with respect to FIGS. 19-21 which rod 242 extends through the proximal end portion 232a and hub 246, as illustrated in FIG. 24B.

In an undeployed state, as shown in FIG. 24A, the central and end portions of spacer 230 have tubular or cylindrical configurations. As such, side blocks 248 and 252 of end portions 232a, 232b and central portion 234, respectively, are close together and end blocks 250 and 252 of end portions 232a, 232b and central portion 234, respectively, are spaced apart with the lengths of linkages 236, 238 aliped with the longitudinal axis of core member 240. When opposing, inwardly compressive forces are exerted on the distal block 250 and hub 246 of spacer 230 along its longitudinal axis, the end blocks are drawn together thereby forcing side or lateral blocks 220 outward and away from each other, as illustrated in FIG. 24B. This action causes the linkages of the end and central portions to spread apart, and move to positions where their lengths are transverse to the longitudinal axis of core 240, as illustrated in FIG. 24C, the fully deployed state of spacer 230.

Figure 25A:
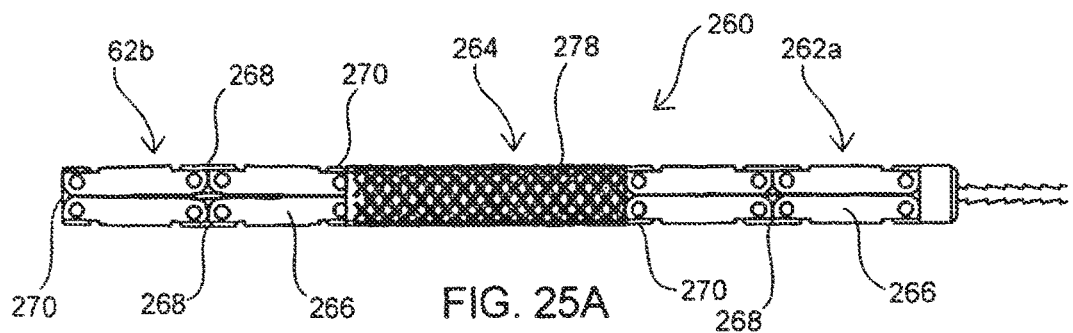
FIGS. 25A-25C illustrate another interspinous spacer device of the present invention in undeployed, partially deployed and fully deployed states, respectively.
Figure 25B:
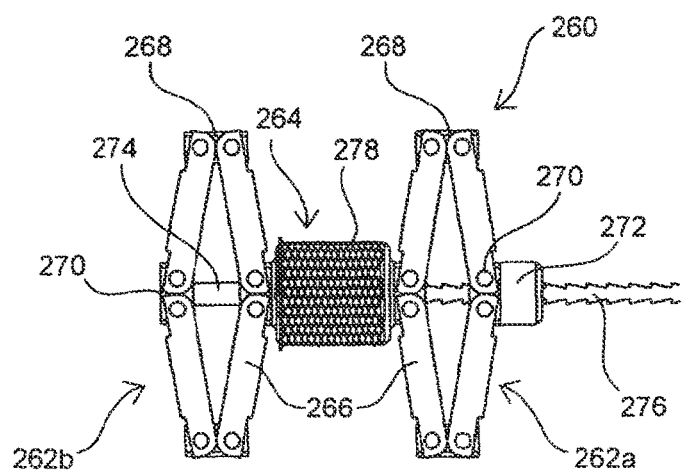
Figure 25C:
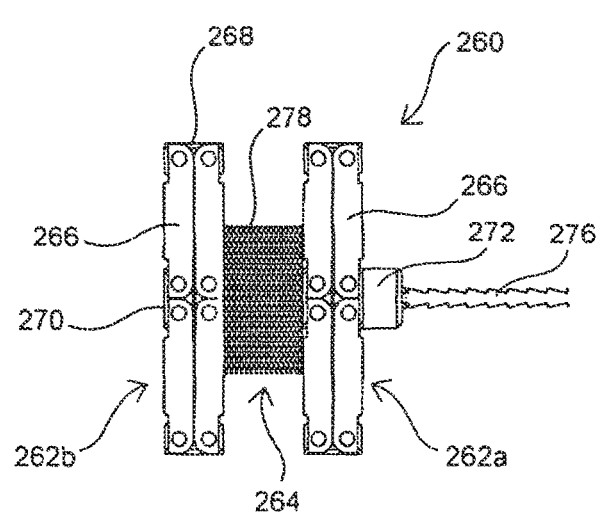

The end portions and central portions of the compressible spacers described above may be used in any combination. For example, the polymer-based central portion of FIGS. 18A and 18B and the linkage end portions of FIGS. 24A-24C may be used together to form a spacer of the present invention. Such a spacer 260 is illustrated in FIGS. 25A-25C. Spacer 260 includes linkage-block end portions 262a, 262b and a compressible central member 264 around which is positioned a circumferential retaining member 278 made of a braided mesh-like material. A core member 274 extends between and through the end blocks 270 of distal end member 262a and through central portion 264, all of which, except the most distal end block, may slidably translatable along core member 260. Core member 260 is releasably attached at a proximal end to ratcheted drive rod 272 of a delivery device as discussed above with respect to FIGS. 19-21 which rod 272 extends through the proximal end portion 262a and hub 272, as illustrated in FIG. 25B.

In an undeployed state, as shown in FIG. 25A, the central and end portions of spacer 230 have tubular or cylindrical configurations. As such, side blocks 268 of end portions 262a, 262b are close together and end blocks 270 of end portions 262a, 262b are spaced apart with the lengths of linkages 266 aligned with the longitudinal axis of core member 274. When opposing, inwardly compressive forces are exerted on the distal block 270 and hub 272 of spacer 260 along its longitudinal axis, the end blocks are drawn together thereby causing linkages 266 of the end portions to spread apart thereby forcing side or lateral blocks 268 outward and away from each other, as illustrated in FIG. 25B, until linkages 266 move to positions where their lengths are transverse to the longitudinal axis of core 274, as illustrated in FIG. 25C, the fully deployed state of spacer 260.

Each of the expandable and or inflatable interspinous spacers described thus far is particularly configured to be delivered minimally invasively, even percutaneously, from a single incision located laterally to one side (left or right) of the spinal motion segment to be treated. However, the present invention also includes interspinous spacers which are deliverable through a mid-line incision made directly into the interspinous ligament. Examples of such spacers are now described.

Figure 26A:
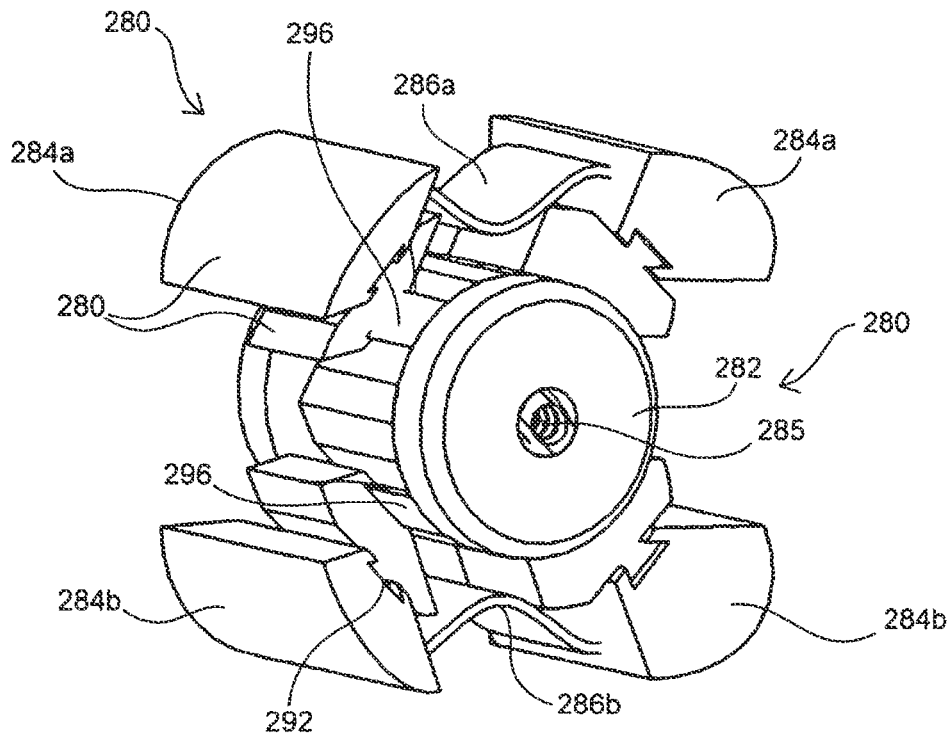
FIGS. 26A and 26B illustrate perspective and front views of another interspinous spacer device of the present invention in a deployed state.
Figure 26B:
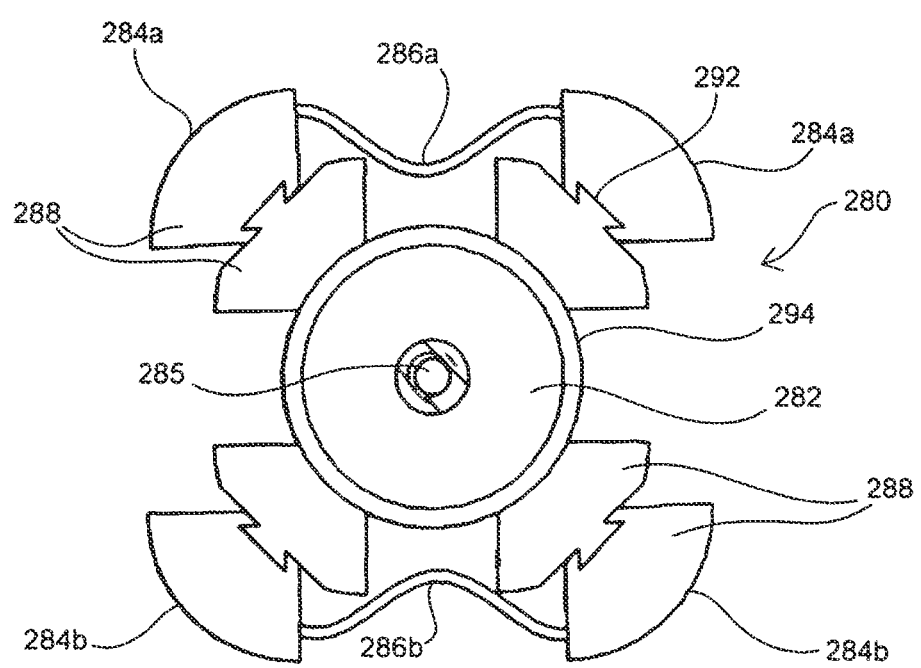
Figure 27:
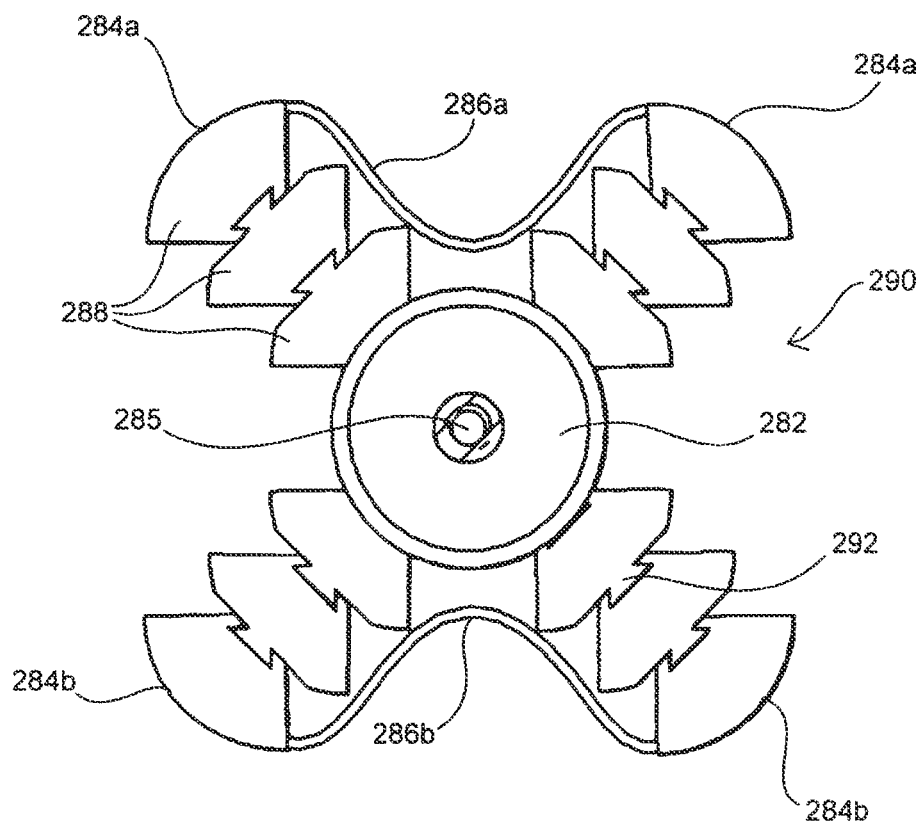
FIG. 27 illustrates a front view of another interspinous spacer device of the present invention.

FIGS. 26A and 26B are perspective and front views, respectively, of interspinous spacer 280 which is configured for implantation by way of a percutaneous mid-line approach. Spacer 280, shown in a deployed state, includes a central member or portion 282 and four struts or legs 284 which are substantially radially expandable from central portion 282. Central portion 282 has a cylindrical configuration having a diameter sized for delivery through a small gauge cannula and a length that allows placement within an interspinous space. A lumen 285 extends at least partially through the center of central portion 282 and is configured, e.g., threaded, to be releasably engaged to a delivery tool.

Each strut 284 includes one or more blocks 288. Where more than one block 288 per strut is employed, such as with spacer 280 which employs two blocks 288 per strut 284 and spacer 290 of FIG. 27 which employs three blocks 288 per strut 284, the blocks are stacked and slidably interconnected to each other in a manner that allows the to translate linearly relative to each other along parallel axes. A tongue and groove configuration 292 is employed with the illustrated embodiment to interconnect stacked blocks, but any suitable interconnection which enables such relative motion between the blocks may be used. Such configuration may also be employed to interconnect the innermost block to central member 282 where outer ridges or tongues 296 on central member 282 slidably interface with a corresponding groove on inner end of the innermost block. As such, blocks 288 are slidable relative to central member 282 along an axis parallel to the longitudinal axis of central member 282. Depending on the application and the particular anatomy of the implant site, struts 284 may be evenly spaced apart about the circumference of central member 282. In other embodiments the distance between superior struts 284*a* and between inferior struts 284*b* may vary and/or the distance between each of those and between struts on the same side of the central member may vary.

Spanning between each strut pair 284*a* and 284*b* is a strap 286*a* and 286*b*, respectively, affixed to the outermost blocks. Straps 286 may be made of any suitable material which is strong enough to maintain distraction between adjacent spinous processes and to endure any frictional wear which it may undergo due to natural spinal motion. The straps may be flexible such that they act as slings, or may be conformable to the spinous processes once in situ. Alternatively, the straps may be non-conforming and rigid with a planar or curved shape depending on the application at hand. Suitable strap materials include but are not limited to polyester, polyethylene, etc.

With reference to FIGS. 28A-28E, various steps of a method according to the present invention for implanting spacer 280 as well as other spacers of the present invention configured for a mid-line implantation approach into a target spinal motion segment (defined by components of vertebral bodies 2 and 4) of a patient are described.

The initial steps of creating a percutaneous puncture and subsequent penetration into the skin 30 and the dissection of the spinous ligament 54 involve many of the same instruments (e.g., K-wire, trocar, cutting instrument, delivery cannula, etc.) and surgical techniques used in the ipsolateral implantation approach described above with respect to FIGS. 5 and 6. Upon creating an opening within the interspinous space extending between the superior spinous process 18 and the inferior spinous process 22, a delivery instrument 300 having interspinous device 280 operatively preloaded in undeployed state at a distal end is delivered to within the interspinous space. The delivery instrument 300 is provided with a mechanism for releasably connecting to spacer 280, such as by way of threaded screw 302 (see FIG. 28D) which is threadedly engaged with threaded lumens 285 of spacer 280.

Figure 28A:
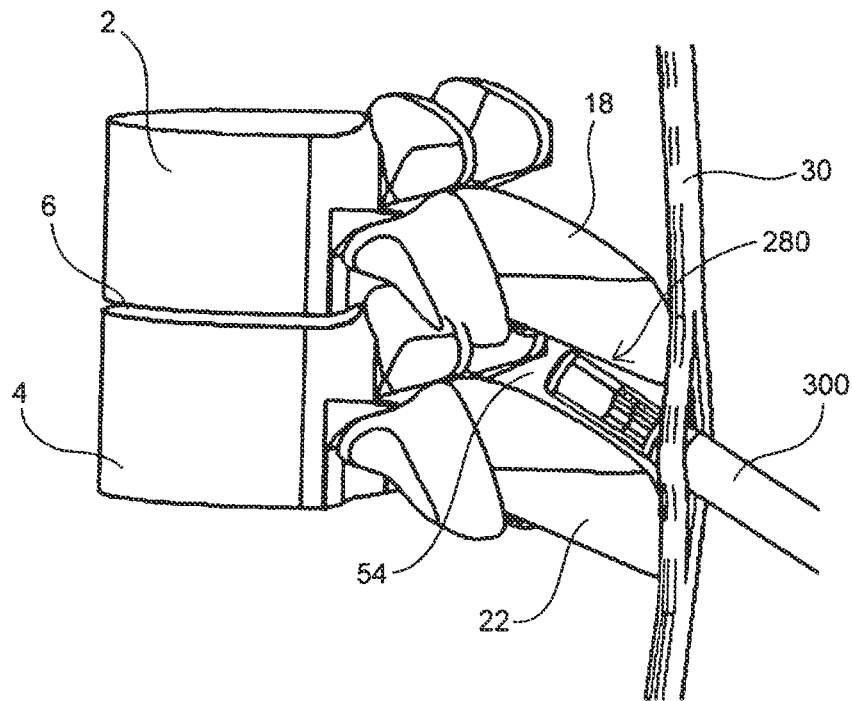
FIG. 28A illustrates a step in a method of implanting the interspinous spacer device of FIGS. 26A and 26B.
Figure 28A:
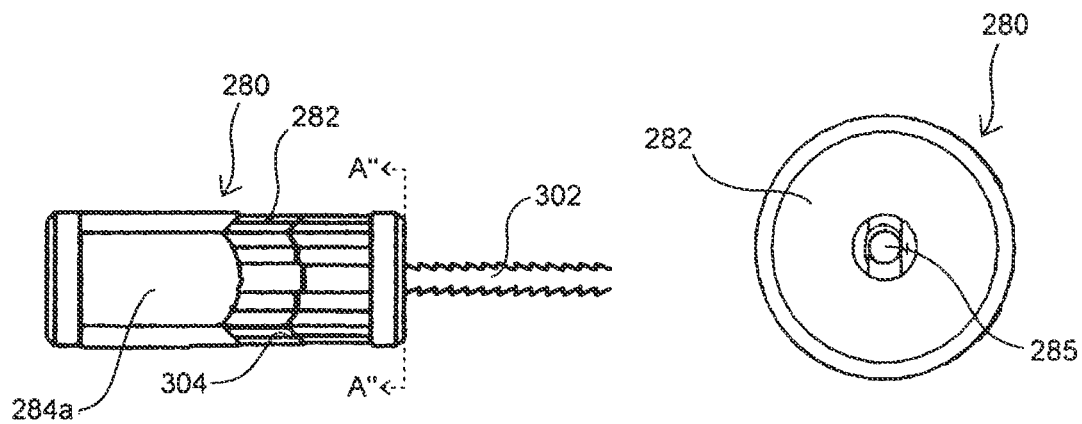

As best illustrated in FIGS. 28A' and 28A", when in an undeployed state, spacer 280 has a relatively low profile to facilitate entry into the interspinous space. Once properly positioned within the interspinous space, deployment of the spacer 280 is initiated, as illustrated in FIG. 28B, by manipulation of instrument 300 which simultaneously causes outward radial movement of the outermost blocks of strut pairs 284*a*, 284*b* and distal linear advancement of the proximal portion 304 of spacer 282 (see FIGS. 28B' and 28B") resulting in radial expansion and axial shortening of spacer 280. Spacer 280 may be configured such that deployment of the struts is accomplished by either or both axial rotation of internally componentry or axial compression of central member 282.

As the struts are radially extended, straps 286*a* and 286*b* emerge and they become tauter as the slack in them is gradually reduced by the extension of the struts. Continued deployment of spacer 280 causes straps 286*a*, 286*b* to engage with opposing surfaces of spinous processes 18 and 22. The radial extension of the struts is continued, as illustrated in FIGS. 28C, 28C' and 28C", until the desired amount of distraction between the vertebra is achieved. This selective distraction of the spinous processes also results in distraction of the vertebral bodies 2, 4 which in turn allows the disk, if bulging or distended, to retract to a more natural position. The extent of distraction or lordosis undergone by the subject vertebrae can be monitored by observing the spacer under fluoroscopy.

Figure 28D:
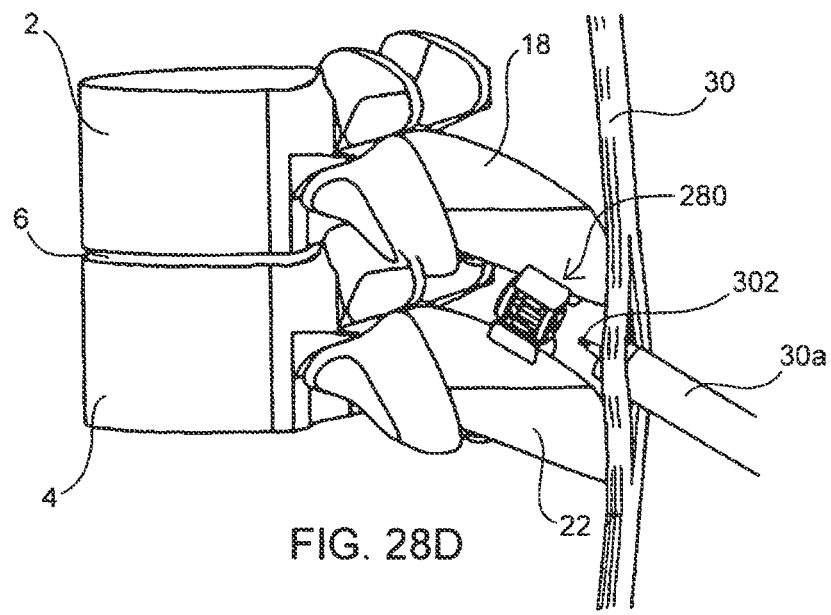
FIG. 28D illustrates a step in a method of implanting the interspinous spacer device of FIGS. 26A and 26B in which the spacer is fully deployed and being released from a delivery device.
Figure 28E:
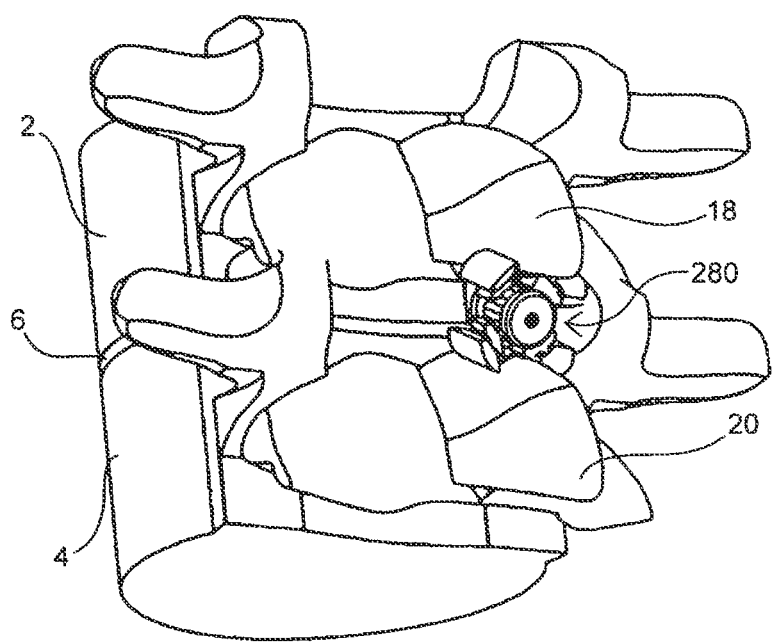
FIG. 28E illustrates the interspinous spacer device of FIGS. 26A and 26B operatively implanted within an interspinous space.

At this point, the delivery instrument 300 is released from spacer 280 by unscrewing threaded screw 302 from threaded lumen 285 and removing it from the implant site, as illustrated in FIG. 28D. Spacer 280 remains behind within the interspinous space, locked in a deployed state (see FIG. 28E).

Spacer 280 may configured such that the struts are not retractable without active manipulation of delivery instrument 300 to ensure that their extension, and thus the distraction on the spinal motion segment, is maintained. As configured, spacer 280 may be easily repositioned or removed by subsequent insertion of instrument 300 into the interspinous space and operative engagement with the spacer. Instrument 300 is then manipulated to cause retraction of the struts and the straps, reducing the spacer's profile to allow repositioning or removal of the spacer.

Figure 29C:
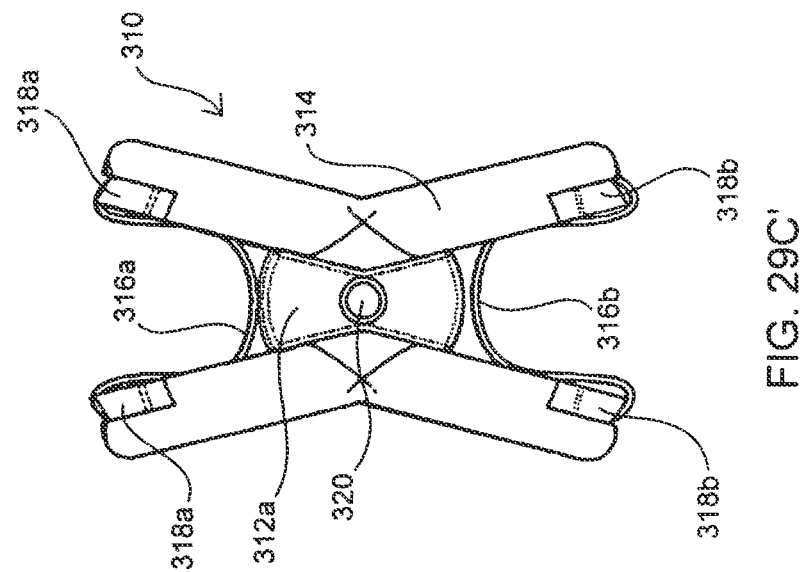
FIGS. 29A and 29A illustrate perspective and front views of another interspinous spacer device of the present invention in an undeployed state.
FIGS. 29B and 29B' illustrate perspective and front views of the interspinous spacer device of FIG. 29A in a partially deployed state, FIGS. 29C and 29C' illustrate perspective and front views of the interspinous spacer device of FIG. 29A in a partially deployed state but one which is more deployed than depicted in FIG. 29B.
FIGS. 29D and 29D' illustrate perspective and front-views of the interspinous spacer device of FIG. 29A in a fully deployed state.
Figure 29C:
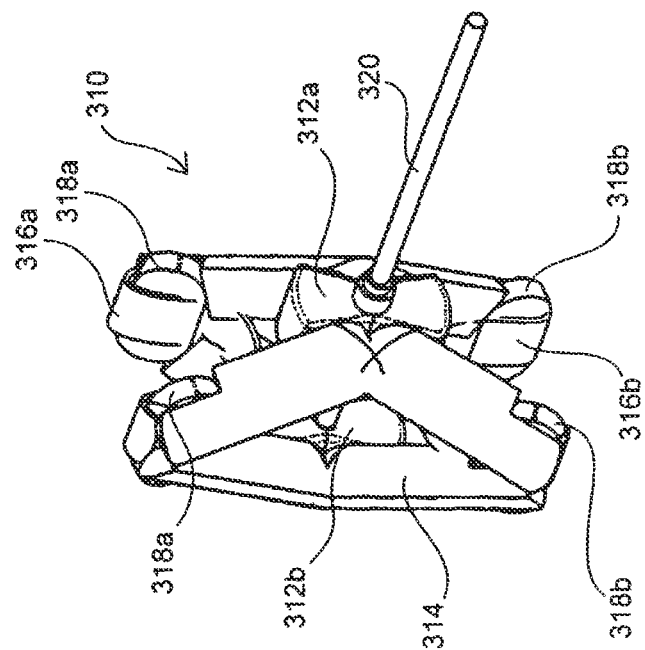
Figure 29D:
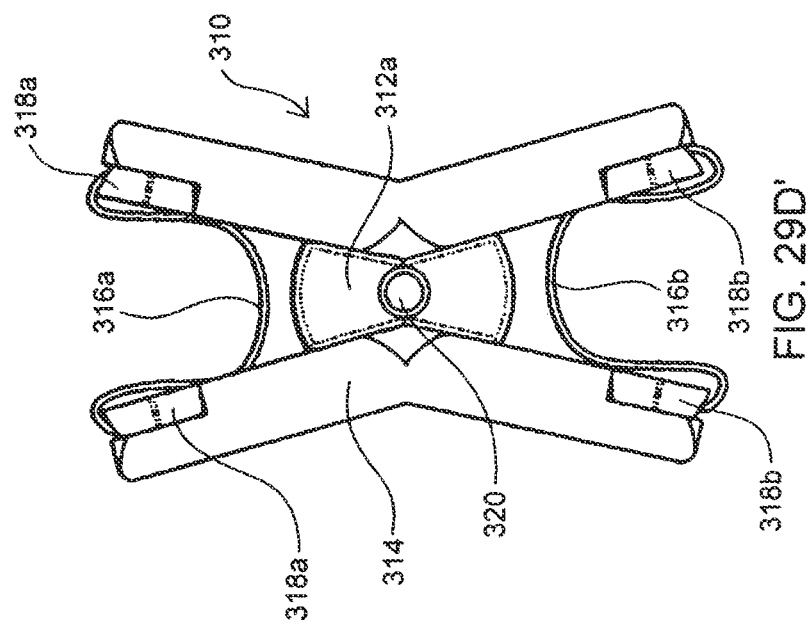
Figure 29D:
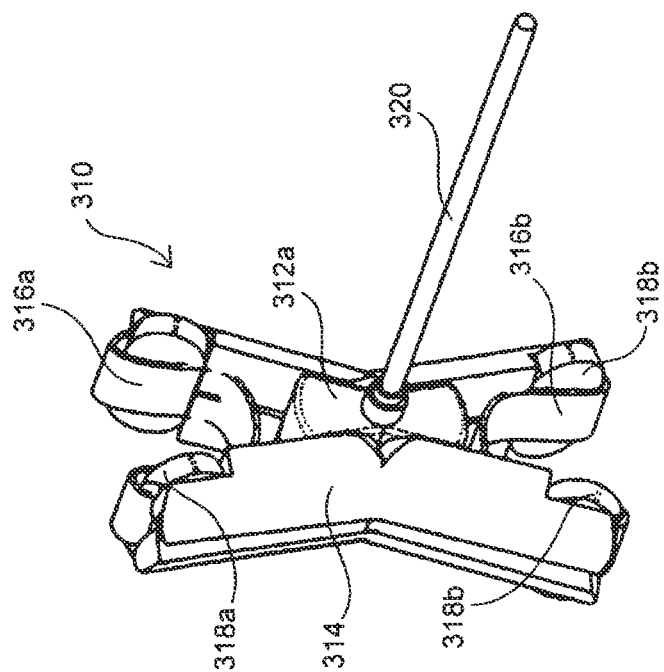

FIGS. 29A-29D illustrate another spacer 340 of the present invention that is implantable through a mid-line approach to the interspinous space. Spacer 310 includes centrally opposed front and rear structures or blocks 312*a*, 32*b* which are pivotally interconnected on both sides to pairs of elongated linkages 314. The other end of each linkage 314 is pivotally connected to a lateral structure 318*a* or 318*b*. The resulting "X" configuration provides interconnected strut pairs on each side of spacer 310 which move and function similarly to the linkages described above with respect to the spacers illustrated in FIGS. 23, 24 and 25, i.e., the lengths of linkages 314 extend parallel to the central axis of spacer 310 when in a fully undeployed state (FIG. 29A) and extend transverse to the central axis of spacer 310 in a fully deployed state (FIG. 29D). Extending between opposing superior lateral structures 318*a* and between opposing inferior structures 318*b* are straps 316*a* and 316*b*, respectively.

Spacer 310 is implantable and deployable by way of a mid-line approach similar to that described above with respect to the spacer of FIGS. 28A-28E. Spacer 310 is preloaded to a delivery instrument shaft 320 which is insertable and axial translatable through a central opening within front block 312*a*. The distal end of shaft 320 is releasably attached to an axial member (not shown) of spacer 310. Axial member is fixed to rear block 312*h* and extends along the central axis of spacer 310, having a length which extends to front block 312*a* when spacer 210 is in a fully deployed state, as illustrated in FIG. 29D but which extends only a portion of the length of spacer 310 when it is in an undeployed state (FIG. 29A) or a partially undeployed (FIGS. 29B and 29C) state.

After the necessary space is created within the interspinous space as described above, spacer 310, which is releasably connected to delivery shaft 320 as described above, is inserted into the space in a fully undeployed sate (see FIGS. 29A and 29A'). Deployment of the spacer is accomplished by proximally pulling on shaft 320 which compresses rear block 312*b* towards front block 312*a*. This in turn causes the linkages 314 to pivot about their respective attachment points with superior and inferior lateral structures or blocks 318*a* and 318*b* forced away from each other, as illustrated in FIGS. 29B and 29B'. Continued pulling of instrument 320 further expands linkages 314 in a direction transverse to the central axis of spacer 310 and extend straps 316*a*, 316*b* towards respective surfaces of the spinous processes. As front and rear blocks 312*a* and 312*b* are centrally tapered, defining a bowtie or hourglass configuration, the strut pairs define a centrally tapered profile as the align to their fully deployed position, as best shown in FIGS. 29C' and 29D'. In the fully deployed state, the spacer's axial member is positioned within the opening of front block 312a and locked to it. Additionally, straps 316a and 316b are firmly engaged against the spinous processes and the contacted vertebra are distracted from each other. Delivery instrument 320 may then be released from spacer 310 and removed from the implant site.

Figure 30A:
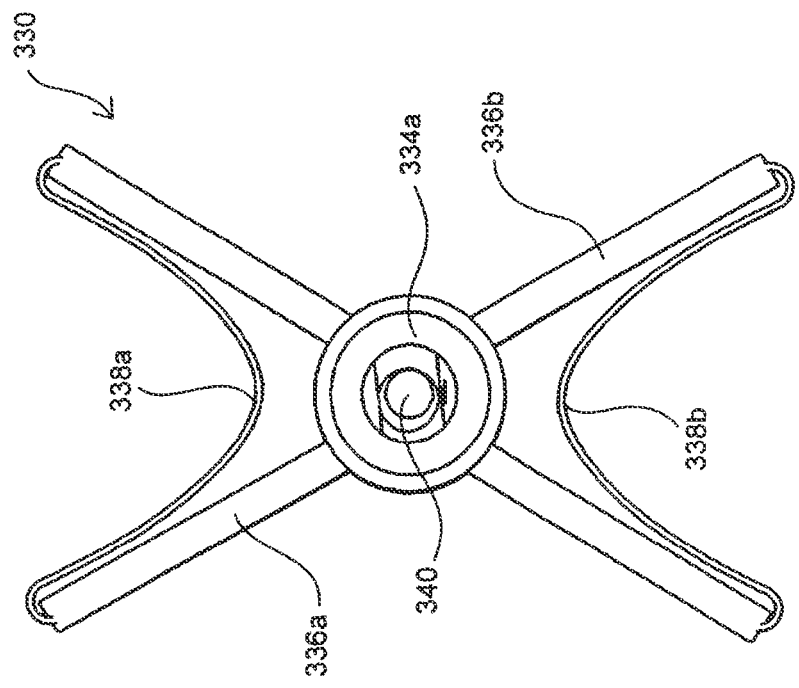
FIGS. 30A and 30A' illustrate perspective and front views of another interspinous spacer device of the present invention in a fully deployed state.
Figure 30A:
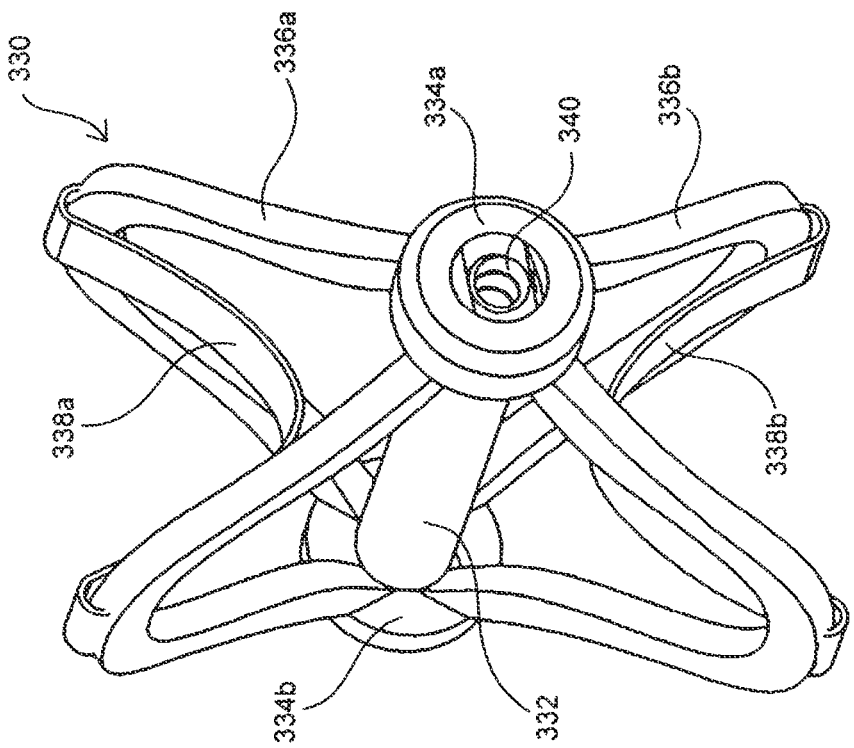
Figure 30B:
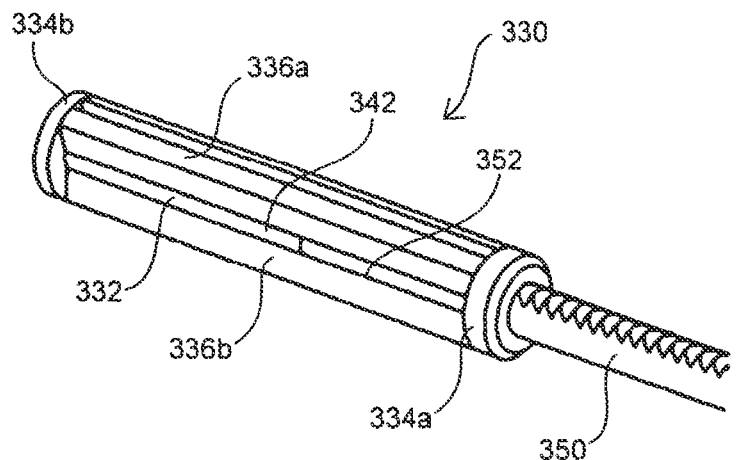
FIGS. 30B and 30B' illustrate perspective and side views of the interspinous spacer device of FIG. 30A in an undeployed state.
Figure 30B:
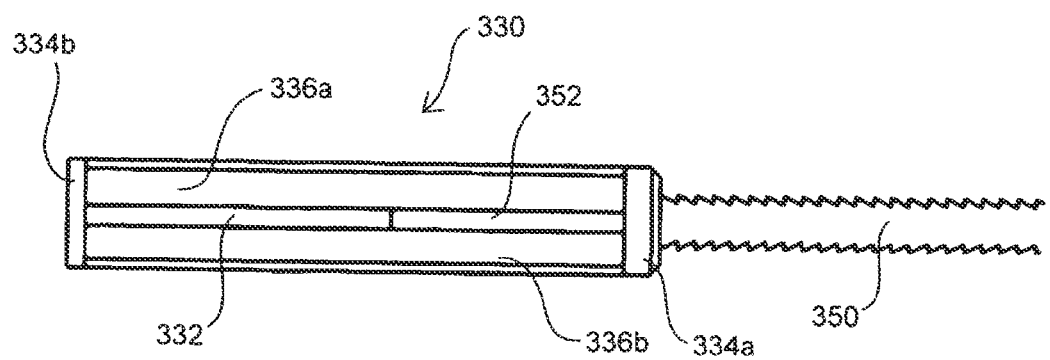
Figure 30C:
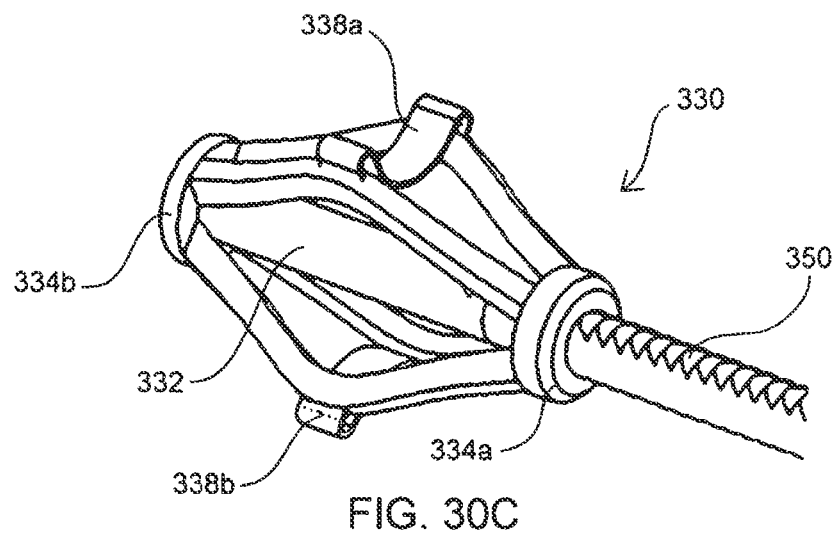
FIGS. 30C and 30C' illustrate perspective and side views of the interspinous spacer device of FIG. 30A in a partially deployed state.
Figure 30C:
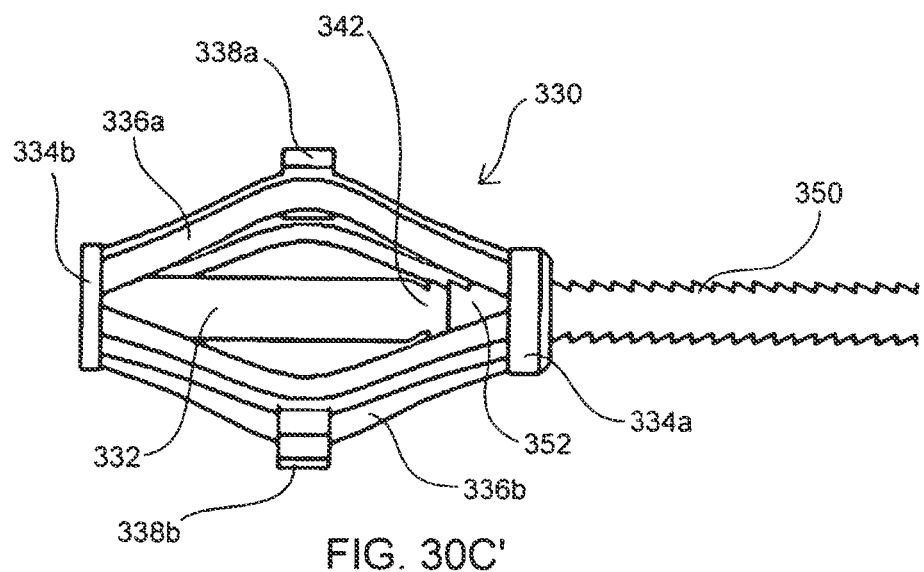

FIGS. 30A-30C illustrate yet another spacer 330 of the present invention having an "X" shape in an expanded condition and which is implantable through a mid-line approach to the interspinous space. As best illustrated in FIGS. 30A and 30A', spacer 330 includes an elongated central member 332 extending between front and rear hubs 334a and 334b and a plurality of flexible or deformable struts 336 which also extend between hubs 334a, 334b. Struts 336 are configured to be deformable and to have a directional character to facilitate deployment of them radially outward from central member 332. Examples of suitable constructs of these struts include but are not limited to thin metal plates, e.g., flat springs, wire bundles or a polymer material. Extending between and affixed to each of strut pairs 336a and 336b are straps 338a and 338b, respectively.

The proximal end 342 of central member 332 is provided with ratcheted grooves which are releasably engaged within the distal end of 352 of delivery instrument 350 (see FIG. 30C). Front hub 334a is provided with an opening 340 which also has a grooved internal surface for engaging with the grooves of central member 332.

Figure 2A:
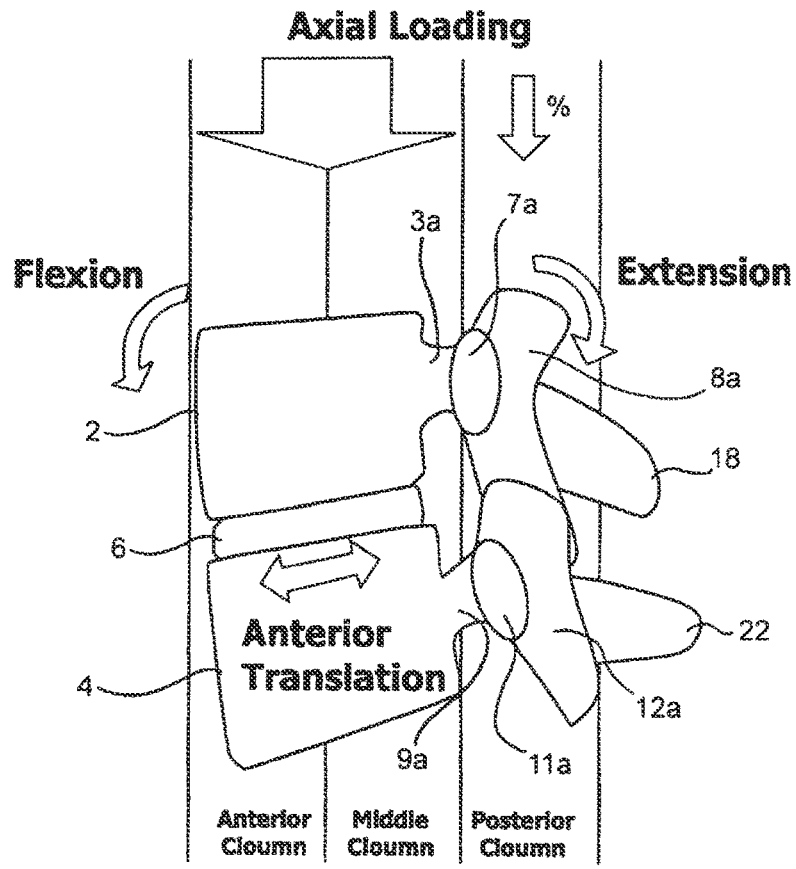
FIGS. 2A, 2B and 2C illustrate left side, dorsal and top views, respectively, of the spinal segments of FIG. 1A under going various motions.
Figure 2B:
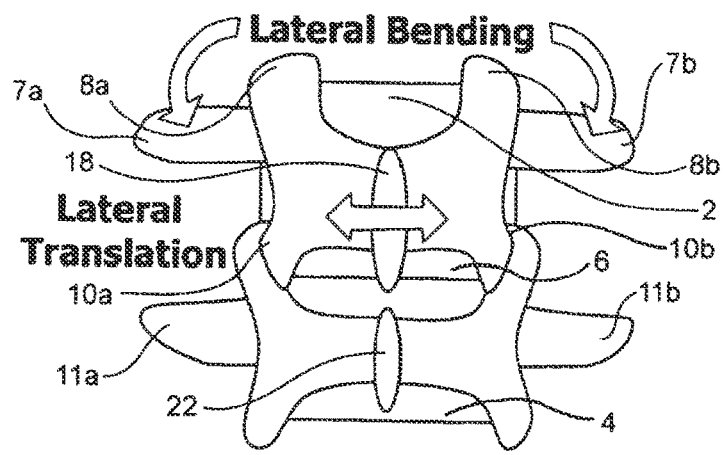
Figure 2C:
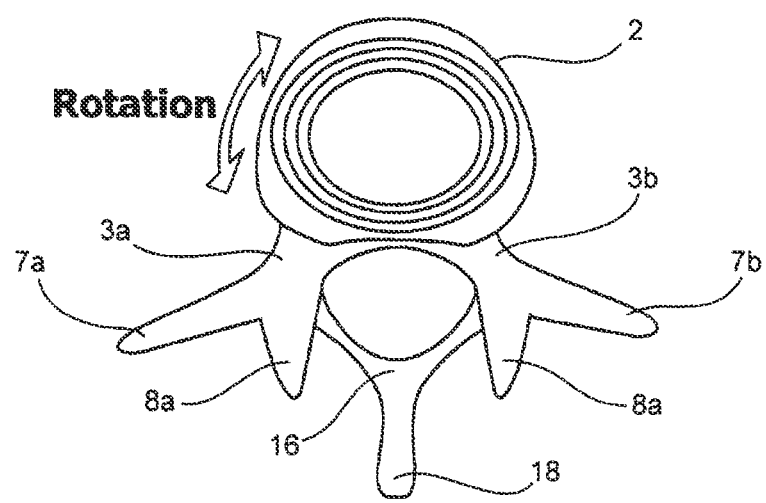

Spacer 330 is implantable and deployable by way of a mid-line approach similar to that described above with respect to the spacer of FIGS. 29A-2D. Spacer 330 is preloaded in a fully undeployed state to delivery instrument shaft 350 as illustrated in FIGS. 30B and 30B'. After the necessary space is created within the interspinous space as described above, spacer 330 is inserted into the interspinous space. Deployment of the spacer is accomplished by proximally pulling on shaft 350, by ratcheting as described above, which compresses rear hub 334b towards front hub 334a or distally pushing on front hub 334a towards rear hub 334b. This in turn causes struts 336a, 336b to flex or bend outward, as illustrated in FIGS. 30C and 30C'. Continued pulling of instrument 350 (or pushing of hub 334a) further bends the struts such that they define an X-shaped structure with straps 338a and 338b forcably abutting against the interspinous processes. The pulling (or pushing) action advances the grooved proximal end 342 of central member 332 into grooved opening 340 of front hub 334a. The opposing grooves of the central member and the opening provide a ratchet relationship between the two whereby central member is readily translatable in a proximal direction but not in a distal direction, thereby locking spacer 330 in a deployed state. Upon achieving the desired amount of distraction between the vertebra, delivery instrument 350 is released from spacer 310 (such as by unscrewing) and removed from the implant site.

FIGS. 31A and 31B illustrate a stabilizing spacer 360 similar to spacer 330 just described but which forms the expanded "X" configuration with solid linkages rather than struts. Spacer 360 includes an elongated central member 362 extending from and fixed to a rear hub 364a and slidably through a front hub 364b proximally to a delivery tool having a shaft 372. Also extending between the front and rear hubs are four linkage pairs, where each linkage pair 366a and 366b are interconnected to a respective hub by a hinge 368 and are interconnected to each other by a hinge 370. When in a fully unexpanded condition, each linkage pair extends parallel to central member 362, providing a low profile for delivery. When the front and rear hubs are caused to approach each other, each linkage pair 366a, 366b expands substantially radially outward from central member 362, as illustrated in FIG. 31A. The hubs are brought together to the extent desired to provide an expanded "X" configuration, as illustrated in FIG. 31B. Upon achieving the desired expansion, central member 362 is released or detached from delivery shaft 372. As with many of the "mechanical" type spacers discussed above, attachment and release of the spacer from the delivery device may be accomplished by various means, including but not limited to ratchet, threaded or quick-release configurations between the spacer and the delivery device.

Extending between and affixed to each of the top and bottom linkage pairs are brackets or saddles 374 for receiving the inner surfaces of opposing interspinous processes. Brackets 374 have a substantially rigid and flat central portion 374a and relatively flexible lateral portions 374b which are affixed to hinges 370. The rigid, flat central portion 374a facilitates engagement with the interspinous process. The flexible lateral portions 374h and their hinged connections to spacer 360 facilitate folding of the lateral portions 374b when in an undeployed state and allow for adjustment of spacer 360 once in a deployed state, where a least a portion of the adjustment may be self-adjustment by spacer 360 relative to interspinous space into which it is implanted.

Figure 32A:
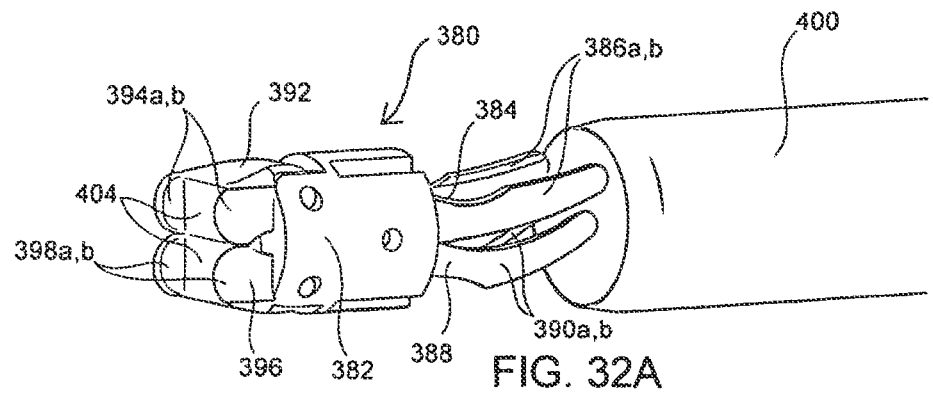
FIGS. 32A-32C illustrate another stabilizing device of the present invention deliverable through a posterior midline approach, where the device is shown in various configurations undergone during implantation and deployment of the device.
Figure 32B:
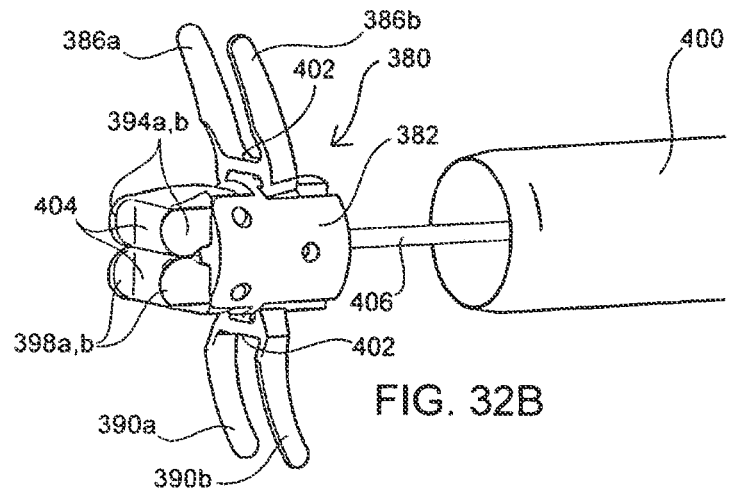
Figure 32C:
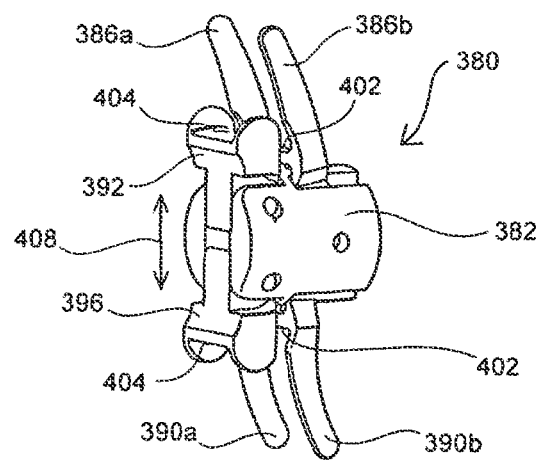

FIGS. 32A-32C illustrate another spacer 380 configured for delivery through a percutaneous posterior or midline approach having a main body, hub or block element 382. Hub 382 has a cross-sectional size and shape (e.g., cylindrical, oval, geometric, triangular, etc.) that allows for implantation between adjacent spinous processes and facilitates delivery through a narrow port or cannula 400. In this example, spacer 380 further includes four extension members or four sets of extension or arm pairs 384, 388, 392, 396, each member or pair of arms of which is movable between an undeployed or collapsed state (FIG. 32A) and a deployed or expanded state (FIGS. 32B and 32C). In the undeployed state, the extension member or arm pairs are "folded" and aligned generally or substantially axially to the translation path into the interspinous space (i.e., axially with the longitudinal axis defined by body 382), or otherwise characterized as substantially transverse to the spine's axis (when spacer 380 is operatively implanted), to provide a minimized profile (e.g., a minimized radial profile with respect to the longitudinal axis defined by body 382). In the deployed state, the extension member or arm pairs are positioned generally or substantially transverse to the collapsed position (i.e., transverse to the longitudinal axis defined by body 382 or to the translation path into the interspinous space) and substantially parallel to the spine's axis (when spacer 380 is operatively implanted).

Two of the extension pairs (384 and 388) are positioned at a proximal end or side of hub 382 (i.e., "proximal" being defined as that which is closest to the physician user during delivery of the device) and are "folded" in a proximal direction when in an undeployed state. The other two extension pairs (392 and 396) are positioned at a distal end or side of hub 382 and are "folded" in a distal direction when in an undeployed state. Proximal extension members 384, 388 may be interconnected to body 382 and/or to each other in a manner which enables them to be moved simultaneously or independently of each other. The same may be true for the distal extension members 392, 396.

Proximal extension members 384 and 388 each include two elongated arms or extensions 386a, 386b and 390a, 390b, respectively, which extend substantially parallel to each other. Extending between each proximal arm pair is a saddle strut, bridge, bracket or saddle 402. Similarly, distal extension members 392 and 396 each include two extensions 394a, 394b and 398a, 398b, respectively, which extend substantially parallel to each other. Extending between each distal extension pair is a saddle, strut or bridge 404. The resulting "U" configurations enable device 380 to be positioned between adjacent interspinous processes, i.e., within an interspinous space.

The individual extension arms may have any angle curvature and/or contouring to facilitate anatomical engagement within the interspinous space and/or to enable a "stacking" arrangement of spacer devices for use in multiple, adjacent interspinous spaces. Additionally, the spacers may include an element which enables them to be interconnected or attached to each other in either a fixed or dynamic fashion (e.g., by vertical overlap or interconnection) to accommodate a multiple level procedure. The configuration, shape, width, length and awl separation distances of the distal and proximal extensions may vary from each other and from device to device, where the particular parameters and dimensions are selected to best fit the anatomy of the particular spine being treated. For example, the particular dimensions May vary between the extension pairs where one pair (e.g., the distal extensions) may primarily function to distract and/or providing load-bearing support to the vertebrae and the other pair (e.g., the proximal extensions) may primarily function to maintain the position of the device and resist migration. In the embodiment of FIG. 32, for example, distal extension 392, 396 have shorter, blunter extension arms 394a, 294b, 398a, 398b so as to fit within and better engage the "crotch" of the interspinous space. On the other hand, proximal extensions 384, 388 have longer arms 386a, 386b, 390a, 390b for engaging the outer surfaces or side walls of the spinous processes, thereby preventing lateral displacement or migration of the spacer.

Each of the distal and, proximal extension members may be interconnected to body 382 and/or to each other in a manner which enables them to be moved simultaneously or independently of each other. The extension members may be attached in a spring loaded fashion whereby the natural or biased position of the extension pairs is in a deployed or higher profile state. Alternatively, the extension members may be biased in an undeployed state which may facilitate abandonment, if desired or indicated, of the implant procedure prior to full deployment of the extension members or removal of the device after implantation. Still yet, the manner of attachment may be such to enable or require manual actuation in order to move or deploy the arm pairs and/or to undeploy the arm pairs.

The extension member or arm pairs are movable between at least two states or positions by way of their attachment to block 382, for example, by a hinge means or the like. In certain embodiments, deployment involves rotational movement where the extension member(s) traverses an arc within the range from 0 degrees to about 90 degrees or less with respect to the longitudinal axis defined by block 382. In other embodiments, the extension member(s) traverses an arc within the range from 0 degrees to greater than 90 degrees with respect to the longitudinal axis defined by block 382. The deployment of the device from a low-profile state to a high-profile state may immediate or gradual, where the extent of rotation is controllable. The deployment may occur in multiple discrete steps, in one-step, or evolve in a continuous fashion until the desired angle of deployment is achieved. Additionally, complete or full deployment may further involve the extension of a dimension, e.g., height, after the device is in an expanded state.

To deliver and deploy device 380 within the body, the device is releasably attached to a delivery rod 406 or the like at a proximal end or side, such as attached to body 382 at a location between proximal extension pairs 384 and 388. Device 380 is provided or otherwise placed in its undeployed state as illustrated in FIG. 32A. In the undeployed state, and attached to the delivery rod 406, device 380 is inserted into port or cannula 400 (if not already preloaded therein) which has been operatively positioned with a patient's back as described previously. (In some circumstances it may not be necessary to use a cannula where the device is inserted through a percutaneous opening in the skirt.) Cannula 400 has an inner diameter which allows translation of device 380 there through and a relatively narrow outer diameter to minimize the size of the access site required. The inner diameter of cannula 400 typically ranges form about 5 mm to about 10 mm but may be smaller or larger depending on the application. The outer diameter may be up to 15 mm; however, the lower the profile, the less invasive the procedure. The device is then advanced through cannula 400 to within the targeted interspinous space. Device 380 is advanced beyond the distal end of cannula 400 or cannula 400 is pulled so that its distal end is retracted proximally of device 380. Depending on the particular device configuration being used, the distal and proximal extension members are released and allowed to passively deploy or are otherwise actively deployed by actuation of delivery rod 406. The order of deployment between the distal and proximal extension members may vary between embodiments where both members may be simultaneously deployed or deployed in a staged or serial fashion where the proximal pairs may be deployed prior to the distal pairs or vice-versa, or the superior pairs may be deployed prior to the inferior pairs or vice-versa.

As mentioned above, the extension members may be deployed in stages or be incrementally extended subsequent to deployment. For example, in the illustrated embodiment of FIGS. 32A-32C, distal extension members 392, 396 are designed to be additionally, e.g., vertically, extended from each other and or spacer body 382 subsequent to initial deployment, as illustrated by arrow 408 in FIG. 32C. This may be accomplished by actuation of rod 406 or the members may be coupled to body 382 in a manner where additional extension is automatic upon full deployment. This feature allows for adjusting the amount of distraction between the vertebrae. If necessary, distraction adjustment can be performed post surgically, such as more than twenty-four hours after implantation of the device, by reinserting actuation rod 406 into the interspinous space and re-engaging it with the spacer.

Figure 33A:
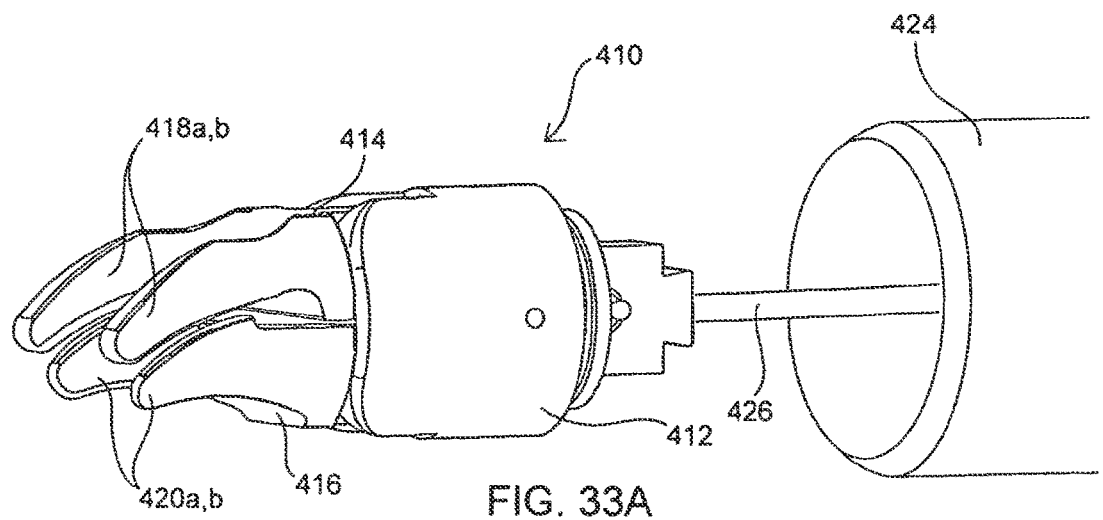
FIGS. 33A-33C illustrate another stabilizing device of the present invention deliverable through a posterior midline approach, where the device is shown in various configurations undergone during implantation and deployment of the device.
Figure 33B:
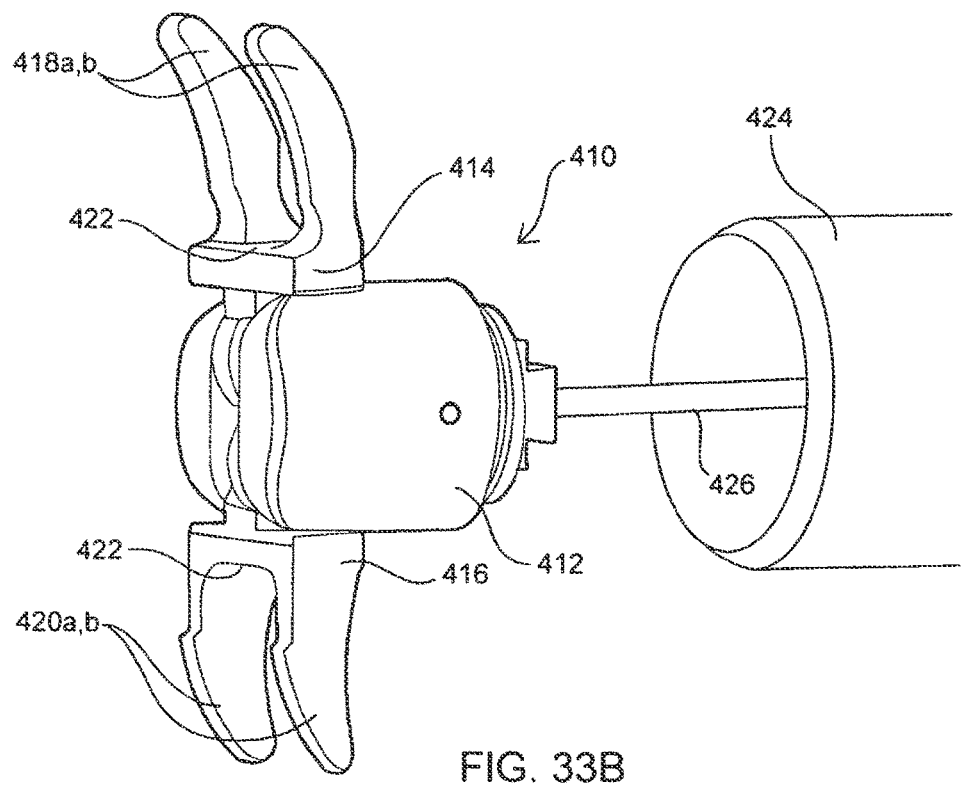
Figure 33C:
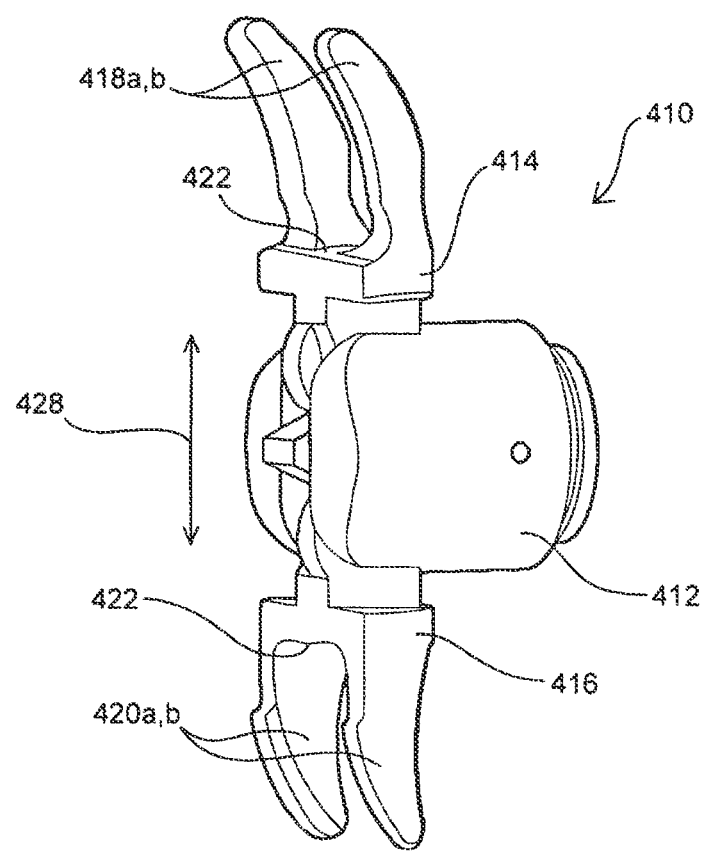

FIGS. 33A-33C illustrate a spacer 410 having a configuration somewhat similar to that of spacer 380 of FIGS. 32A-32C for implantation through a posterior midline approach. Spacer 410 includes a main body or hub or block element 412 which has a cross-sectional size and shape (e.g., cylindrical) that allows for implantation between adjacent spinous processes and facilitates delivery through a narrow port or cannula 424. Spacer 410 further includes two sets of extension members or arm pairs 414, 416 movably or rotatably attached to body 412, for example, by a hinge means or the like to provide rotational movement within about a 90° range. Extension pairs 414 and 416 each include two elongated arms or extensions 418a, 418b and 420a, 420*b*, respectively, which extend substantially parallel to each other in both an undeployed configuration and in a fully-deployed configuration. Extending between each arm pair is a strut, bridge, bracket or saddle 422. The resulting "U" configuration of each the extension pairs enables device 410 to receive adjacent interspinous processes and engage the surfaces thereof.

The arm pairs are rotationally movable between at least an undeployed, collapsed or folded state (FIG. 33A) and a fully deployed state (FIG. 33B). In the undeployed state, the arm pairs are aligned generally or substantially axially (i.e., axially with the longitudinal axis defined by body 412 or to the translation path into the interspinous space) to provide a minimized radial profile. In the deployed state, the arm pairs are positioned generally or substantially transverse to the collapsed position (i.e., transverse to the longitudinal axis defined by body 412 or to the translation path into the interspinous space). The extension members may also be linearly moveable or translatable from the deployed state (FIG. 33B) to an additionally extended state (FIG. 33C). More specifically, the members can be extended in the vertical direction (along an axis parallel to the spine) wherein the members are extended away from each other as denoted by arrow 428 in FIG. 33C.

Extension pairs 414 and 416 may be interconnected to body 412 and/or to each other in a manner which enables them to be moved simultaneously or independently of each other, as well as in a manner to provide passive deployment and/or vertical extension or, alternatively, active or actuated deployment and/or vertical extension. For example, the extension pairs may be attached in a spring loaded fashion whereby the natural or biased position of the extension pairs is a deployed state, or the manner of attachment may be such to enable manual actuation in order to move the arms.

To deliver and deploy device 410 within the body, the device is releasably attached to a delivery rod 426 or the like at a proximal end or side of body 412. Device 410 is provided or otherwise placed in its undeployed state as illustrated in FIG. 33A. In the undeployed state, and attached to the delivery rod 416, device 410 is inserted into port or cannula 424 (if not already preloaded therein) (shown in FIG. 33A) which has been operatively positioned with a patient's back as described previously. (In some circumstances it may not be necessary to use a cannula where the device is inserted through a percutaneous opening in the skin.) The device is then advanced through cannula 424 to within the targeted interspinous space. Device 410 is advanced beyond the distal end of cannula 424 or, alternatively, cannula 424 is pulled so that its distal end is retracted proximally of device 410. Depending on the particular device configuration being used, the extension members 414, 416 are released and allowed to passively deploy or are otherwise actively deployed by actuation of delivery rod 426. The order of deployment between the superior and inferior extension members may vary between embodiments where both members may be simultaneously deployed or deployed in a staged or serial fashion where the superior pair may be deployed prior to the inferior pair or vice-versa. The extension members 414, 416 may then be vertically extended, if necessary or desired, to optimize positioning, fit and securement of the spacer within the interspinous space or to provide further distraction between the adjacent spinous processes. If performing a multi-level procedure, this process may be repeated to implant one or more other spacers through adjacent or spaced apart interspinous spaces.

Figure 38A:
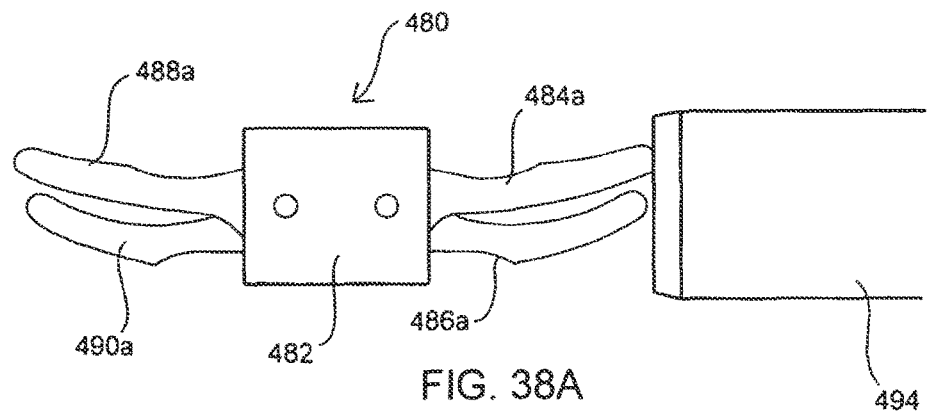
FIGS. 38A-38C illustrate a stabilizing device of the present invention suitable for delivery to an implant site through a lateral approach.
Figure 38B:
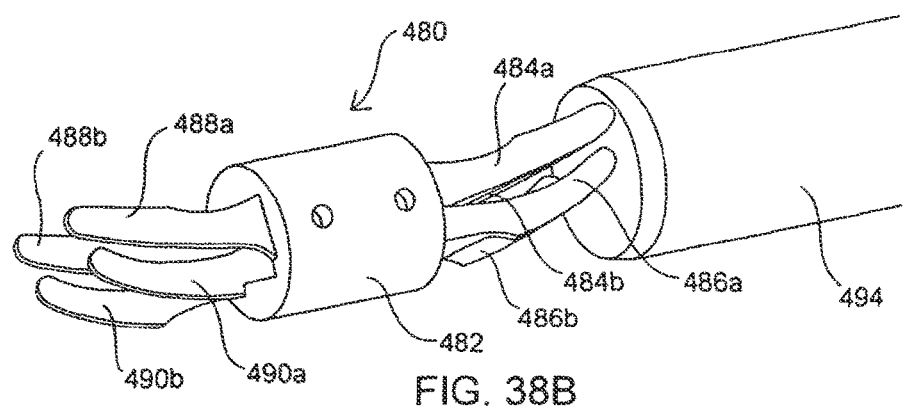
Figure 38C:
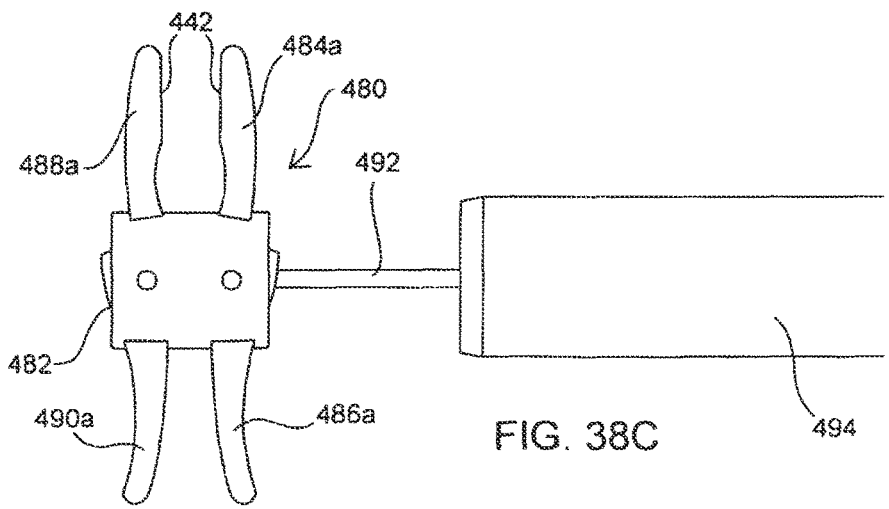

FIGS. 38A-38C illustrate another variation of a mechanical spacer 480 of the present invention which is configured for implantation within an interspinous space by way of a lateral approach, i.e., through one or more incisions made laterally of the spine. Spacer 480 has a main body, hub or block element 482. Hub 482 has a cross-sectional size and shape (e.g., cylindrical, oval, geometric, triangular, etc.) that allows for implantation between adjacent processes and facilitates delivery through a narrow port or cannula 500. Spacer 480 further includes four sets of extension or arm pairs 484*a* and 484*b*, 486*a* and 486*b*, 488*a* and 488*b*, 490*a* and 490*b*, each member or pair of arms of which is movable between an undeployed or collapsed state (FIG. 38A and FIG. 38B) and a deployed or expanded state (FIG. 38C). In the undeployed state, the extension member or arm pairs are aligned generally or substantially axially to the translation path into the interspinous space (i.e., axially with the longitudinal axis defined by body 482), or otherwise characterized as substantially transverse to the spine's axis (when spacer 480 is operatively implanted), to provide a minimized profile (e.g., a minimized radial profile with respect to the longitudinal axis defined by body 482). In the deployed state, the extension member or arm pairs are positioned generally or substantially transverse to the collapsed position (i.e., transverse to the longitudinal axis defined by body 482 or to the translation path into the interspinous space) and substantially parallel to the spine's axis (when spacer 480 is operatively implanted).

The extension member or aim pairs are movable between at least two states or positions by way of their attachment to block 482, for example, by a hinge or pivoting means or the like to provide rotational movement within about a 90° range or more. Two of the extension pairs 484*a* and 484*b*, 486*a* and 486*b* are positioned at a proximal end or side of hub 482 (i.e., "proximal" being defined as that which is closest to the physician user during delivery of the device) and are "folded" in a proximal direction when in an undeployed state. The other two extension pairs 488*a* and 488*b*, 490*a* and 490*b* are positioned at a distal end or side of hub 482 and are "folded" in a distal direction when in an undeployed state. As with the spacers configured for a posterior midline implantation approach, the proximal extension arms and the distal extension members may be interconnected to body 482 and/or to each other in a manner which enables them to be moved simultaneously or independently of each other. Actuation of the aims from an undeployed to a deployed state, and vice versa, is accomplished by manipulation of delivery rod 492. As with the above-described spacers, the extension arms may be further extended, either subsequent to or prior to deployment.

Any of the spacers described herein which are configured for implantation through a percutaneous incision, may be so implanted according to a method of the present invention which involves selective dissection of the supraspinous ligament in which the fibers of the ligament are separated or spread apart from each other in manner to maintain as much of the ligament intact as possible. This approach avoids crosswise dissection of or cutting the ligament and thereby reduces healing time and minimizes the amount of instability to the affected spinal segment. While this approach is ideally suited to be performed through a posterior or midline incision, the approach may also be performed through one or more incisions made laterally of the spine.

FIGS. 39A-39C illustrates a tool 500 which facilitates this less invasive approach through the supraspinous ligament. Tool 500 includes a shaft or cannula body 502 having internal dimensions for the passage of a spacer there through. The distal end 504 of cannula 502 is equipped with at least one radially extending blade 506 whereby the delivery tool can also be used to dissect tissue. Where two blades 506 are employed, as with the illustrated embodiment, they are positioned diametrically opposite each other to provide a substantially straight or linear incision or pathway. As such, tool 500 can be rotationally positioned at a location posterior to the interspinous space into which a device is to be planted, whereby the blades are vertically aligned with the supraspinous ligament fibers. Distal end 504 of cannula 502 may also have a tapered configuration to further facilitate penetration of the cannula into the interspinous space. The proximal end 508 of cannula 502 is configured to receive a spacer implant and instruments for advancing and deploying the spacer. Proximal end 508 may be provided with a handle 510 to enable hand-held manipulation of tool 500 by a physician user. Handle 510 allows tool 500 to be distally pushed, proximally pulled, and rotated, if desired.

Other variations and features of the various mechanical spacers described above are covered by the present invention. For example, a spacer device may include only a single extension member or a single pair of extension arms which are configured to receive either the superior spinous process or the inferior spinous process. The surface of the device body opposite the side to which the extension arms are deployed may be contoured or otherwise configured to engage the opposing spinous process wherein the device is sized to be securely positioned in the interspinous space and provide the desired distraction of the spinous processes defining such space. The additional extension of the extension members subsequent to their initial deployment in order to effect the desired distraction between the vertebrae may be accomplished by expanding the body portion of the device instead of or in addition to extending the individual extension members.

The extension arms of the subject device may be configured to be selectively movable subsequent to implantation, either to a fixed position prior to closure of the access site or otherwise enabled or allowed to move in response to normal spinal motion exerted on the device thereafter. The deployment angles of the extension arms may range from less than 90° (relative to the axis defined by the device body) or may extend beyond 90° where each extension member may be rotationally movable within a range which is different from that of the other extension members. Additionally, the individual extension arms may be movable in any direction relative to the strut or bridge extending between an awl pair or relative to the device body in order to provide shock absorption and/or function as a motion limiter, particularly during lateral bending and axial rotation of the spine. The manner of attachment or affixation of the arm to the extension member may be selected so as to provide movement of the extension arms which is passive or active or both.

For example, the extension arm 430, illustrated in FIGS. 34A and 34B, having a rigid structure 432 may comprise a joint 434 which allows the arm 430 to bend or pivot to passively accommodate loads 436 that are applied to it, e.g., from the side, during normal motion of the spine in order to avoid injury to the spinous process and other tissue structures. Joint 434 may be made of any flexible material or component, such as a polymer or a spring, configured to be resiliently biased and/or plastically deformable upon application of a load. In this way, arm 430 acts as a shock absorber. Joint 434 may be configured to bend in all degrees of freedom or in limited degrees of freedom, e.g., within a single plane, FIGS. 35A and 35B illustrate an extension member 440 having arms 442a, 442b which are pivotally connected to bridge 444 at joints 446. Joints 446 may comprise screws or the like which can be rotated or the like with a driving member or the like upon implant to pivot arms 442a and 442b inward against the spinous process 447 which they straddle. The joints may be configured so that the compression by arms 442a, 442b is tight and rigid against spinous process 447 or may be spring-loaded or resiliently biased to allow some flexibility or give when a force is applied to an arm. As such, the arms can act as motion limiters, resiliently biased force applicators, as well as shock absorbers. The arm positioning may also be reversed (i.e., moved outward) in order to readjust the position of the device or to remove the device from the implant site altogether.

Figure 37:
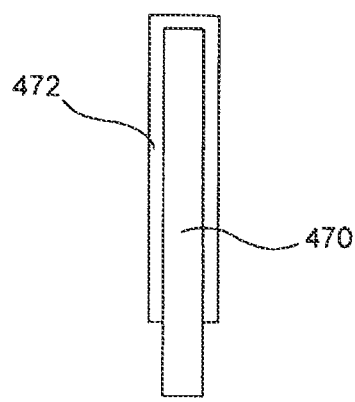
FIG. 37 illustrates an extension arm usable with the extension members of the present invention which has a shock absorbent covering.

Another variation of a shock absorbing extension arm is provided in FIG. 37. Extension arm 470 includes a covering 472 of shock absorbing material 472 such as an elastomeric material which avoids any damage that may be caused to the bones by an otherwise bare surface of the extension arm. The shock absorption feature may alternatively be integrated with the strut or bridge component of the extension member.

Figure 36A:
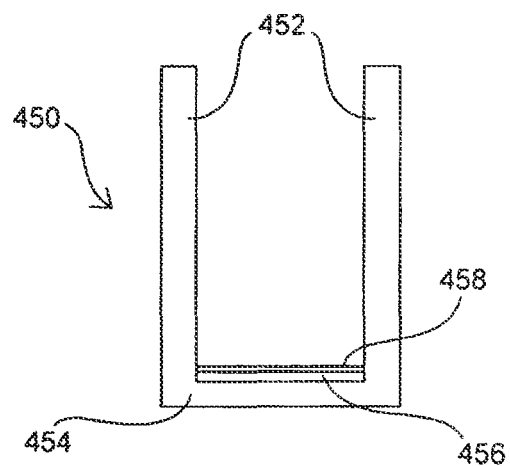
FIG. 36A illustrates an extension member of the present invention having a shock absorbing saddle or bridge member.

Referring to FIG. 36A, an extension member 450 usable with the mechanical spacers of the type described with respect to FIGS. 32 and 33, for example, is provided having extension arms 452 affixed to a bridge component 454. Lining the top or inner surface of bridge 454 is a shock absorber 456 made of a compressible material, such as elastomeric material. Optionally, a hard plate 458, made of a more rigid material, such as stainless steel or the like, may be provided on top of the elastomeric material so as to reduce wear and to better distribute the load exerted by the spinous process onto the shock absorber 456.

Figure 36B:
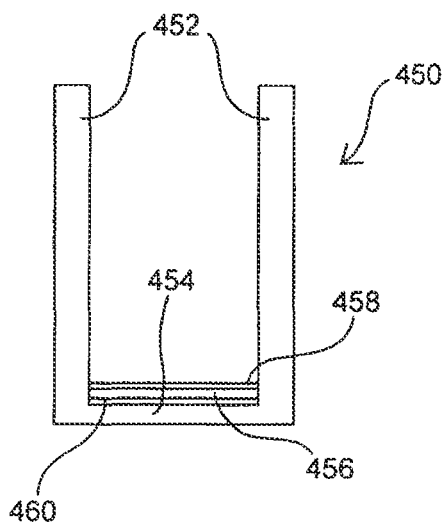
FIG. 36B illustrates the extension member of FIG. 36A having an additional feature which enables the saddle or bridge member to provide a dual response shock absorbency.

The shock absorber component may be configured to provide "dual response" absorption to loads exerted on it. FIG. 36B illustrates one manner in which to effect such a dual response with the extension member 450 of FIG. 36A. Here, a second layer of shock absorbing Material 460 is added to the stacked shock absorber. The first or top layer 456 of the shock absorber accommodates loads resulting from normal motion of the spine while the second or bottom layer 460 of the shock absorber acts as a safety ne to prevent damage in extreme load conditions. The dual response can be fine timed by selecting shock absorbing materials which have varying durometer values (Newtons), e.g., where the durometer of the first layer is lower than that of the second layer or vice versa.

Figure 36C:
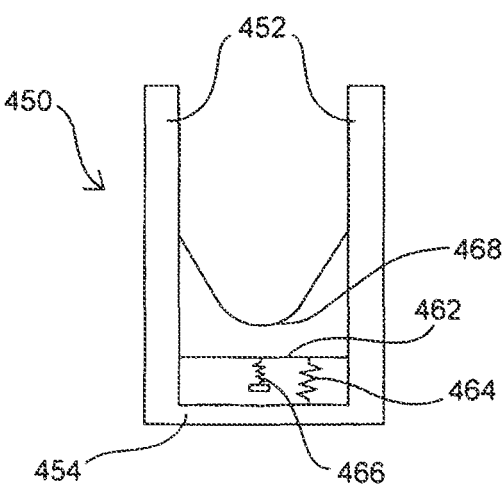
FIG. 36C illustrates another variation of a dual response shock absorbent saddle or bridge member.
Figure 36D:
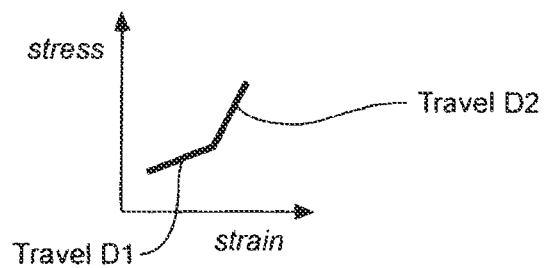
FIG. 36D is a graphical representation of the stress and strain undergone by saddle member of FIG. 36C.

FIG. 36C illustrates another variation by which to provide two levels of load response on extension member 450. Here, shock absorber 462 includes two spring mechanisms 464 and 466 where the first spring 464 is initially responsive to loads exerted on shock absorber 462 to allow for a first travel distance D1 (see FIG. 36D) and the second spring 466 provides additional resistance and shock absorption for a distance D2 after travel distance D1. A graphical representation of the stress and strain undergone by shock absorber 462 is illustrated in FIG. 36D.

With any of the extension members described, a cushioning or padding member 468 (see FIG. 36C) maybe used in addition to or in lieu of a shock absorber. The bone-contacting surface of the cushion 468 may have any shape or contouring to achieve the desired effect or to match that of the bone surface to be contacted. For example, the bone-contacting surface may have a concave configuration so as to cradle the interspinous process.

Other optional features which may be employed with the subject spacers include the use of biodegradable materials to form the entire spacer structure or one or more portions thereof. In one variation, a rigid spacer structure having biodegradable portions, e.g., extension members or arms, is implanted within an interspinous space or elsewhere to provide temporary fixation of a spinal motion segment. Upon degradation of the biodegradable portions of the spacer, the remaining-spacer structure provides dynamic stabilization to that spinal motion segment. In another variation, the spacer device may be made wholly of non-biodegradable materials and configured to be anchored to a bony structure with a biodegradable securing member, e.g., a screw. As such, upon implantation of the spacer and its securement to both vertebrae between which it is implanted, for example, the spacer functions to "fuse" the vertebrae together. Subsequent degradation of the screws will release the fixed interconnection between the spacer and the bone thereby enabling it to dynamically stabilize the spinal motion segment. The half life of the biodegradable material may be selected so as to delay degradation until a minimum level of healing and improvement is achieved.

With other embodiments of the subject spacers, the static-to-dynamic function of the spacers is reversed, i.e., the spacer is initially implanted for dynamically stabilizing a spinal motion segment, and then subsequently converted to fuse that same segment. The spacer may be configured to be anchored or secured to a bony structure of the vertebrae, such as one of the spinous processes between which it is implanted. Such capability would allow a physician to convert a spinal stabilization procedure to a fusion procedure if upon commencing the implant procedure, the spinal motion segment being treated is observed to require such. Alternatively, such a device would allow a fusion procedure to be performed subsequently (e.g., months or years later) to the dynamic stabilization procedure should the affected spinal motion segment degenerate further. Thus, without having to remove the device and/or implant additional components (other than bone screws or the like), trauma to the patient and the cost of the procedure is greatly minimized.

Visualization markers or the like may be employed at various locations on the spacer for a variety of purposes. For example, markers may be used to ensure proper placement of the spacer prior to deployment. Markers on opposite sides of a spacer body would ensure that the spacer body has been fully advanced within the interspinous space and that it is in a proper rotational alignment to ensure that the extension arms clear the spinous processes when deployed. Linear marks or grooves aligned relative to the spacer body axis may be useful for this purpose. Other markers may be employed on the spacer delivery or insertion tool, for example, on the blades of the cannula of FIG. 39 or elsewhere at its distal end in order to visualize the distal end upon penetration into skin. Markers on the extension members themselves could be used to identify their deployment angle and to confirm their complete and adequate deployment and/or extension within the interspinous space. The markers may be made of one or more types of material for visualizations by various modalities, e.g., radiographic for fluoroscopic/x-ray visualization, textures or air bubbles for ultrasound, etc.

Various coatings may be employed over the entire surface of the spacer or a portion (a "zoned" area) thereof including but not limited to antibiotics, lubricous materials, stem cells, extracellular matrices, growth factors, etc. For example, a lubricous coating could prevent the implant from "sticking" to bone and facilitate easier implantation.

As mentioned above with respect to FIGS. 14A-14F, the vertebral bodies of the spinal segments being treated may be distracted prior to implantation of the subject spacers. This may be accomplished by the spacer insertion device itself (e.g., tool 500 or another insertion device) or by a separate instrument. The need for pre-distraction maybe assessed by way of diagnostic measurements performed prior to the implant procedure by means of an imaging apparatus (e.g., X-ray, MRI, ultrasound, fluoroscopy, CT-scan, etc.). Additionally, the same imaging systems may be used to confirm post-surgical distraction and proper placement of the implant.

Implant size and/or geometry selection is also facilitated by use of such imaging systems prior to the implantation procedure. The appropriate size and/or geometry of the implant may also be determined by using a temporary implant which can be adjusted in size or shape to determine the ideal size and geometry of the permanent implant to be selected. Alternatively, a selection of temporary implants may be provided and implanted until the one having the suitable size and/or geometry has been determined. Certain other factors including patient-specific parameters may also be taken into consideration when determining the proper implant size and geometry. Relevant patient parameters include but are not limited to anatomical geometry of the patient, the disease state of the patient; the trauma state of the patient and combinations thereof.

The subject devices and systems may be provided in the form of a kit which includes at least one interspinous device of the present invention. A plurality of such devices may be provided where the devices have the same or varying sizes and shapes and are made of the same or varying biocompatible materials. Possible biocompatible materials include polymers, plastics, ceramic, metals, e.g., titanium, stainless steel, tantalum, chrome cobalt alloys, etc. The kits may further include temporary device implants used for sizing a device to be permanently implanted, instruments and tools for implanting the subject devices, including but not limited to, a cannula, a trocar, a scope, a device delivery/inflation/expansion lumen, a cutting instrument, a screw driver, etc., as well as a selection of screws or other devices for anchoring the spacer tabs to the spinous processes. The kits may also include a supply of the expandable body inflation and/or expansion medium. Instructions for implanting the interspinous spacers and using the above-described instrumentation may also be provided with the kits.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A device for implantation in a subject, comprising:
 a first member including first extension members and a first contact section;
 a second member including second extension members and a second contact section; and
 a main body rotatably coupled to the first and second members and including at least one drive component and a delivery instrument interface configured to be releasably coupled to a delivery instrument such that operation of the delivery instrument by a user causes rotation of the first extension members and the first contact section relative to the main body and/or rotation of the second extension members and the second contact section relative to the main body such that the first and second members move from an undeployed configuration to a deployed configuration, wherein the delivery instrument interface moves in response to operation of the delivery instrument to controllably move the at least one drive component to gradually drive the first and/or second members toward the deployed configuration, wherein the first and second extension members are positioned to be inserted between a first spinous process and a second spinous process when in the undeployed configuration, wherein the first extension members are spaced apart from one another so as to be positioned on opposite sides of the first spinous process when the first member is in the deployed configuration and when the first contact section is positioned at the interspinous space, and wherein the second extension members are spaced apart to be positioned on opposite sides of the second spinous process when the second member is in the deployed configuration and when the second contact section is positioned at the interspinous space.

2. The device of claim 1, further comprising a pin rotatably coupling the first member to the main body, and wherein the first extension members and the first contact section form a U-shaped portion of the first member.

3. The device of claim 1, wherein
 the first extension members extend in an anterior direction relative to the main body when the first member is in the undeployed configuration, and wherein the first extension members extend in a superior direction relative to the main body when the first member is in the deployed configuration, and
 the second extension members extend in an anterior direction relative to the main body when the second member is in the undeployed configuration, and wherein the second extension members extend in an inferior direction relative to the main body when the second member is in the deployed configuration.

4. The device of claim 3, wherein the first and second extension members and a long axis of the main body extend in an anterior-to-posterior direction relative to the subject's spine when the first and second members are in the undeployed configuration and the main body is at an interspinous space between the first and second spinous processes.

5. The device of claim 1, wherein the first contact section is saddle shaped.

6. The device of claim 1, wherein at least a portion of the main body is positioned directly between the first and second contact sections when the first and second members are in the deployed configuration.

7. The device of claim 1, wherein the first extension members and the second extension members extend in opposite directions when the first and second members are in the undeployed configuration.

8. The device of claim 1, wherein the first member is rotatable about a first axis of rotation relative to the main body, wherein the second member is rotatable about a second axis of rotation relative to the main body, and wherein the first and second axes of rotation are substantially parallel to one another.

9. The device of claim 8, wherein the first and second axes are substantially perpendicular to a sagittal plane of the device.

10. The device of claim 1, wherein
 each of the first extension members defines a first long axis that
  extends in an anterior direction relative to the subject when the first member is in the undeployed configuration and the main body is at the interspinous space, and
  extends in a superior direction relative to the subject when the first member is in the deployed configuration and the main body is at the interspinous space; and
 each of the second extension members defines a second long axis that
  extends in the anterior direction relative to the subject when the second member is in the undeployed configuration, and
  extends in the inferior direction relative to the subject when the second member is in the deployed configuration.

11. A device for implantation in a subject, comprising:
 a first member including a first U-shaped portion with first ends spaced apart to receive a superior spinous process therebetween;
 a second member including a second U-shaped portion with second ends spaced apart to receive an inferior spinous process therebetween; and
 a main body rotatably coupled to the first and second members such that the first and second U-shaped portions receive respective superior and inferior spinous processes when the main body rotates the first and second members from an undeployed configuration for delivering the first and second members into an interspinous space to a deployed configuration for engaging an inferior region of the superior spinous process and a superior region of the inferior spinous process, wherein the interspinous space is directly between the inferior region and the superior region, wherein the main body includes at least one drive component and a delivery instrument interface configured to couple to a delivery instrument, and wherein the delivery instrument interface moves in response to operation of the delivery instrument to controllably move the at least one drive component to gradually drive the first and second members toward the deployed configuration.

12. The device of claim 11, wherein a portion of the main body is positioned directly between saddle shaped portions of the first and second U-shaped positions when the first and second members are in the deployed configuration.

13. The device of claim 11, wherein the first member traverses an arc of about 90 degrees when the first member moves from the undeployed configuration to the deployed configuration.

14. The device of claim 11, wherein at least one of the first and second members is positioned substantially perpendicular to a longitudinal axis of the main body when the least one of the first and second members is in the deployed configuration.

15. The device of claim 11, wherein the first and second members rotate relative to the main body in response to an actuator moving through the main body.

16. The device of claim 11, wherein the first U-shaped portion includes
   a pair of elongate arms including the first ends that define an opening for receiving the superior spinous process, and
   a contact region extending between the elongate arms.

17. The device of claim 11, wherein at least one of the first and second members is positioned substantially perpendicular to a longitudinal axis of the main body when the at least one of the first and second members is in the deployed configuration.

* * * * *